United States Patent
Bosmans et al.

(10) Patent No.: US 8,263,592 B2
(45) Date of Patent: Sep. 11, 2012

(54) EQUILIBRATIVE NUCLEOSIDE TRANSPORTER ENT1 INHIBITORS

(75) Inventors: Jean-Paul René Marie André Bosmans, Rijkevorsel (BE); Didier Jean-Claude Berthelot, Antwerpen (BE); Serge Maria Aloysius Pieters, Hulst (NL); Bie Maria Pieter Verbist, Pulle (BE); Michel Anna Jozef De Cleyn, Lille (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 12/742,807

(22) PCT Filed: Nov. 13, 2008

(86) PCT No.: PCT/EP2008/065438
§ 371 (c)(1),
(2), (4) Date: May 13, 2010

(87) PCT Pub. No.: WO2009/062990

PCT Pub. Date: May 22, 2009

(65) Prior Publication Data

US 2010/0280025 A1    Nov. 4, 2010

(30) Foreign Application Priority Data

Nov. 14, 2007    (EP) ...................................... 07120630

(51) Int. Cl.
C07D 498/10    (2006.01)
A61K 31/537    (2006.01)
(52) U.S. Cl. .......... 514/230.5; 514/278; 546/17; 544/71
(58) Field of Classification Search .................... 544/71; 514/230.5, 278; 546/17
See application file for complete search history.

(56) References Cited

U.S. PATENT DOCUMENTS

| 2001/0039286 A1 | 11/2001 | Dinnell et al. |
| 2007/0117823 A1 | 5/2007 | Antel et al. |

FOREIGN PATENT DOCUMENTS

| WO | WO 98/046611 A | 10/1998 |
| WO | WO 2004/060902 A | 7/2004 |
| WO | WO 2007/118151 A | 10/2007 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
PCT Written Opinion PCT/EP2008/065438, 5 pages, Jul. 3, 2009.
PCT International Search Report PCT/EP2008/065438, 4 pages, Jul. 3, 2009.

* cited by examiner

*Primary Examiner* — Kahsay T Habte
(74) *Attorney, Agent, or Firm* — Joseph S. Kentoffio

(57) ABSTRACT

The present invention is related to novel compounds of formula (I) having equilibrative nucleoside transporter ENT1 inhibiting properties, pharmaceutical compositions comprising these compounds, chemical processes for preparing these compounds and their use in the treatment of diseases linked to the inhibition of ENT1 receptors in animals, in particular humans.

(I)

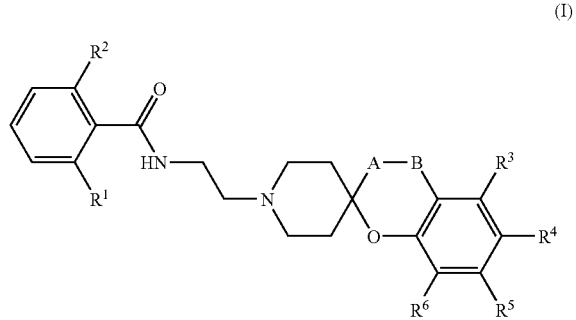

12 Claims, No Drawings

EQUILIBRATIVE NUCLEOSIDE TRANSPORTER ENT1 INHIBITORS

CROSS REFERENCE TO RELATED APPLICATIONS

This application is a national stage application of Patent Application No. PCT/EP2008/065438, filed 13 Nov. 2008, which in turn claims the benefit of EPO Patent Application No. 07120630.4 filed 14 Nov. 2007. The complete disclosures of the aforementioned related patent applications are hereby incorporated herein by reference for all purposes.

The present invention is related to novel compounds of formula (I) having equilibrative nucleoside transporter ENT1 inhibiting properties, pharmaceutical compositions comprising these compounds, chemical processes for preparing these compounds and their use in the treatment of diseases linked to the inhibition of ENT1 receptors in animals, in particular humans.

Specific transporters are required for the permeation of nucleosides across cell membranes. Among the family of nucleoside transporters the equilibrative nucleoside transporters (ENTs) are the most broadly expressed and four human ENTs have been identified in humans: hENT-1, hENT-2, hENT-3 and hENT-4. The most thoroughly characterized are hENT-1 and hENT-2 which are cell surface proteins and are broadly selective for both purine and pyrimidine nucleosides. They can be distinguished from each other by their sensitivities to inhibition by nitrobenzylmercaptopurine riboside (NBMPR). ENT1 is potently inhibited by nanomolar concentrations of NBMPR and is therefore also called a NBMPR sensitive equilibrative nucleoside transport protein. ENT2 is insensitive to nanomolar concentrations of NBMPR, but can be inhibited by higher (micromolar) concentrations of NBMPR and is therefore also referred to as a NBMPR insensitive equilibrative nucleoside transport protein (iENTP) [see Griffith et al., *Biochim. Bioph. Acta* 1286:153-181 (1986)].

Adenosine is an endogenous purine nucleoside that is particularly released in pathophysiological conditions like ischaemia, inflammation and pain. Under these circumstances it plays an important neuro- and immunomodulatory role. Adenosine administration is analgesic in various nociceptive modalities in humans. Because of the short half life of adenosine and side-effects caused by its administration, there has been considerable interest in finding ways to reinforce the effects of endogenous adenosine. Inhibition of the ENT1 blocks uptake of adenosine into cells and could enhance its beneficial effects.

The present invention relates to a compound of formula (I)

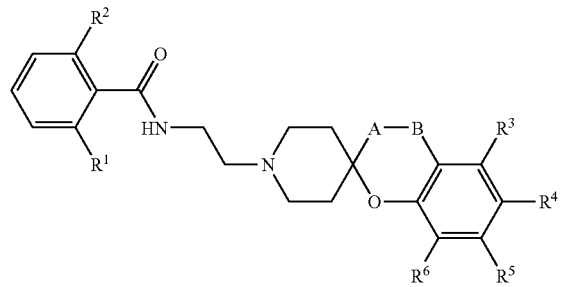

(I)

including any stereochemically isomeric form thereof, wherein

-A-B— represents

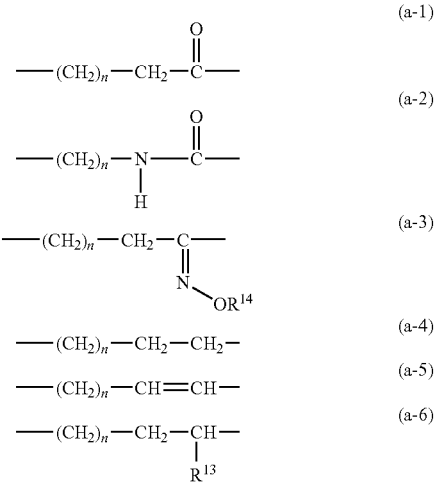

wherein n is an integer 0 or 1;

$R^{13}$ represents hydroxy or halo;

$R^{14}$ represents hydrogen or C1-6alkyl;

in the bivalent radicals (a-4), (a-5) and (a-6) any of the hydrogen atoms on the same or a different carbon atom may be replaced by halo;

$R^1$ and $R^2$ are each independently selected from hydrogen, halo or $C_{1-6}$alkyl;

$R^3$, $R^4$, $R^5$ and $R^6$ are each independently selected from hydrogen, halo, $C_{1-6}$alkyl, polyhalo$C_{1-6}$alkyl, $C_{3-6}$cycloalkyl, $NO_2$, Cycle$^1$, Cycle$^2$, or X—$R^8$ wherein X represents O or $NR^9$, wherein $R^9$ is hydrogen, $C_{1-6}$alkyl or $C_{1-6}$alkyloxy$C_{1-6}$alkyl, and wherein $R^8$ is hydrogen, $C_{1-6}$alkyl, $C_{2-6}$alkenyl, $C_{3-6}$cycloalkyl, polyhalo$C_{1-6}$alkyl, $C_{1-6}$alkyloxycarbonyl, $C_{1-6}$alkylcarbonyl, polyhalo$C_{1-6}$alkylcarbonyl, Cycle$^2$, —(C=O)—(CH$_2$)$_m$-Cycle$^2$, —(C=O)—(CH$_2$)$_m$—CH$_2$—OH, —(C=O)—(CH$_2$)$_m$—CH$_2$—O—C$_{1-4}$alkyl or $C_{1-6}$alkyl substituted with halo, hydroxy, cyano, $C_{3-6}$cycloalkyl, $C_{1-6}$alkyloxy, aminocarbonyl, phenyl, Cycle$^1$, or Cycle$^2$, or $NR^{11}R^{12}$ wherein $R^{11}$ and $R^{12}$ are each independently selected from hydrogen, $C_{1-6}$alkyl, $C_{1-6}$alkylcarbonyl, or $C_{1-6}$alkyloxycarbonyl;

m is an integer 0, 1 or 2;

Cycle$^1$ is selected from

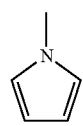

(b-1)

(b-2)

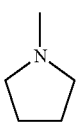
(b-3)

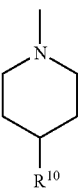
(b-4)

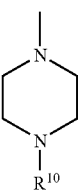
(b-5)

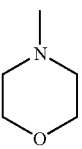
(b-6)

wherein $R^{10}$ is hydrogen, $C_{1-6}$alkyl, $C_{1-6}$alkylcarbonyl, or $C_{1-6}$alkyloxycarbonyl; and
Cycle$^2$ is selected from

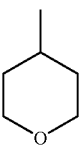
(c-1)

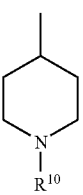
(c-2)

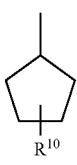
(c-3)

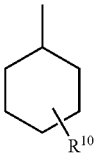
(c-4)

wherein $R^{10}$ is hydrogen, $C_{1-6}$alkyl, $C_{1-6}$alkylcarbonyl, $C_{1-6}$alkyloxycarbonyl or $C_{1-6}$alkyloxycarbonyl substituted with halo or hydroxy;
or a pharmaceutically acceptable acid addition salt thereof, or a solvate thereof, or an N-oxide form thereof.

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;
$C_{1-6}$alkyl is meant to include $C_{1-4}$alkyl and the higher homologues thereof having 5 or 6 carbon atoms, such as, for example, 2-methylbutyl, pentyl, hexyl and the like;
$C_{3-6}$alkenyl defines straight and branched chain unsaturated hydrocarbon radicals having from 3 to 6 carbon atoms, such as propenyl, butenyl, pentenyl or hexenyl;
polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoro-methyl, trifluoromethyl, trifluoroethyl, and the like;
polyhalo$C_{1-6}$alkyl is defined as polyhalosubstituted $C_{1-6}$alkyl, in particular $C_{1-6}$alkyl (as hereinabove defined) substituted with 2 to 6 halogen atoms such as difluoro-methyl, trifluoromethyl, trifluoroethyl, and the like;
$C_{3-6}$cycloalkyl is generic to cyclopropyl, cyclobutyl, cyclopentyl, and cyclohexyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

When the substituents $R^1$ and $R^2$ have a different meaning, the bond between the aryl group and the carbonyl group forms an axis of chirality. The enantiomers of axially chiral compounds are usually given the stereochemical labels $R_a$ and $S_a$ (or aR or aS) and such enantiomers are also embraced under the term "stereochemically isomeric forms".

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

Interesting compounds of formula (I) are those compounds of formula (I) wherein one or more of the following restrictions apply:

a) $R^1$ and $R^2$ are both halo, in particular chloro; or
b) $R^1$ and $R^2$ are both $C_{1-4}$alkyl, in particular methyl; or
c) radical -A-B— represents (a-1); or
d) radical -A-B— represents (a-2); or
e) $R^3$, $R^4$, $R^5$ and $R^6$ are each independently selected from hydrogen, halo, $C_{1-6}$alkyl, or X—$R^8$ wherein X represents O; or
f) $R^3$, $R^4$, $R^5$ and $R^6$ are each independently selected from hydrogen, halo, $C_{1-6}$alkyl, or X—$R^8$ wherein X represents O and $R^8$ represents $C_{1-6}$alkyl or $Het^2$; or
g) $R^3$, $R^4$, $R^5$ and $R^6$ are each independently selected from hydrogen, halo, $C_{1-6}$alkyl, or X—$R^8$ wherein X represents O and $R^8$ represents $Het^2$ wherein $Het^2$ represents radical (c-2); or
h) $R^3$, $R^4$, $R^5$ and $R^6$ are each independently selected from hydrogen, halo, $C_{1-6}$alkyl, or X—$R^8$ wherein X represents $NR^9$; or
i) $R^3$, $R^4$, $R^5$ and $R^6$ are each independently selected from hydrogen, halo, $C_{1-6}$alkyl, or X—$R^8$ wherein $R^8$ is hydrogen and X represents $NR^9$ wherein $R^9$ represents hydrogen; or
j) $R^3$ is hydrogen; or
k) $R^4$ is hydrogen, $C_{1-6}$alkyl or halo; or
l) $R^5$ is X—$R^8$; or
m) $R^6$ is halo; or
n) n is an integer 0.

Other interesting compounds are N-(2-{7-[(1-acetylpiperidin-4-yl)oxy]-6-chloro-4-oxo-3,4-dihydro-1'H-spiro[chromene-2,4'-piperidin]-1'-yl}ethyl)-2,6-dichlorobenzamide, or or N-[2-(7-amino-8-chloro-4-oxo-3,4-dihydro-1'H-spiro[1,3-benzoxazine-2,4'-piperidin]-1'-yl)ethyl]-2,6-dichlorobenzamide, or a pharmaceutically acceptable acid addition salt thereof.

In the following paragraphs there are described different ways of preparing the compounds of formula (I). In order to simplify the structural formulae of the compounds of formula (I) and the intermediates intervening in their preparation, the benzamide moiety will be represented by the symbol T hereinafter.

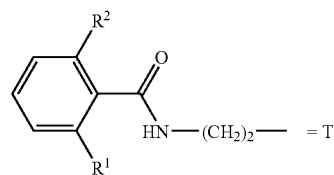

Compounds of formula (I) can generally be prepared by N-alkylating an intermediate of formula (III) with an intermediate of formula (II), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, dichloromethane, or dimethylformamide, and optionally in the presence of a suitable base such as, for example, sodium carbonate, potassium carbonate, triethylamine or diisopropylethylamine (DIPEA). Stirring may enhance the rate of the reaction. The reaction is preferably carried out at a temperature of about 0° C.

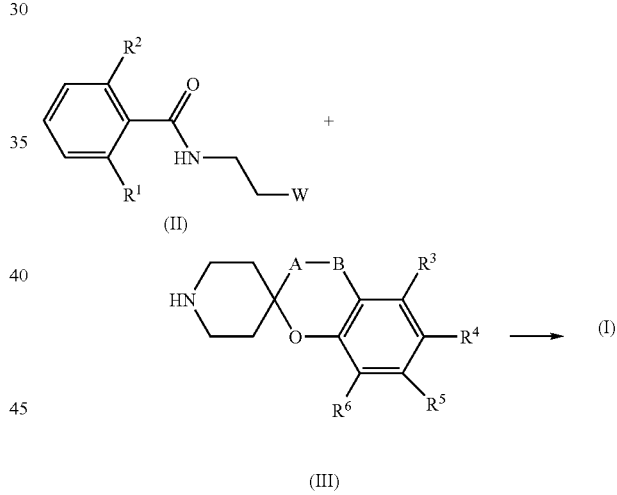

Compounds of formula (I) can also be prepared by reacting an intermediate of formula (IV) with an intermediate of formula (V). The reaction can be performed in a reaction-inert solvent such as, for example, dichloromethane or dimethylformamide and optionally in the presence of a suitable base such as, for example, diisopropylethyl-amine (DIPEA).

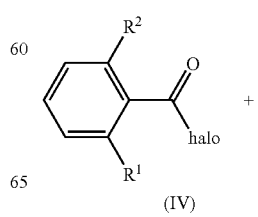

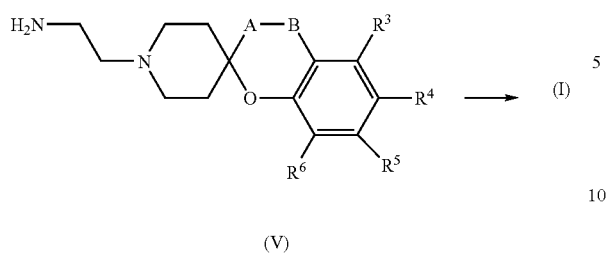

Compounds of formula (I-a,) defined as compounds of formula (I) wherein -A-B— represents radical (a-1) wherein n is 0, can be prepared by reacting intermediates of formula (VI) with intermediates of formula (VII) in a reaction-inert solvent such as methanol in the presence of pyrrolidine.

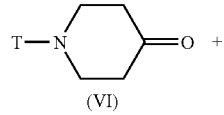

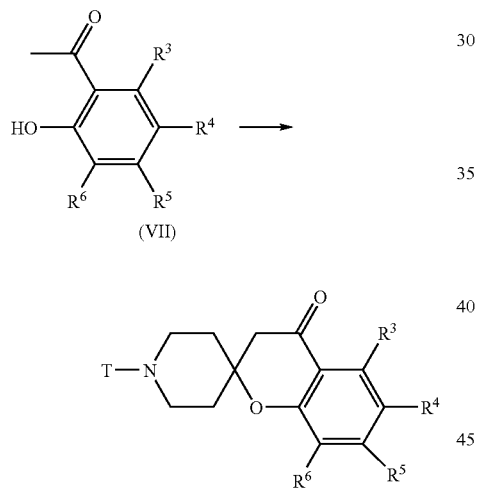

Compounds of formula (I-b,) defined as compounds of formula (I) wherein -A-B— represents radical (a-2) wherein n is 0, can be prepared by reacting intermediates of formula (VIII) with intermediates of formula (IX) in a reaction-inert solvent such as toluene in the presence of pyrrolidine, or toluene in the presence of p-toluenesulfonic acid and molecular sieves.

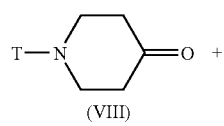

Compounds of formula (I-c,) defined as compounds of formula (I) wherein -A-B— represents radical (a-4) wherein n is 0, can be converted into compounds of formula (I-a) using catalytic hydrogenation conditions, e.g. by using hydrogen gas and a catalyst such as Raney nickel in a reaction-inert solvent such as, e.g. methanol.

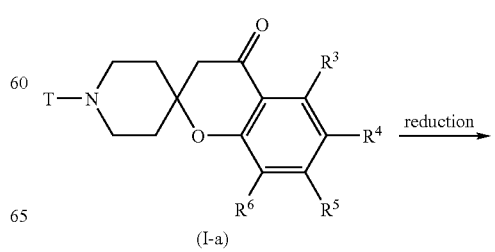

Compounds of formula (I-a) can be converted into compounds of formula (I-d-1), defined as compounds of formula (I) wherein -A-B— represents radical (a-6) wherein $R^{11}$ represents hydroxy and n is 0, by art-known reduction procedures such as, e.g. treatment with sodiumborohydride in a suitable solvent, e.g. methanol.

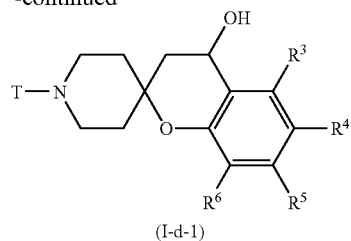

(I-d-1)

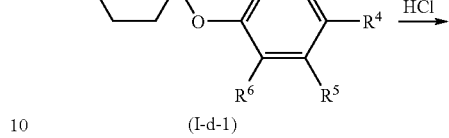

(I-d-1)

Compounds of formula (I-d-1) can be converted into compounds of formula (I-c) by treatment with triethylsilylhydride in the presence of trifluoroacetic acid in a reaction-inert solvent such as dichloromethane.

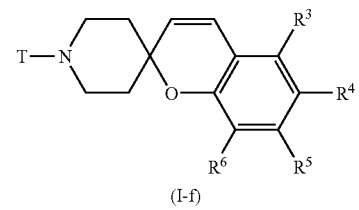

(I-f)

Compounds of formula (I-f,) defined as compounds of formula (I-c) using catalytic hydrogenation conditions, e.g. by using hydrogen gas and a catalyst such as platinum-on-carbon in a reaction-inert solvent such as, e.g. methanol.

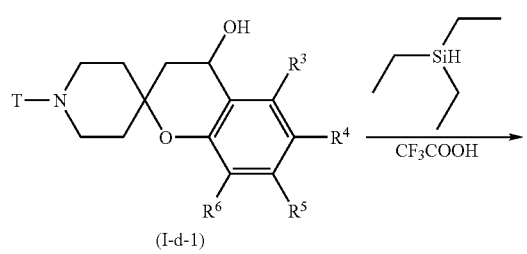

(I-d-1)

(I-c)

Compounds of formula (I-a) can be converted into compounds of formula (I-e), defined as compounds of formula (I) wherein -A-B— represents radical (a-3) wherein n is 0, by treatment with hydroxylamine under basic conditions.

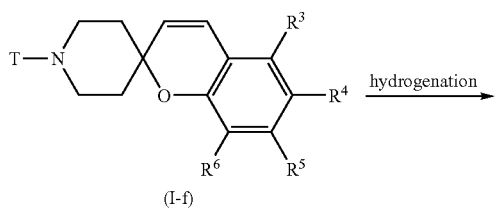

(I-f)

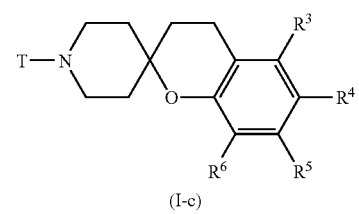

(I-c)

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

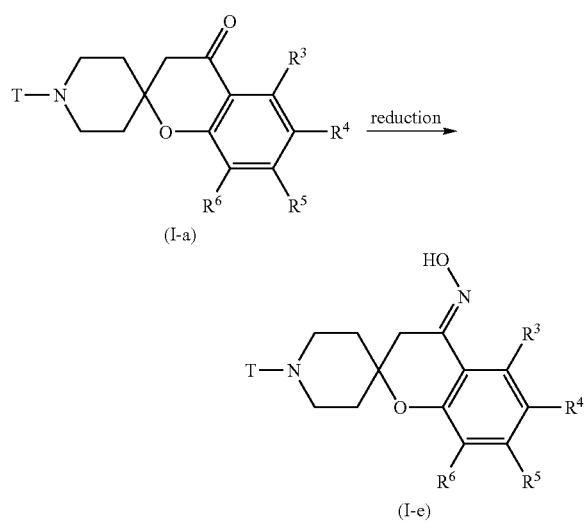

(I-a)

(I-e)

Compounds of formula (I-d-1) can be converted into compounds of formula (I-f), defined as compounds of formula (I) wherein -A-B— represents radical (a-5) wherein n is 0, by treatment with hydrochloric acid in a reaction-inert solvent such as THF.

The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess equilibrative nucleoside transporter ENT1 inhibiting properties as demonstrated in the Pharmacological Example C.1.

Therefore the present compounds of formula (I) are useful as a medicine especially in the treatment of a condition or disease mediated by the equilibrative nucleoside transporter ENT1, in particular equilibrative nucleoside transporter ENT1 inhibitory activity. Subsequently the present compounds may be used for the manufacture of a medicine for treatment of a condition or a disease mediated by equilibrative nucleoside transporter ENT1 activity, in particular equilibrative nucleoside transporter ENT1 inhibitory activity.

The present invention also provides the use of a compound of formula (I) or a pharmaceutically acceptable salt thereof for the manufacture of a medicament for the treatment of conditions or diseases selected from equilibrative nucleoside transporter ENT1 conditions or diseases.

In an embodiment, the present invention provides a compound of formula (I) for use as a medicine or for use in the treatment of conditions or diseases selected from equilibrative nucleoside transporter ENT1 conditions or diseases.

Further, the present invention also provides a method of treatment of a condition mediated by equilibrative nucleoside transporter ENT1 activity, in a mammalian subject, which method comprises administering to a mammal in need of such treatment a therapeutically effective amount of a compound of formula (I) or a pharmaceutically acceptable salt thereof.

Equilibrative nucleoside transporter ENT1 mediated conditions or disorders are e.g. acute and chronic pain conditions including inflammatory pain, neuropathic pain, cancer pain, cardioprotection, cerebroprotection, traumatic brain injury (TBI), myeloprotection, neuroprotection, chronic pressure skin ulcers, wound healing, anticonvulsant, organ transplant (organ preservation, like cardioplegia), sleep disorders, pancreatitis, glomerulonephritis, and antithrombotic (anti-platelet).

Chronic pain conditions are related to hyperalgesia and allodynia. These conditions might include acute pain, skeletal muscle pain, low back pain and radiculopathy, upper extremity pain, fibromyalgia and myofascial pain syndromes, orofacial pain, abdominal pain, phantom pain, tic douloureux and atypical face pain, nerve root damage and arachnoiditis, geriatric pain, central pain, inflammatory pain.

Neuropathic pain results from lesions in the peripheral or central nervous system. It is often associated with somatosensory deficits and the distribution of pain is mostly related to the area of somatosensory dysfunction. The onset of the pain can be delayed after the causative event, even up to months or years. There are several causes of neuropathic pain with a considerable variability in symptoms and neurological deficits. Examples are peripheral nerve damage due to traumatic injury compression, ischemia, toxins, nutritional deficiencies, viral infections and complications of liver and kidney.

The term "treating" and "treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the cannabinoid receptors will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible inhibition of the ENT1 transporters.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: 'CH$_3$OH' means methanol, 'CH$_2$Cl$_2$' means dichloromethane, 'CH$_3$CN' means acetonitrile, 'DIPE' means diisopropyl ether, 'DIPEA' means diisopropylethylamine, 'MgSO$_4$' means magnesium sulphate, 'Na$_2$SO$_4$' means sulfuric acid disodium salt, 'Na$_2$CO$_3$' means carbonic acid disodium salt, 'THF' means tetrahydrofuran, 'EtOH' means ethanol, 'DMF' means N,N-dimethylformamide, 'CF$_3$COOH' means trifluoroacetic acid, 'H$_2$SO$_4$' means sulfuric acid, 'KOAc' means potassium acetate, 'NH$_3$' means ammonia, 'NaBH$_4$' means sodium borohydride, 'NH$_4$Cl' means ammonium chloride, 'NaOH' means sodium hydroxide, 'NaBH(OAc)$_3$' means sodium triacetatohydroborate, 'Pd(OAc)$_2$' means palladium acetate, 'BINAP' means 1,1'-[1,1'-binaphthalene]-2,2'-diylbis[1,1-diphenylphosphine], 'Cs$_2$CO$_3$' means cesium carbonate, 'BBr$_3$' means tribromoborane, 'BF$_3$' means trifluoroborane, 'K$_2$CO$_3$' means potassium carbonate, 'Et$_3$N' means triethylamine, 'NH$_2$OH' means hydroxylamine, 'NaHCO$_3$' means carbonic acid monosodium salt, 'NaOAc' means sodium acetate 'Et$_2$O' means diethyl ether, 'PTSA' means p-toluenesulfonic acid, 'DMS' means dimethylsulfide, 'LiOH' means lithiumhydroxide, 'HCl' means hydrochloric acid, 'Pd$_2$(dba)$_3$' means tris[μ-[(1,2-η:4,5-η)-(1E,4E)-1,5-diphenyl-1,4-pentadien-3-one]]dipalladium, 'HBTU' means 1-[bis(dimethylamino)methylene]-1H-benzotriazoliumhexafluorophosphate (1-)3-oxide, 'NH₄HCO₃' means carbonic acid monoammonium salt, 'CHCl₃' means trichloromethane, 'HNO₃' means nitric acid, 'CH₃NH₂' means methanamine, 'NH₄OH' means ammonium hydroxide, 'DMSO' means dimethylsulfoxide, and 'NaBH₃CN' means sodium cyanoborohydride.

High-Performance Liquid Chromatography Purification Methods:

Purification Method A:

The product was purified by reversed phase high-performance liquid chromatography (Shandon Hyperprep® C18 BDS (Base Deactivated Silica) 8 μm, 250 g, I.D. 5 cm). A gradient with three mobile phases was applied (phase A: a 0.25% NH₄HCO₃ solution in water; phase B: CH₃OH; phase C: CH₃CN). The desired fractions were collected and worked-up.

A. Synthesis of the Intermediates

Example A.1

Preparation of

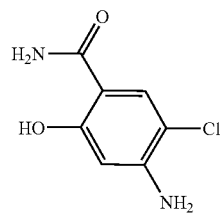

intermediate (1)

4'-Carbamoyl-2'-chloro-5'-hydroxyacetanilide (0.081 mol) and H₂SO₄ (15 ml) in methanol (150 ml) was stirred and refluxed for 1 hour. Methanol was evaporated (vacuum). Water (100 ml) was added. The precipitate was filtered off and dried (vacuum), yielding 15.0 g of intermediate (1).

Example A.2 a) Preparation of

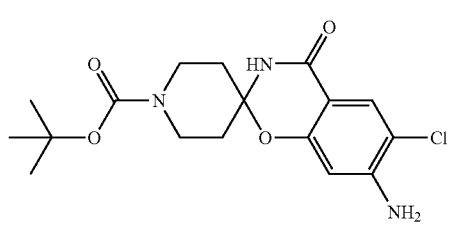

intermediate (2)

1,1-Dimethylethyl ester 4-oxo-1-piperidinecarboxylic acid (0.067 mol), intermediate (1) (0.08 mol) and pyrrolidine (0.0066 mol) in toluene (200 ml) was stirred and refluxed overnight. Toluene was evaporated. The precipitate was filtered off, washed 3 times with DIPE (200 ml) and dried, yielding 23.3 g of intermediate (2).

b) Preparation of

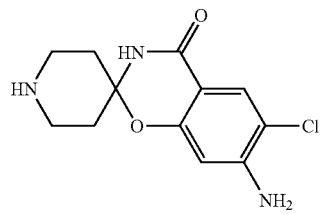

intermediate (3)

CF₃COOH/CH₂Cl₂ (100 ml; 50/50) was added slowly to a stirring mixture of intermediate (1) (0.0407 mol) in CH₂Cl₂ (50 ml) and stirred for 3 hours. The solvent was evaporated. The residue was crystallized from CH₃CN, the precipitate was filtered off and dried, yielding 11.84 g of intermediate (3).

c) Preparation of

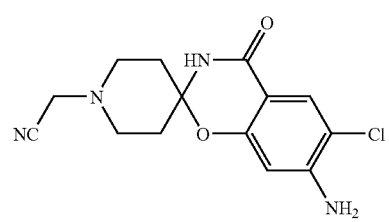

intermediate (4)

Intermediate (3) (0.031 mol), 2-chloroacetonitrile (0.046 mol) and DIPEA (0.155 mol) in CH₃CN (150 ml) was stirred and refluxed for 1 hour. CH₃CN was evaporated (vacuum). The residue was stirred in water (150 ml), the precipitate was filtered off, washed with DIPE and dried (vacuum), yielding 9.3 g of intermediate (4).

d) Preparation of

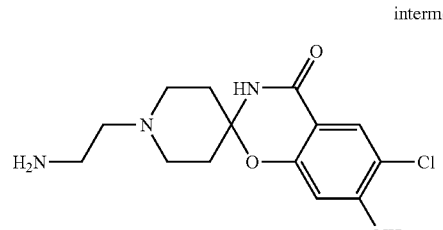

intermediate (5)

A mixture of intermediate (4) (0.03 mol) in NH₃/CH₃OH (250 ml) was hydrogenated at 14° C. with Raney Nickel (catalytic quantity) as a catalyst in the presence of a thiophene solution (1 ml). After uptake of hydrogen (2 equivalents; 1500 ml hydrogen), the catalyst was filtered off and the filtrate was evaporated. The residue was re-crystallized from CH₃CN and the precipitate was filtered off, yielding 6.6 g of intermediate (5).

Example A.3 a) Preparation of

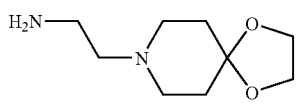

intermediate (6)

1,4-Dioxa-8-azaspiro[4.5]decane (2.1 mol) in toluene (4200 ml) was stirred at room temperature. DIPEA (2.3 mol) was added to the reaction mixture. 2-Chloro-acetonitrile (2.2 mol) was added slowly to the reaction mixture and then stirred for 2 hours at 80° C. The reaction mixture was cooled. Then the reaction mixture was washed 2 times with water (2000 ml). The separated organic layer's solvent was evaporated, yielding 175.3 g of residue. The 2 separated aqueous layers were combined and washed with CH₂Cl₂ (3000 ml). This separated organic layer was dried (Na₂SO₄), filtered and the solvent was evaporated (and co-evaporated with toluene), yielding another 100 g of residue. The residues were combined and dissolved in CH₃OH/NH₃ and then hydrogenated with Raney Nickel (catalytic quantity) as a catalyst. After uptake of hydrogen (2 equivalents), the mixture was filtered off and the filtrate was evaporated, yielding 242.1 g of intermediate (6).

b) Preparation of

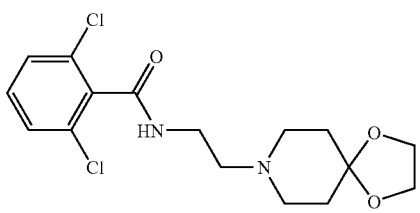

intermediate (7)

A mixture of intermediate (6) (1.04 mol) in DIPEA (5.23 mol) and CH₂Cl₂ (2000 ml) was stirred at 0° C. 2,6-Dichlorobenzoyl chloride (1.25 mol) was slowly added in drops in 50 minutes at 0° C. to the reaction mixture. The reaction mixture was allowed to warm up to room temperature. Water (2000 ml) was added to the reaction mixture. The separated organic layer was dried (Na₂SO₄), filtered and the solvent was evaporated. The residue was taken up in DIPE (1000 ml). The precipitate was filtered off and dried (vacuum), yielding 321 g of intermediate (7).

c) Preparation of

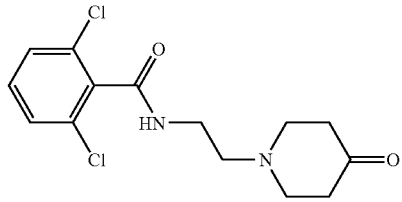

intermediate (8)

Intermediate (7) (0.180 mol) was dissolved in water (861 ml) and HCl (430 ml, 12 M). The reaction mixture was stirred at 80° C. for 3 hours. The reaction mixture was poured in 1 kg of ice and alkalized with Na₂CO₃. The aqueous mixture was extracted with CH₂Cl₂. The combined organic layers were dried, filtered and the solvent was evaporated. The residue was stirred for 2 hours in DIPE, then filtered off and dried in vacuum, yielding intermediate (8).

Example A.4 a) Preparation of

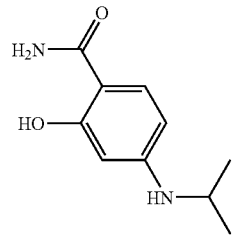

intermediate (9)

A mixture of 4-amino-5-chloro-2-hydroxy-benzamide (8 g, 0.043 mol) in methanol (250 ml) was hydrogenated with palladium-on-carbon (10%) (1 g) as a catalyst in the presence of KOAc (5 g). After uptake of hydrogen (1212 ml), the reaction mixture was used as such with 4-amino-2-hydroxy-benzamide (0.0480 mol) and 4-amino-2-hydroxybenzamide (0.048 mol) and the reaction mixture was hydrogenated further at 75° C. (100 atmosphere hydrogen pressure) in the presence of a thiophene solution (1 ml). After uptake of hydrogen, the catalyst was filtered off and the filtrate was evaporated. The residue was triturated under DIPE, filtered off and dried, yielding 4.8 g of intermediate (9).

b) Preparation of

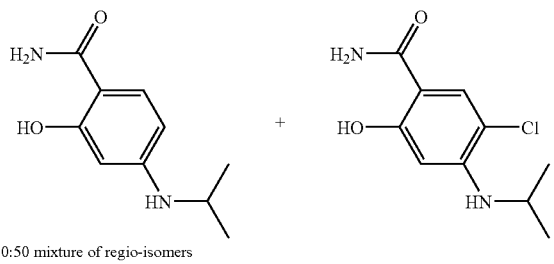

intermediate (10)

50:50 mixture of regio-isomers

A mixture of intermediate (9) (0.0051 mol) and 1-chloro-2,5-pyrrolidinedione (0.0051 mol) in CH₃CN was stirred for 3 hours at 50° C. The solvent was evaporated under reduced pressure. Water (50 ml) was added and the resulting white precipitate was filtered off and dried (vacuum, 50° C., 16 hours), yielding 0.850 g of intermediate (10) (1:1 mixture of two regio-isomers).

Example A.5

Preparation of

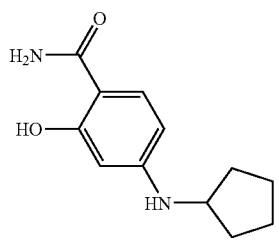

intermediate (11)

A mixture of 4-amino-2-hydroxybenzamide (0.039 mol) and cyclopentanone (0.039 mol) in methanol (100 ml) and THF (50 ml) was hydrogenated at 50° C. with palladium-on-carbon (10%) (1 g) as a catalyst in the presence of a thiophene solution (0.5 ml). After uptake of hydrogen (1 equivalent), the catalyst was filtered off and the filtrate was evaporated. The residue was triturated under DIPE, filtered off and dried, yielding 4.1 g of intermediate (11).

Intermediate (12) was prepared following the same procedure by replacing cyclopentanone with formaldehyde.

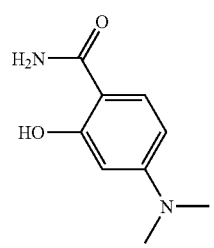

intermediate (12)

Example A.6

Preparation of

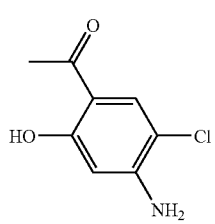

intermediate (13)

A mixture of 4'-acetyl-2'-chloro-5'-hydroxyacetanilide (0.014 mol) in $H_2SO_4$ (5 ml) and methanol (100 ml) was refluxed for 1 hour. Methanol was evaporated. The reaction mixture was neutralized to pH=7 with NaOH 1N aqueous solution. This mixture was extracted with $CH_2Cl_2$ (100 ml). The separated organic layer was washed with water (100 ml) and washed with brine (100 ml). The separated organic layer was dried ($MgSO_4$), filtered and the solvent was evaporated (vacuum), yielding 1.6 g of intermediate (13).

Example A.7

Preparation of

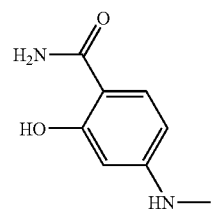

intermediate (14)

A mixture of 4-amino-2-hydroxybenzamide (0.0328 mol) and benzaldehyde (0.0328 mol) in methanol (100 ml) and THF (50 ml) was pre-hydrogenated at 50° C. with palladium-on-carbon (10%) (1 g) as a catalyst in the presence of a thiophene solution (0.5 ml). After uptake of hydrogen (1 equivalent), the reaction mixture was reacted further. Formaldehyde (1.5 g) was added to the crude reaction mixture and the whole was hydrogenated further (under 100 atmosphere of hydrogen) at 75° C. After uptake of hydrogen (1 equivalent), the catalyst was filtered off and the filtrate was evaporated. The residue was debenzylated reductively by hydrogenation in methanol (150 ml) with palladium-on-carbon (10%) (1 g) as a catalyst. After uptake of hydrogen (1 equivalent), the catalyst was filtered off and the filtrate was evaporated, yielding 3.7 g of intermediate (14).

Example A.8

Preparation of

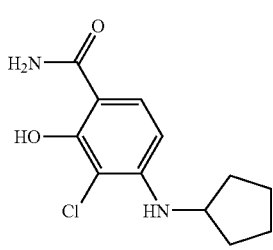

intermediate (15)

Intermediate (11) (0.0122 mol) was dissolved in DMF (20 ml). 1-Chloro-2,5-pyrrolidinedione (0.0122 mol) was added in one portion. The reaction mixture was stirred for 16 hours at 40° C. The solvent was evaporated under reduced pressure. Water was added to the residue. The precipitate was filtered off and dissolved in ethyl acetate. The organic solution was dried ($MgSO_4$), filtered and the solvent was evaporated. The residue was purified by column chromatography over silica gel (eluent: ethyl acetate/hexane 50/50 v/v). The product fractions were collected and the solvent was evaporated, yielding 2.5 g of intermediate (15).

Intermediate (16) was prepared following the same procedure but starting from intermediate (12).

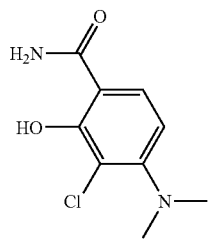

intermediate (16)

Example A.9

Preparation of

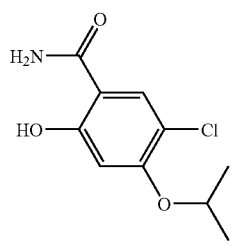

intermediate (17)

5-Chloro-2-hydroxy-4-(1-methylethoxy)benzoic acid methyl ester (0.0273 mol) was dissolved in $NH_3$ in dioxane (0.5N) (300 ml) and the resultant reaction mixture was stirred overnight at 100° C. (autoclave). The solvent was evaporated. The residue was dissolved in 7N $NH_3$/$CH_3OH$ and this solution was stirred at 100° C. in an autoclave overnight. The solvent was evaporated and the obtained residue was purified by column chromatography over silica gel (eluent: $CH_2Cl_2$/$CH_3OH$ 99/1). The product fractions were collected and the solvent was evaporated, yielding 5.14 g of intermediate (17) (mp.: 179.5° C.).

Intermediate (17) was prepared following the same procedure but starting from 2-hydroxy-4-isopropoxy-benzoic acid methyl ester.

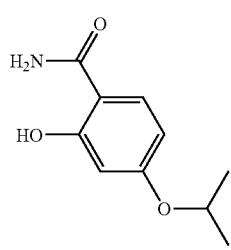

intermediate (18)

Example A.10 a) Preparation of intermediate (19)

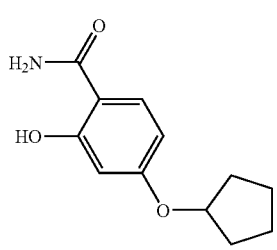

To a suspension of sodium hydride (0.0970 mol) in DMF (30 g), chilled in argon atmosphere with liquid nitrogen, was added 2,4-dihydroxybenzoic acid, methyl ester (0.0974 mol) in DMF (60 g) (the procedure was carried out in 500 ml flask due to hard foaming generated by hydrogen isolation). The reaction mixture was allowed to attain room temperature slowly with stirring by magnetic stirrer. After evolution of hydrogen ceased, the mixture was stirred for another 30 minutes. Then bromocyclo-pentane (0.1220 mol) was added and the mixture was heated at 100° C. for 2 hours. DMF was evaporated; $CH_2Cl_2$ (100 ml) was added to a residue; a precipitate was filtered off and washed with $CH_2Cl_2$ (2×10 ml). The combined $CH_2Cl_2$ solution was evaporated in vacuum. The raw product was dissolved in methanol (20 g) and the solution obtained was allowed to crystallize at −10° C. (in freezer) for 15 hours. The crystals was filtered off, washed with cold methanol (2×20 ml) and dried in vacuum, yielding 10.5 g of intermediate (19) (mp.: 42-43° C.).

b) Preparation of intermediate (20)

Intermediate (19) (0.0797 mol) was dissolved in $NH_3$ in $CH_3OH$ (7N) (300 ml) and the mixture was stirred in an autoclave at 125° C. for 18 hours. Then the mixture was cooled down to room temperature, concentrated and co-evaporated with methanol. The residue was purified by column chromatography (eluent: $CH_2Cl_2$/$CH_3OH$ 97/3). The product fractions were collected and the solvent was evaporated. The pure product fractions were collected and the solvent was evaporated, yielding product fraction A. The less pure fractions were further purified by flash chromatography (eluent: $CH_2Cl_2$/$CH_3OH$ 99/1). The product fractions were collected and the solvent was evaporated, yielding product fraction B. The impure product fractions (mixed fractions) were also collected and were further purified by column chromatography (eluent: $CH_2Cl_2$/$CH_3OH$ 99/1). The desired fractions were collected and the solvent was evaporated, yielding product fraction C. Product fractions A, B and C were combined, yielding 8.05 g of intermediate (20) (mp.: 146° C.).

Example A.11

Preparation of

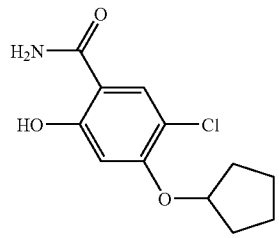

intermediate (21)

Intermediate (19) (0.0866 mol) was dissolved in CH$_3$CN (200 ml). 1-Chloro-2,5-pyrrolidinedione (0.0901 mol) was added. The reaction mixture was stirred and refluxed for ±16 hours. The solvent was evaporated. CH$_2$Cl$_2$ (300 ml) was added. The mixture was washed with water (200 ml), with a saturated aqueous NaHCO$_3$ solution (200 ml), then dried (Na$_2$SO$_4$), filtered and the solvent was evaporated. The residue was purified by column chromatography over silica gel (eluent: heptane/ethyl acetate from 98/2 to 97/3). The desired fractions were collected and the solvent was evaporated. The residue was co-evaporated with ethyl acetate, then with CH$_2$Cl$_2$. The residue was dissolved again in THF (110 ml) and methanol (11 ml). 1M NaOH (140 ml) was added to this solution and the mixture was heated to reflux temperature (85° C.) for 270 minutes. Then the reaction mixture was cooled down to room temperature and extracted with Et$_2$O (150 ml). The reaction mixture was acidified with 6N HCl (±25 ml) and was extracted with ethyl acetate (2×150 ml). The ethyl acetate layer was washed with brine and dried (Na$_2$SO$_4$). The filtrate's solvent was evaporated. The obtained residue was converted into the methyl ester. Therefore, the residue was dissolved in methanol and H$_2$SO$_4$ (0.792 ml) was added dropwise. The reaction mixture was stirred and refluxed for 3 hours. Then more H$_2$SO$_4$ (1 ml) was added and the mixture was stirred and refluxed for 1 week. The solvent was evaporated. A saturated aqueous NaHCO$_3$ solution was added carefully. The mixture was extracted with ethyl acetate (2×150 ml). The separated organic layer was washed with brine, dried (Na$_2$SO$_4$), filtered and the solvent was evaporated and co-evaporated with CH$_2$Cl$_2$. The residue was stirred in 7N NH$_3$ in methanol (300 ml) overnight at 100° C. in an autoclave. Then the solvent was evaporated and the residue was purified by flash column chromatography (eluent: CH$_2$Cl$_2$/CH$_3$OH). The desired fractions were collected and the solvent was evaporated. The residue was crystallized from 2-propanol (90 ml). The precipitate was filtered off and the filtrate was stored overnight at room temperature. A new precipitate was filtered off (Residue (I)) and the filtrate's solvent was evaporated (Residue (II)). Residues (I) and (II) were recombined, then recrystallized from 2-propanol. The precipitate was filtered off and was recrystallized from 2-propanol, then filtered off and dried, yielding 3.69 g of intermediate (21) (mp.: 181° C.).

Example A.12

Preparation of

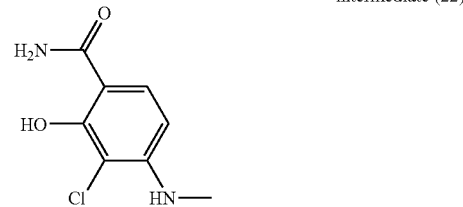

intermediate (22)

Intermediate (14) (0.0144 mol) was dissolved in DMF (20 ml). 1-Chloro-2,5-pyrrolidinedione (0.0144 mol) was added in one portion. The reaction mixture was stirred for 16 hours at 40° C. The solvent (DMF) was evaporated under reduced pressure. Water was added to the residue. The precipitate was filtered off and dissolved in ethyl acetate. The organic solution was dried (MgSO$_4$), filtered and the solvent was evaporated. The residue was purified by column chromatography over silica gel (eluent: ethyl acetate/hexane 50/50 v/v). The product fractions were collected and the solvent was evaporated, yielding 1.53 g of intermediate (22).

Example A.13

Preparation of

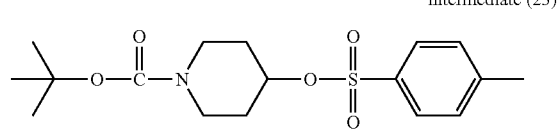

intermediate (23)

Triethylamine (14 ml) was added to a solution of 1,1-dimethylethyl 4-hydroxy-piperidine-1-carboxylate (0.0670 mol) in CH$_2$Cl$_2$ (300 ml). 4-Methylbenzene-sulfonyl chloride (0.0740 mol) was added slowly under nitrogen. The reaction mixture was stirred at room temperature for 2 hours. Water was added and the mixture was extracted, dried, filtered and the solvent was evaporated. The residue was dissolved in pyridine. 4-Methylbenzenesulfonyl chloride in pyridine was added at 0° C. The reaction mixture was stirred at room temperature overnight under nitrogen. The precipitate was filtered off and the solvent of the filtrate was evaporated. The residue (filtrate) was taken up in CH$_2$Cl$_2$ and extracted with water. The organic layer was dried, filtered and the solvent was evaporated. After co-evaporation with toluene the residue was taken up in heptane and the precipitate was filtered off, yielding intermediate (23).

Example A.14 a) Preparation of

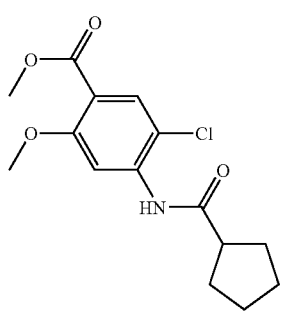

intermediate (24)

Reaction under nitrogen atmosphere. Sodium chloride (0.525 mol) was added to a solution of cyclopentanecarboxylic acid (0.105 mol) in $CH_2Cl_2$ (200 ml) while cooled on an ice-bath. This mixture was refluxed for 2 hours and the solvent was evaporated. The residue was dissolved in $CH_2Cl_2$ (150 ml) and 4-amino-5-chloro-2-methoxy-benzoic acid methyl ester (0.07 mol) and $Et_3N$ (19.6 ml, 0.140 mol) were added. The reaction mixture was stirred at room temperature for 1 hour. The solvent was evaporated and the residue was dissolved in $CH_2Cl_2$ (100 ml). The organic layer was washed with water (30 ml), saturated brine (30 ml) and then the organic layer was dried ($MgSO_4$), filtered and the solvent was evaporated. The residue was purified by column chromatography over silica gel (eluent: petroleum ether/$CH_2Cl_2$ from 2/1 till 0/1). The product fractions were collected and the solvent was evaporated, yielding 8 g of intermediate (24).

b) Preparation of

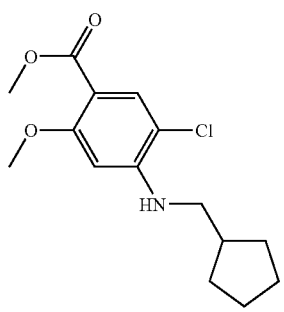

intermediate (25)

Reaction under nitrogen atmosphere. Intermediate (24) (0.026 mol) was dissolved in dry THF (150 ml). Borane/DMS (2.6 ml, 0.026 mol) was added to this solution and the mixture was stirred at room temperature for 1 hour and was subsequently refluxed for 12 hours. The mixture was cooled to room temperature and 1N HCl (50 ml) was added. The organic phase was separated and the aqueous layer was extracted with $CH_2Cl_2$ (2×100 ml). The combined organic layers were washed with water (100 ml), dried and evaporated. The residue was purified by column chromatography over silica gel (eluent: from petroleum ether/$CH_2Cl_2$ 4/1 till 100% $CH_2Cl_2$). The product fractions were collected and the solvent was evaporated, yielding 2.8 g of intermediate (25).

c) Preparation of

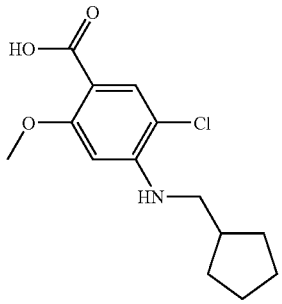

intermediate (26)

Intermediate (25) (0.0235 mol) was dissolved in dry THF (147 ml). LiOH/$H_2O$ (147 ml) was added to this solution and the reaction mixture was stirred for 24 hours at 50° C. Then the mixture was cooled to room temperature and the organic solvent was evaporated. The precipitate was filtered off and $CH_2Cl_2$ was added. The mixture was acidified with HCl (concentrated) until the precipitate was completely dissolved. The aqueous layer was extracted with $CH_2Cl_2$ (2×50 ml). The combined organic layers were dried, filtered and the solvent was evaporated. The residue was washed with diisopropylether, yielding 6.00 g of intermediate (26).

d) Preparation of

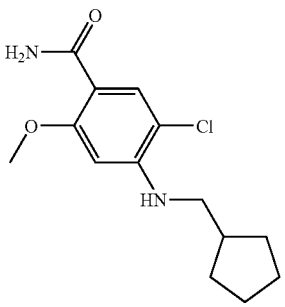

intermediate (27)

Reaction under nitrogen atmosphere. Intermediate (26) (0.0194 mol) was dissolved in dry $CH_2Cl_2$ (100 ml). 4-Methylmorpholine (0.0213 mol) was added to the solution and this mixture was cooled to 0° C. on an ice-bath. Then 2-methylpropyl chloro-formate (0.0388 mol) was added slowly and the reaction mixture was stirred for 30 minutes at 0° C. and then stirred at room temperature for 1 hour. $NH_3$ was introduced to the mixture at 0° C. over 30 minutes and then the $CH_2Cl_2$ was evaporated, yielding 10.6 g of intermediate (27).

e) Preparation of

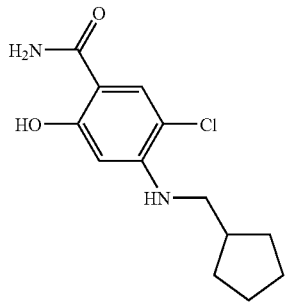
intermediate (28)

Intermediate (27) (0.0194 mol) was dissolved in 1-methyl-2-pyrrolidinone (100 ml). Piperazine (0.194 mol) was added to this solution and the reaction mixture was stirred for 16 hours at 140° C. Then 1-methyl-2-pyrrolidinone was evaporated and water was added to the residue. The precipitate was filtered off and was dissolved in ethyl acetate. This solution was dried, the drying agent was filtered off and the solvent was evaporated. The residue was washed with a mixture of petroleum ether and diisopropyl ether (1/1 v/v), yielding 3.8 g of intermediate (28).

Example A.15 a) Preparation of

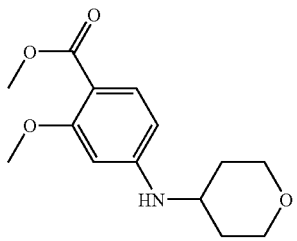
intermediate (29)

A solution of 4-bromo-2-methoxybenzoic acid methyl ester (0.1 mol) and tetrahydro-2H-pyran-4-amine (0.3 mol) in 1-methyl-2-pyrrolidinone (800 ml) was stirred at 40° C. $Cs_2CO_3$ (0.2 mol) was added. The reaction mixture was stirred for 5 minutes. $Pd_2(dba)_3$ (0.002 mol) and BINAP (0.003 mol) were added. The reaction solution was degassed by applying alternating nitrogen atmosphere and vacuum. The reaction mixture was stirred overnight at 110° C. The 1-methyl-2-pyrrolidinone solvent was evaporated. The residue was purified by high-performance liquid chromatography. The product fractions were collected and the solvent was evaporated, yielding 13 g of intermediate (29).

b) Preparation of

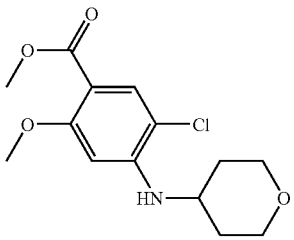
intermediate (30)

A solution of intermediate (29) (0.049 mol) and 1-chloro-2,5-pyrrolidinedione (0.044 mol) in $CH_3CN$ (150 ml) was stirred and refluxed at 100° C. for 3 hours. The solvent was evaporated. The residue was purified by column chromatography over silica gel (gradient elution; eluent: petroleum ether/ethyl acetate from 100/0 to 50/50). The product fractions were collected and the solvent was evaporated, yielding 7 g of intermediate (30).

c) Preparation of

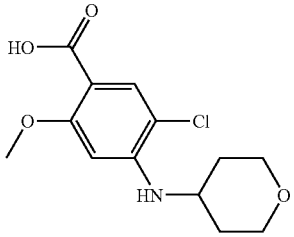
intermediate (31)

Intermediate (30) (0.0233 mol) was dissolved in THF (100 ml). $LiOH/H_2O$ (2N) (300 ml) was added. The reaction mixture was stirred overnight at 50° C. The solvent (THF) was evaporated. The pH was changed to pH=8. $CH_2Cl_2$ (250 ml) was added. The organic layer was separated, washed with water (2×), dried ($Na_2SO_4$), filtered and the solvent was evaporated under reduced pressure, yielding 6.58 g of intermediate (31).

d) Preparation of

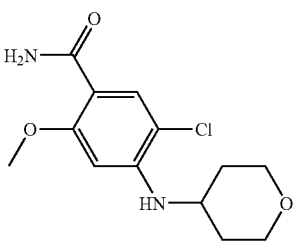
intermediate (32)

Intermediate (31) (0.0227 mol) was dissolved in CH$_2$Cl$_2$ (200 ml), protected under nitrogen gas. 4-Methylmorpholine (0.02497 mol) was added. The solution was stirred for several minutes. 2-Methylpropyl chloroformate (0.02497 mol) was added dropwise. The resultant reaction mixture was stirred for ±30 minutes at room temperature. NH$_3$ was introduced to the solution until all starting material was disappeared. The reaction mixture was stirred for half an hour. The solvent was evaporated. The residue was dried in vacuum, yielding 7 g of intermediate (32).

e) Preparation of

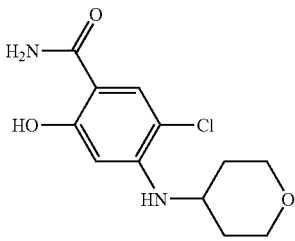

intermediate (33)

Intermediate (32) (0.021 mol) was dissolved in 1-methyl-2-pyrrolidinone (120 ml). Piperazine (0.21 mol) was added. The reaction mixture was stirred overnight at 140° C. The solvent was evaporated. The residue was purified by column chromatography over silica gel (eluent: petroleum ether/ethyl acetate gradient from 100/0 to 50/50). The product fractions were collected and the solvent was evaporated, yielding 4.5 g of intermediate (33).

Example A.16 a) Preparation of

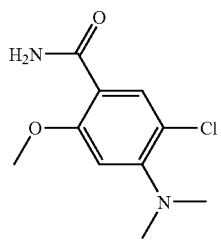

intermediate (34)

HBTU (0.012 mol) was added portion wise to a mixture of 5-chloro-4-(dimethyl-amino)-2-methoxybenzoic acid (0.010 mol) in DIPEA (2 ml) and DMF (20 ml) and then stirred for 1 hour at room temperature. The reaction mixture was cooled to −10° C. on an ice/EtOH bath. NH$_3$ in dioxane (0.5M) (40 ml) was added and the reaction mixture was allowed to warm up to room temperature. The reaction mixture was stirred at room temperature for 30 minutes. The solvent was evaporated. The residue was taken up in water (100 ml) and stirred for 30 minutes at room temperature. The precipitate was filtered off The residue was stirred in CH$_3$CN. The precipitate was filtered off and dried (vacuum), yielding 1.7 g of intermediate (34).

b) Preparation of

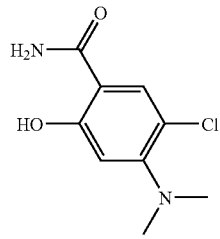

intermediate (35)

Intermediate (34) (0.0074 mol) and piperazine (0.0223 mol) in 1-methyl-2-pyrrolidinone (7 ml) was stirred for 16 hours at 140° C. The reaction mixture was cooled to room temperature and then poured in water (100 ml). The reaction mixture was acidified with HCl 1N aqueous solution. The precipitate was filtered off and dried (vacuum), yielding 1.1 g of intermediate (35).

Example A.17 a) Preparation of

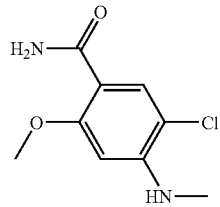

intermediate (36)

A mixture of 5-chloro-2-methoxy-4-(methylamino)benzoic acid (0.010 mol), HBTU (0.010 mol) and DIPEA (0.100 mol) in DMF (100 ml) was stirred for one hour at room temperature. The reaction mixture was cooled on an ice-ethanol bath and NH$_4$HCO$_3$ (0.050 mol) was added. The reaction mixture was stirred overnight at room temperature. The mixture was poured out into ice-water (±500 ml). The resulting precipitate was filtered off and dried, yielding 1.760 g of intermediate (36).

b) Preparation of

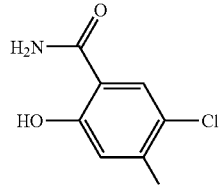

intermediate (37)

A mixture of intermediate (36) (0.010 mol) and piperazine (0.030 mol) in 1-methyl-2-pyrrolidinone (10 ml) was stirred for 20 hours at 140° C. in a closed reaction vial. The mixture was poured out into ice-water (180 ml), then neutralized with 1N HCl. This mixture was stirred over the weekend at room temperature. The precipitate was filtered off and dried, yielding 1.413 g of intermediate (37).

Example A.18 a) Preparation of

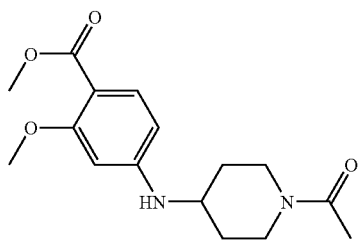

intermediate (38)

A mixture of 4-amino-2-methoxybenzoic acid methyl ester (0.138 mol) and 1-acetyl-4-piperidinone (0.14 mol) in methanol (300 ml) was hydrogenated at 100° C. (100 bar) for 32 hours with palladium-on-carbon (10%) (3 g) as a catalyst in the presence of a thiophene solution (1 ml). After uptake of hydrogen (1 equivalent), the catalyst was filtered off over dicalite and the filtrate's solvent was evaporated. The residue was purified by column chromatography over silica gel (eluent: first ethyl acetate 100% and then $CH_2Cl_2/CH_3OH$ 95/5). The product fractions were collected and the solvent was evaporated, yielding 41.5 g of intermediate (38).

b) Preparation of

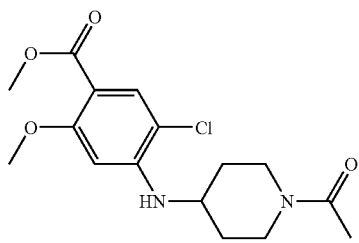

intermediate (39)

Intermediate (38) (0.13 mol) in DMF (500 ml) was warmed up to 60° C. 1-Chloro-2,5-pyrrolidinedione (0.13 mol) was added portion wise and the reaction mixture was stirred at 60° C. for 3 hours. The reaction mixture was cooled to room temperature and then the solvent was evaporated. The residue was stirred in water. This mixture was extracted 2 times with ethyl acetate. The separated organic layer's solvent was evaporated. The residue was re-crystallized from ethyl acetate, the precipitate was filtered off and dried (vacuum), yielding 16.5 g of intermediate (39).

c) Preparation of

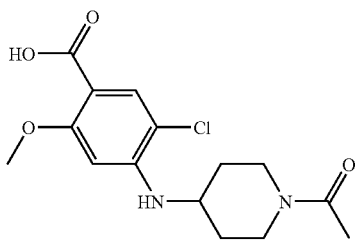

intermediate (40)

1N NaOH (aqueous solution) (0.094 mol) was added to a mixture of intermediate (39) (0.047 mol) in THF (188 ml) and water (94 ml) and was then stirred for 16 hours at room temperature. The reaction mixture was acidified until the pH=7. The solvent was evaporated and the residue was taken up in water. The precipitate was filtered off and then recrystallized from $CH_3CN$. This precipitate was filtered off and then dried (vacuum), yielding 7.3 g of intermediate (40).

d) Preparation of

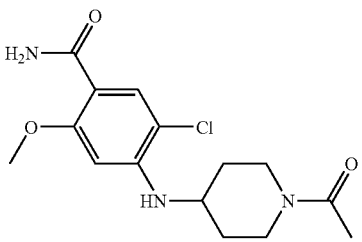

intermediate (41)

HBTU (0.0106 mol) was added to a mixture of intermediate (40) (0.00887 mol) in DIPEA (0.0106 mol) and DMF (20 ml) and stirred for 1 hour at room temperature. The reaction mixture was cooled to 0-5° C. on an ice bath. $NH_3$ in dioxane (0.5M) (35 ml) was added to the reaction mixture and the reaction mixture was allowed to warm up slowly to room temperature. This mixture was stirred for 1 hour at room temperature. The solvent was evaporated. The residue was taken up in water (100 ml). The precipitate was filtered off to obtain fraction A. The filtrate was re-extracted with ethyl acetate. This separated organic layer and fraction A were combined and the solvent was evaporated. The residue was purified by column chromatography over silica gel (eluent: $CH_2Cl_2/(CH_3OH/NH_3)$ from 100/0 to 97/3). The product fractions were collected and the solvent was evaporated. The residue was re-crystallized from $CH_3CN$, the precipitate was filtered off and dried (vacuum), yielding 1.9 g of intermediate (41).

e) Preparation of

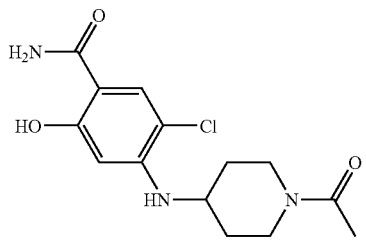

intermediate (42)

Intermediate (41) (0.0058 mol), piperazine (0.018 mol) and 1-methyl-2-pyrrolidinone (6 ml) was stirred for 16 hours at 140° C. The reaction mixture was cooled to room temperature and then poured out in water (100 ml). This mixture was acidified with HCl 1N aqueous solution. The precipitate was filtered off and dried (vacuum), yielding 1.5 g intermediate (42).

Example A.19 a) Preparation of

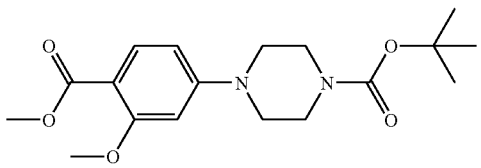

intermediate (43)

Reaction under nitrogen flow. 1-Methyl-2-pyrrolidinone (40 ml) was added to a mixture of 4-bromo-2-methoxybenzoic acid methyl ester (0.040 mol) and 1-(tert-butyloxycarbonyl)piperazine (0.048 mol). The mixture was stirred until complete dissolution. Then $Cs_2CO_3$ (0.06 mol) was added. The reaction mixture was heated to 40° C. Then $Pd_2(dba)_3$ (0.0004 mol) and 98% BINAP (0.0012 mol) were added. Then the reaction mixture was stirred vigorously for 16 hours at 110° C. The reaction mixture was cooled to room temperature and then poured out in water (200 ml). Then the reaction mixture was extracted with ethyl acetate (2 cycles). The solvent of the separated organic layer was evaporated. The residue was taken up in $CH_2Cl_2$. Then the mixture was dried, filtered and the $CH_2Cl_2$ was evaporated. The residue was purified by column chromatography over silica gel (eluent: $CH_2Cl_2/CH_3OH$ from 100/0 to 98/2). The product fractions were collected and the solvent was evaporated. The residue was recrystallized from DIPE. The precipitate was filtered off and dried (vacuum), yielding 8 g of intermediate (43).

b) Preparation of

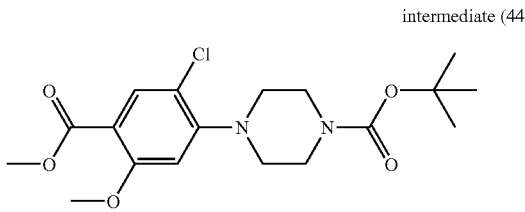

intermediate (44)

A mixture of intermediate (43) (0.0078 mol) and 1-chloro-2,5-pyrrolidinedione (0.0078 mol) in $CH_3CN$ (50 ml) was stirred for 16 hours at reflux. Then the reaction mixture was cooled to room temperature and the solvent was evaporated. The residue was washed with water and extracted with $CH_2Cl_2$. The solvent of the separated organic layer was evaporated. The residue was purified by high-performance liquid chromatography. The product fractions were collected and the solvent was evaporated. The residue was taken up in hexane. The precipitate was filtered off and dried (vacuum), yielding 1.8 g of intermediate (44).

c) Preparation of

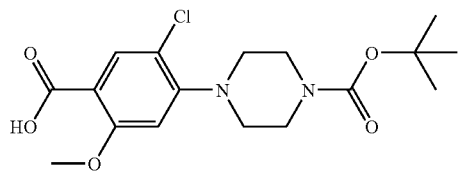

intermediate (45)

1N NaOH (aqueous solution) (0.00935 mol) was added to a mixture of intermediate (44) (0.00468 mol) in water (9 ml) and THF (18 ml). The reaction mixture was stirred for 16 hours at room temperature. Then solvent was evaporated. The residue was stirred in water (10 ml). The mixture was acidified with 1N HCl (aqueous solution) (9 ml). The precipitate was filtered off and taken up again in DIPE. Then the recrystallised precipitate was filtered off and dried (vacuum), yielding 1.5 g of intermediate (45).

d) Preparation of

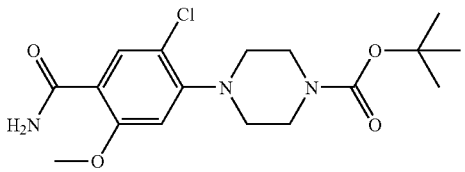

intermediate (46)

DIPEA (0.020 mol) was added to a mixture of intermediate (45) (0.0088 mol) and HBTU (0.010 mol) in DMF (50 ml), stirred at room temperature. The reaction mixture was stirred for one hour at room temperature. The reaction mixture was cooled on an ice-ethanol bath and $NH_3$ in dioxane (0.5M)

(0.020 mol) was added. The reaction mixture was stirred for 1 hour while cooling on the ice-ethanol bath, then for 3 hours at room temperature. The solvent was evaporated. The residue was stirred overnight in water/CH₃CN, then the resulting precipitate was filtered off and dried, yielding 3.27 g of intermediate (46).

e) Preparation of

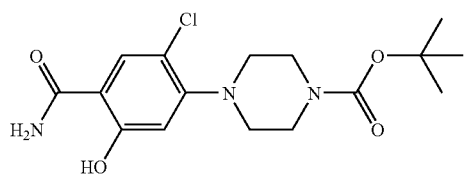

intermediate (47)

A mixture of intermediate (46) (0.003 mol) and piperazine (0.009 mol) in 1-methyl-2-pyrrolidinone (3 ml) was stirred for 16 hours at 140° C. in a closed reaction vial. The mixture was poured out into water (10 ml), then neutralized with acetic acid. This mixture was stirred over the weekend at room temperature. The precipitate was filtered off and dried, yielding 0.825 g of intermediate (47).

Example A.20

Preparation of

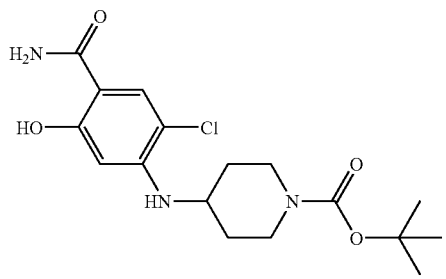

intermediate (48)

A mixture of 4-[[4-(aminocarbonyl)-2-chloro-5-methoxyphenyl]amino]-1-piperidine-carboxylic acid 1,1-dimethylethyl ester (0.021 mol) and piperazine (0.063 mol) in 1-methyl-2-pyrrolidinone (21 ml) was stirred for 16 hours at 140° C. The reaction mixture was cooled to room temperature, then poured out into ice-water (300 ml). The mixture was acidified to pH=±4 with acetic acid. The resulting precipitate was filtered off, washed with water, then taken up into CH₂Cl₂. The separated organic layer was dried (MgSO₄), filtered and the solvent evaporated. The residue was stirred in DIPE, filtered off and dried in vacuum, yielding 7.3 g of intermediate (48).

Example A.21 a) Preparation of

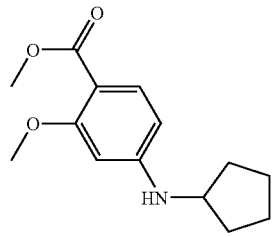

intermediate (49)

A mixture of 4-amino-2-methoxybenzoic acid methyl ester (0.29 mol) and cyclopentanone (52 ml) in toluene (400 ml) was hydrogenated for 20 hours at 130° C. (50 kg hydrogen pressure) with palladium-on-carbon (10%) (3 g) as a catalyst in the presence of a 4% thiophene solution (2 ml). After uptake of hydrogen (1 equivalent), the catalyst was filtered off over dicalite and the filtrate was evaporated, yielding 72 g of intermediate (49).

b) Preparation of

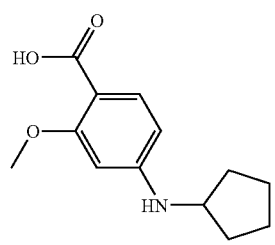

intermediate (50)

A solution of intermediate (49) (0.29 mol) and NaOH (1.5 mol) in water (1000 ml) was stirred and refluxed for 2 hours. The reaction solution was cooled and the resulting precipitate was filtered off and recrystallized from 2-propanol. The precipitate was filtered off and dried, yielding 51.7 g of intermediate (50).

c) Preparation of

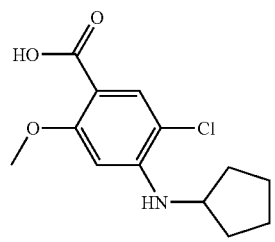

intermediate (51)

1-Chloro-2,5-pyrrolidinedione (0.00935 mol) was added to a mixture of intermediate (50) (0.00850 mol) in DMF (40 ml) and this reaction mixture was stirred for 16 hours at room temperature. The reaction mixture was poured out into water (300 ml) and the reaction mixture was stirred for 3 hours at room temperature. The precipitate was filtered off, washed with water, stirred in DIPE, filtered off and dried (vacuum). The obtained fraction was recrystallized from DIPE/CH₃CN. The precipitate was filtered off and dried (vacuum), yielding 1.0 g of intermediate (51).

d) Preparation of

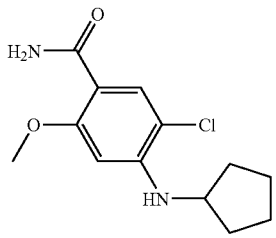

intermediate (52)

DIPEA (0.050 mol) was added to a mixture of intermediate (51) (0.035 mol) in DMF (p.a.) (150 ml). HBTU (0.035 mol) was added portion wise to the reaction mixture and was stirred for 1 hour at room temperature. The reaction mixture was cooled on an ice/EtOH bath. NH₃ in dioxane (0.5M) (100 ml) was added and stirred for 1 hour on the ice/EtOH bath. The reaction mixture was stirred another 12 hours at room temperature. The solvent was evaporated. The residue was stirred in ice water/some CH₃CN. The precipitate was filtered off and dried, yielding 11.56 g of intermediate (52).

e) Preparation of

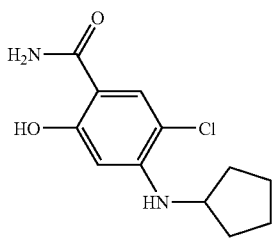

intermediate (53)

A mixture of intermediate (52) (0.010 mol) and piperazine (0.030 mol) in 1-methyl-2-pyrrolidinone (10 ml) was stirred for 16 hours at 140° C. The reaction mixture was poured out in water and then neutralized to pH=7 with acetic acid. The mixture was stirred over the weekend at room temperature. The precipitate was filtered off and dried, yielding 1.960 g of intermediate (53).

Example A.22 a) Preparation of

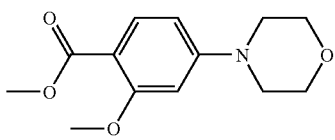

intermediate (54)

Reaction under nitrogen flow. 1-Methyl-2-pyrrolidinone (32 ml) was added to a mixture of 4-bromo-2-methoxybenzoic acid methyl ester (98%) (0.032 mol) and morpholine (0.038 mol). The mixture was stirred until complete dissolution. Then Cs₂CO₃ (0.048 mol) was added. The reaction mixture was heated to 40° C. Then Pd₂(dba)₃ (0.00032 mol) and BINAP (98%) (0.00096 mol) were added. Then the reaction mixture was stirred for 16 hours at 110° C. The reaction mixture was cooled to room temperature and then poured out in water (200 ml). Then the reaction mixture was extracted with ethyl acetate (2 cycles). The solvent of the separated organic layer was evaporated. The residue was taken up in CH₂Cl₂, dried, filtered and evaporated. The residue was purified by column chromatography over silica gel (eluent: CH₂Cl₂/CH₃OH from 100/0 to 98/2). The product fractions were collected and the solvent was evaporated. The residue was crystallized from DIPE. The precipitate was filtered off and dried (vacuum), yielding 3.8 g of intermediate (54).

b) Preparation of

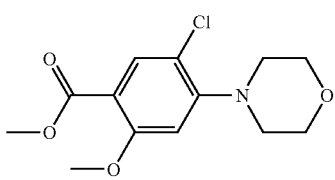

intermediate (55)

1-Chloro-2,5-pyrrolidinedione (0.014 mol) was added to a mixture of intermediate (54) (0.014 mol) in CH₃CN (100 ml). The reaction mixture was stirred for 16 hours at 40° C. Then the solvent was evaporated. The residue was crystallized from DIPE. The precipitate was filtered off and dried, yielding 2.6 g of intermediate (55).

c) Preparation of

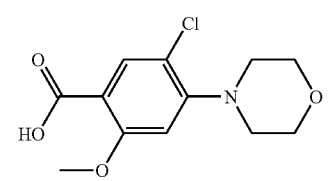

intermediate (56)

1N NaOH (aq. soln.) (0.0182 mol) was added to a mixture of intermediate (55) (0.0091 mol) in water (18 ml) and THF (36 ml). The reaction mixture was stirred for 16 hours at room temperature. Then solvent was evaporated. The residue was stirred in water (40 ml). The mixture was neutralized with 1N HCl (aqueous solution) (9 ml). The precipitate was filtered off and washed with water. Then the precipitate was dried (vacuum), yielding 2.3 g of intermediate (56).

d) Preparation of

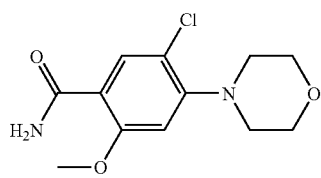

intermediate (57)

Reaction under nitrogen flow. HBTU (0.024 mol) was added to a mixture of intermediate (56) (0.020 mol) and DIPEA (0.026 mol) in DMF (100 ml) and stirred at room temperature for 1 hour. The reaction mixture was then cooled on an ice bath to 5° C. NH$_3$ in dioxane (0.5M) (0.040 mol) was added drop wise to the reaction mixture and then stirred for 2 hours at room temperature. The solvent was evaporated and the residue was taken up in ethyl acetate. The mixture was washed with water. The separated organic layer's solvent was evaporated. This residue was stirred in CH$_3$CN, the precipitate was filtered off and dried, yielding 5.4 g of intermediate (57).

e) Preparation of

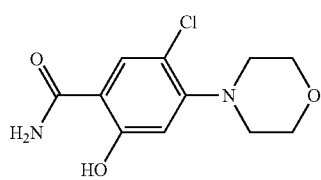

intermediate (58)

A mixture of intermediate (57) (0.01 mol) and piperazine (0.03 mol) in 1-methyl-2-pyrrolidinone (10 ml) was stirred for 16 hours at 140° C. The reaction mixture was cooled to room temperature and then poured out in water (100 ml). The reaction mixture was acidified with 1N HCl (aqueous solution) until a pH=6. The precipitate was filtered off and the filter residue was stirred in DIPE. This precipitate was filtered off and dried (vacuum), yielding 1.4 g of intermediate (58).

Example A.23 a) Preparation of

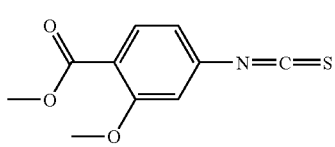

intermediate (59)

4-Amino-2-methoxybenzoic acid methyl ester (0.3 mol) was dissolved in stirred CHCl$_3$ (1000 ml), while heating. The mixture was cooled to ±35° C. Thiophosgene (0.39 mol) was added dropwise and the resultant reaction mixture was heated slowly to reflux temperature, then stirred and refluxed overnight. The reaction mixture was cooled, then poured out into ice-water. The organic layer was separated, washed three times with water, dried, filtered and the solvent evaporated. The residue was purified by vacuum distillation (bp at 0.2 mm Hg: 138° C.), yielding 56.5 g of intermediate (59).

b) Preparation of

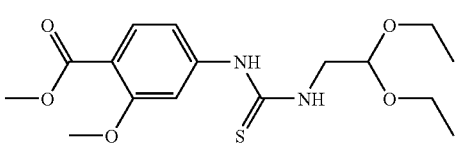

intermediate (60)

2,2-Diethoxyethanamine (0.24 mol) was dissolved in EtOH (250 ml). Intermediate (59) (0.24 mol) was added (exothermic temperature rise to ±60° C.). Precipitation started. The reaction mixture was stirred overnight allowing to cool to room temperature. The solvent was evaporated, yielding ±80 g of intermediate (60).

c) Preparation of

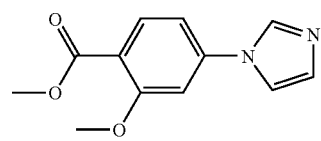

intermediate (61)

10% HCl (480 ml) was added to intermediate (60) (0.24 mol). The reaction mixture was warmed (up to ±90° C.). A solid formed. Water (300 ml) was added at ±90° C. The mixture was allowed to cool slowly to room temperature. The resulting precipitate was filtered off, washed with water, with petroleum ether, and dried. One part of this fraction (I) was reacted again in 10% HCl (480 ml). The reaction mixture was stirred and refluxed for 45 minutes, then cooled on an ice-bath and the resulting precipitate was filtered off, washed with a small amount of water then with petroleum ether and dried, yielding fraction (Ia). The other part of fraction (I) was reacted again in 10% HCl (480 ml). The reaction mixture was stirred and refluxed for 45 minutes, then cooled on an ice-bath and the resulting precipitate was filtered off, washed with a small amount of water then with petroleum ether, and dried, yielding fraction (Ib). Both product fractions (Ia) and (Ib) were combined, yielding 50.7 g of intermediate (61).

d) Preparation of

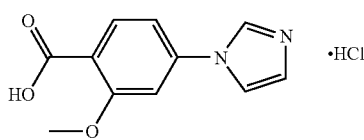

intermediate (62)

·HCl

HNO₃ (53.13 ml) was added to water (127.8 ml). NaNO₂ (0.42 g) was added (exothermic temperature rise to ±35° C.). At 30-35° C., intermediate (61) (0.106 mol) was added portionwise allowing the temperature to be kept in between 30° C. and 35° C. (exothermic; vapours, precipitation onset). Upon completion of addition of intermediate (61), the reaction mixture was heated slowly to 45° C. The reaction mixture was stirred for 15 minutes at 45° C., then it was cooled to room temperature and the resulting precipitate was filtered off, washed with a small amount of water, then taken up into a small amount of water. The mixture was alkalized until complete dissolution resulted. Water was added (when needed). The mixture was acidified with HCl and the resulting precipitate was filtered off and dried, yielding 18.5 g of intermediate (62).

e) Preparation of

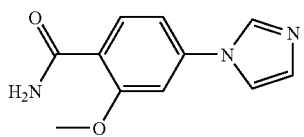

intermediate (63)

A mixture of intermediate (62) (0.014 mol) and DIPEA (0.031 mol) in DMF (70 ml) was stirred at room temperature. HBTU (0.016 mol) was added. The reaction mixture was stirred for one hour at room temperature, then cooled to ±5° C. on an ice-bath, and NH₃ in dioxane (0.5M) (56 ml) was added dropwise. The reaction mixture was stirred for 30 minutes at ±5° C. The mixture was allowed to warm to room temperature, then was stirred at room temperature for 2 hours. The solvent was evaporated. The residue was taken up into water. The resulting precipitate was filtered off, washed with water, stirred in CH₃CN, filtered off and dried (vacuum), yielding 2.9 g of intermediate (63).

f) Preparation of

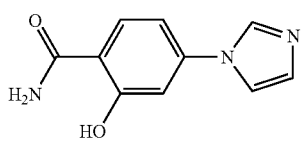

intermediate (64)

A mixture of intermediate (63) (0.013 mol) and piperazine (0.040 mol) in 1-methyl-2-pyrrolidinone (13 ml) was stirred for 16 hours at 140° C., then cooled to room temperature, poured into water (100 ml), then acidified with 1N HCl to pH of about 4. The resulting precipitate was filtered off, washed with water and dried (vacuum), yielding 1.6 g of intermediate (64).

Example A.24 a) Preparation of

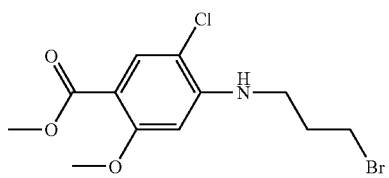

intermediate (65)

A mixture of 4-amino-5-chloro-2-methoxybenzoic acid methyl ester (0.020 mol) in 1,3-dibromopropane (40 ml) and DIPEA (6.6 ml) was stirred for 2 hours at 140° C. The reaction mixture was diluted with CH₂Cl₂ and then washed with water. The separated organic layer was dried (MgSO₄), filtered and the solvent was evaporated. The residue was purified by column chromatography over silica gel (eluent: CH₂Cl₂/CH₃OH from 100/0 to 99/1). The product fractions were collected and the solvent was evaporated. The residue was stirred in DIPE. The precipitate was filtered off and dried, yielding 3.770 g of intermediate (65).

b) Preparation of

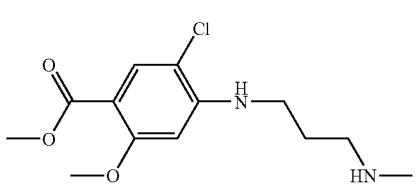

intermediate (66)

A mixture of intermediate (65) (0.020 mol) in CH₃NH₂ in methanol (2M) (60 ml) was stirred for 24 hours at 50° C. in a sealed vial. The reaction mixture's solvent was evaporated. The residue was purified by high-performance liquid chromatography (standard gradient elution with NH₄HCO₃ buffer). The product fractions were collected and the solvent was evaporated, yielding 5 g of intermediate (66).

c) Preparation of

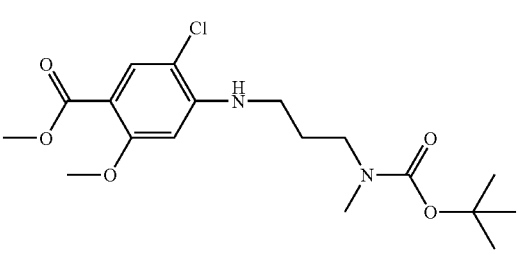

intermediate (67)

Di-tert-butyl dicarbonate (0.020 mol) in $CH_2Cl_2$ (p.a.) (20 ml) was added drop by drop to a mixture of intermediate (66) (0.0175 mol) and DIPEA (0.020 mol) in $CH_2Cl_2$ (80 ml) and stirred at room temperature. The reaction mixture was washed twice with ice water. The separated organic layer was dried ($MgSO_4$), filtered and the solvent was evaporated, yielding 7.2 g of intermediate (67).

d) Preparation of

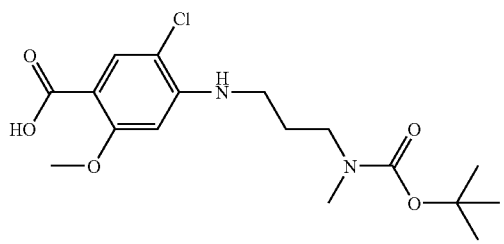

intermediate (68)

A mixture of intermediate (67) (0.0175 mol) and $LiOH.H_2O$ (0.035 mol) in water (50 ml) and dioxane (150 ml) was stirred for 2 hours at 50° C. and then overnight at room temperature. The reaction mixture was stirred another 4 hours at 50° C. and then overnight at room temperature. The solvent was evaporated. The residue was taken up in ice water and then neutralized with 1N HCl (aqueous solution) (135 ml). The precipitate was filtered off and dried, yielding 5.53 g of intermediate (68).

e) Preparation of

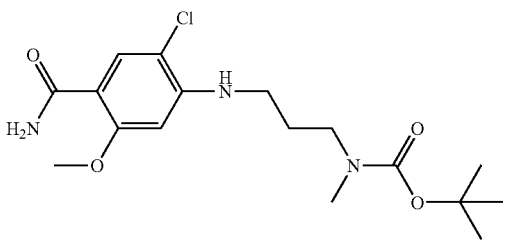

intermediate (69)

HBTU (0.015 mol) was added in portions to a stirring mixture of intermediate (68) (0.0147 mol) and DIPEA (0.030 ml) in DMF (100 ml) and stirred for 1 hour at room temperature. The reaction mixture was cooled on an EtOH/ice bath. $NH_3$ in dioxane (0.5M) (0.030 mol) was added in portions of 10 ml to the reaction mixture and stirred for 2 hours on an ice bath. Then the reaction mixture was stirred overnight at room temperature. The solvent was evaporated. The residue was stirred in ice water with some $CH_3CN$. The precipitate was filtered off and dried, yielding 5.3 g of intermediate (69).

f) Preparation of

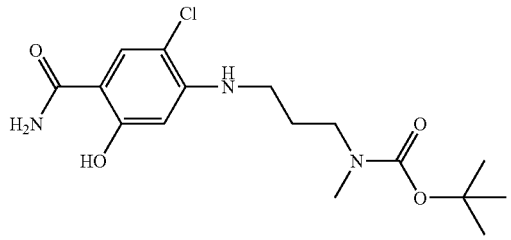

intermediate (70)

A mixture of intermediate (69) (0.003 mol) and piperazine (0.009 mol) in 1-methyl-2-pyrrolidinone (3 ml) was stirred for 16 hours at 140° C. The reaction mixture was poured out in water and then neutralized with 1N HCl aqueous solution and acetic acid. This mixture was extracted with $CH_2Cl_2$. The separated aqueous layer's solvent was evaporated. The residue was purified by column chromatography over silica gel (eluent: hexane/ethyl acetate from 90/10 to 50/50). The product fractions were collected and the solvent was evaporated, yielding 0.8 g of intermediate (70).

Example A.25 a) Preparation of

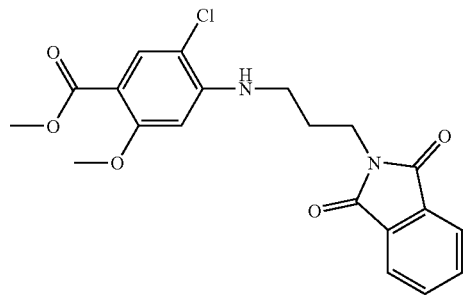

intermediate (71)

A mixture of 4-amino-5-chloro-2-methoxybenzoic acid methyl ester (0.1 mol), 2-(3-bromopropyl)-1H-isoindole-1,3 (2H)-dione (0.1 mol) and potassium iodide (catalytic quantity) in DIPEA (16.5 ml) was stirred for 2 hours at 130° C. The reaction mixture was stirred overnight at room temperature. 2-(3-bromopropyl)-1H-isoindole-1,3(2H)-dione (0.056 mol) and DIPEA (10 ml) were added to the reaction mixture again and stirred for 4 hours at 130° C. The reaction mixture was poured out in water and then stirred in water (200 ml) and $CH_3CN$ (200 ml). The precipitate was filtered off and dried, yielding 26.1 g of intermediate (71).

b) Preparation of

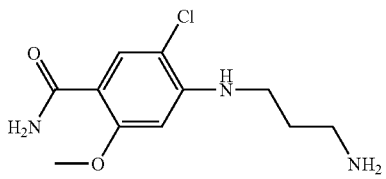

intermediate (72)

A mixture of intermediate (71) (0.027 mol) in NH₄OH (110 ml) was stirred for 2 hours at 125° C. in a micro wave. The solvent was evaporated. The residue was stirred in boiling CH₃OH/CH₃CN and then stirred overnight. The precipitate was filtered off and dried, yielding 8.17 g of intermediate (72).

c) Preparation of

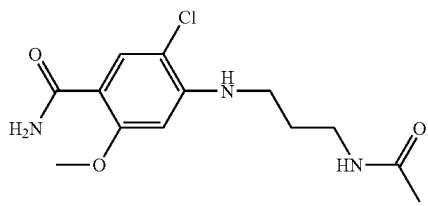

intermediate (73)

A mixture of intermediate (72) (0.020 mol) in acetyl acetate (40 ml) and CH₂Cl₂ (6.6 ml) was stirred for 2 hours at 140° C. The reaction mixture was diluted with CH₂Cl₂ and then washed with water. The separated organic layer was dried (MgSO₄), filtered and the solvent was evaporated. The residue was purified by column chromatography over silica gel (eluent: CH₂Cl₂/CH₃OH from 100/0 to 99/1). The product fractions were collected and the solvent was evaporated. The residue was stirred in DIPE. The precipitate was filtered off and dried, yielding 3.76 g of intermediate (73).

d) Preparation of

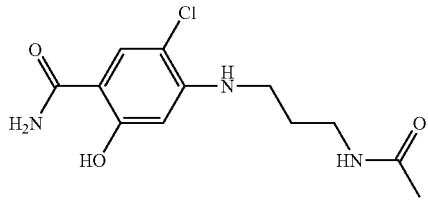

intermediate (74)

A mixture of intermediate (73) (0.013 mol) and piperazine (0.039 mol) in 1-methyl-2-pyrrolidinone (13 ml) was stirred for 20 hours at 140° C. Some more piperazine (0.0395 mol) was added to the reaction mixture and stirred for 24 hours at 140° C. The reaction mixture was cooled and then poured out in ice water (200 ml). The reaction mixture was filtered and the residue was discarded. The filtrate was neutralized with acetic acid. This precipitate was filtered off and dried, yielding 2.42 g of intermediate (74).

Example A.26 a) Preparation of

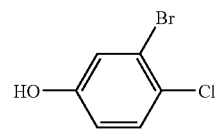

intermediate (75)

BBr₃ (50 ml) was added slowly in drops over 15 minutes to a solution of 2-bromo-1-chloro-4-methoxybenzene (0.448 mol) in CH₂Cl₂ (600 ml), stirred at −20° C. The resultant reaction mixture was stirred for 20 minutes at −20° C., then it was warmed to room temperature and stirred for one hour at room temperature, yielding 85 g of intermediate (75).

b) Preparation of

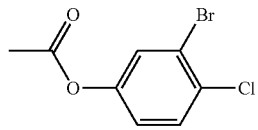

intermediate (76)

Acetyl chloride (0.036 mol) was added slowly to a solution of intermediate (75) (0.024 mol) and Et₃N (0.024 mol) in dry CH₂Cl₂ (60 ml). The resultant reaction mixture was stirred and refluxed for 12 hours, then cooled to room temperature, washed with a 2.5M aqueous NaOH solution, then with a 2.5M aqueous HCl solution. The organic layer was separated, dried (Na₂SO₄), filtered and the solvent was evaporated, yielding 4.9 g of intermediate (76).

c) Preparation of

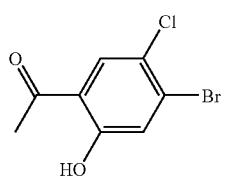

intermediate (77)

A flask was charged with intermediate (76) (0.24 mol) and acetic acid-boron trifluoride complex (2:1) (320 ml). The reaction solution was stirred and refluxed for 3 hours, then cooled to room temperature. The mixture (containing a precipitate) was partitioned between CH₂Cl₂ and water. The aqueous layer was extracted twice with CH₂Cl₂. The organic layers were combined, washed with water, then purified by preparative thin-layer chromatography. The product fractions were collected and the solvent was evaporated, yielding 33 g of intermediate (77).

d) Preparation of

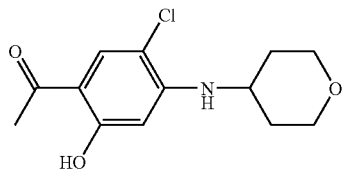

intermediate (78)

A flask was charged with intermediate (77) (0.008 mol), Pd$_2$(dba)$_3$ (0.366 g), BINAP (0.398 g) and Cs$_2$CO$_3$ (0.012 mol). Then, tetrahydro-2H-pyran-4-amine (0.012 mol) was added. The mixture was dissolved in DMF. The reaction solution was stirred for 13 hours at 120° C. The mixture was diluted with ethyl acetate (3×). The organic phase was washed with brine (2×). The combined organic layers were dried, filtered and the solvent evaporated in vacuum. The residue was purified by preparative high-performance liquid chromatography. The product fractions were alkalized (pH 8-9) by adding solid NaHCO$_3$. Sodium chloride was added. The aqueous phase was washed with ethyl acetate (2×). The combined organic layers were washed with water (2×), dried (Na$_2$SO$_4$), filtered and the solvent was evaporated. The residue was dried under high-vacuum, yielding 2.16 g of intermediate (78).

Example A.27

Preparation of

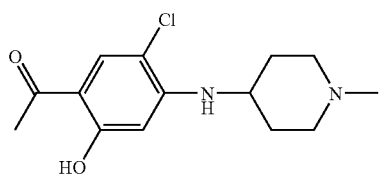

intermediate (79)

A flask was charged with intermediate (77) (0.012 mol), Pd$_2$(dba)$_3$ (0.549 g), BINAP (0.597 g) and Cs$_2$CO$_3$ (0.018 mol). Then, 1-methylpiperazine (0.018 mol) was added. The mixture was dissolved in DMF. The reaction solution was stirred for 13 hours at 120° C. The mixture was diluted with ethyl acetate (3×). The organic phase was washed with brine (3×). The aqueous phase was washed twice with ethyl acetate. The combined organic layers were dried, filtered and the solvent evaporated in vacuum. The residue was purified by column chromatography, then by preparative high-performance liquid chromatography. The organic mixture of the purification was saturated with sodium chloride. The aqueous phase was washed with 1N NaOH and with ethyl acetate (2×). The organic layer was separated, washed with water, dried, filtered and the solvent evaporated in vacuum. The residue was dried under high-vacuum, yielding 1 g of intermediate (79).

Example A.28

Preparation of

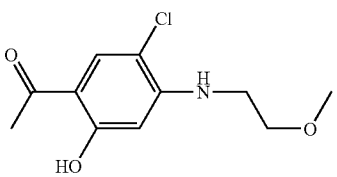

intermediate (80)

A flask was charged with intermediate (77) (0.012 mol), Pd$_2$(dba)$_3$ (0.549 g), BINAP (0.597 g) and Cs$_2$CO$_3$ (0.018 mol). Then, 2-methoxyethanamine (0.018 mol) was added. The mixture was dissolved in DMF. The reaction solution was stirred for 13 hours at 120° C. The mixture was diluted with ethyl acetate (3×). The organic phase was washed with brine (3×). The aqueous phase was washed twice with ethyl acetate. The combined organic layers were dried, filtered and the solvent evaporated in vacuum. The residue was purified by column chromatography, then by preparative high-performance liquid chromatography. The organic mixture of the purification was saturated with sodium chloride. The aqueous phase was washed with 1N NaOH and with ethyl acetate (2×). The organic layer was separated, washed with water, dried, filtered and the solvent evaporated in vacuum. The residue was dried under high-vacuum, yielding 0.600 g of intermediate (80).

Example A.29 a) Preparation of

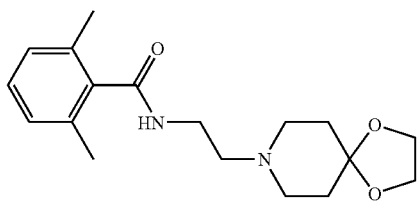

intermediate (81)

2,6-Dimethylbenzoic acid (0.0666 mol) was dissolved in dry CH$_2$Cl$_2$ (150 ml). A drop of DMF was added. Thionyl chloride (0.33 mol) was added in drops under nitrogen atmosphere at room temperature. The reaction mixture was stirred and refluxed for one hour. The solvent was evaporated under reduced pressure. The residue was dried (under oil pump vacuum), to give the intermediate acid chloride, which was dissolved in dry CH$_2$Cl$_2$ (30 ml), to give solution (I). Solution (I) was added to a solution of 1,4-dioxa-8-azaspiro[4.5]decane-8-ethanamine (0.0733 mol) and Et$_3$N (0.0666 mol) in dry CH$_2$Cl$_2$ (150 ml). The reaction mixture was stirred and refluxed for 90 minutes. The reaction mixture was cooled, washed with a saturated aqueous NaHCO$_3$ solution (30 ml), washed with water (30 ml), dried (Na$_2$SO$_4$), filtered and the solvent was evaporated under reduced pressure, yielding 23 g of intermediate (81).

b) Preparation of intermediate (82)

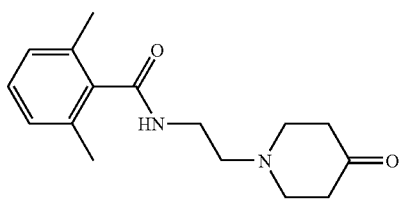

A mixture of intermediate (81) (0.066 mol) and HCl (80 ml) in water (160 ml) was stirred and refluxed for 3 hours. The mixture was poured out into ice. This mixture was alkalized to pH=9 with $Na_2CO_3$, then extracted with $CH_2Cl_2$. The organic layer was filtered out and treated under reduced pressure. The residue was dried in vacuum, yielding 17.20 g of intermediate (82).

Example A.30

Preparation of intermediate (83)

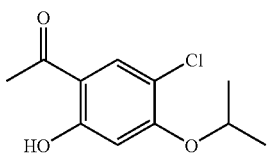

A solution of 1-(5-chloro-2,4-dihydroxyphenyl)ethanone (0.0320 mol), $K_2CO_3$ (8.87 g) and sodium iodide (0.24 g) in DMF (60 ml) was stirred. 2-Bromopropane (0.0320 mol) was added. The reaction mixture was stirred at 60° C. for 12 hours. The solvent was evaporated. The residue was dissolved in $CH_2Cl_2$, washed with water. The organic layer was evaporated. The residue was purified by column chromatography (eluent; $CH_2Cl_2$/heptane 98/2). The product fractions were collected, the solvent was evaporated, yielding 0.55 g of intermediate (83).

Example A.31

Preparation of intermediate (84)

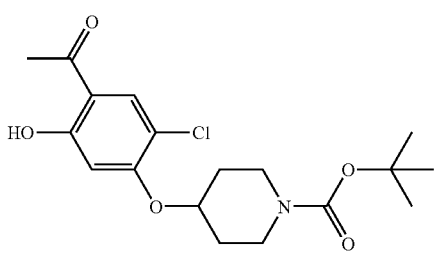

1-(5-Chloro-2,4-dihydroxyphenyl)ethanone (0.054 mol), intermediate (23) (0.067 mol) and $NaHCO_3$ (9 g) were dissolved in dry $CH_2Cl_2$. The solvent was evaporated. The reaction mixture was heated for 8 hours at 120° C., then cooled to room temperature and diluted with $CH_2Cl_2$. The organic mixture was washed with water. The separated organic layer was dried), filtered and the solvent was evaporated, yielding 14.6 g of intermediate (84).

Example A.32 a) Preparation of intermediate (85)

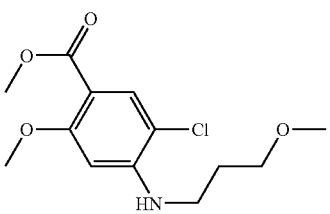

A mixture of 4-amino-5-chloro-2-methoxybenzoic acid methyl ester (0.069 mol), 1-bromo-3-methoxypropane (0.088 mol) and DIPEA (0.069 mol) was stirred for 2 hours at 150° C. Then the solution was cooled to room temperature and $CH_2Cl_2$ was added. The solution was washed with water, then with saturated brine and then with water again. The organic layer was dried, filtered and the solvent was evaporated. The residue was purified by column chromatography (eluent: petroleum ether/$CH_2Cl_2$ from 1/1 till 0/1). The desired fractions were collected and the solvent was evaporated. The residue was dried, yielding 10 g of intermediate (85).

b) Preparation of intermediate (86)

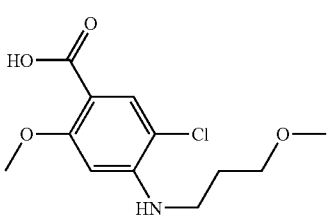

LiOH in water (1M) (80 ml) was added to a solution of intermediate (85) (0.0279 mol) in THF (120 ml) and then stirred overnight at 40° C. The solvent was evaporated. The concentrate was neutralized to pH=7. The precipitate was filtered off and dried (vacuum), yielding 4.5 g of intermediate (86).

c) Preparation of intermediate (87)

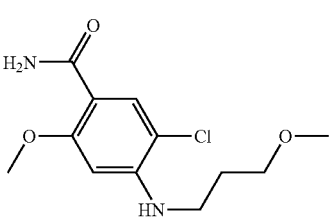

Reaction under nitrogen flow. 4-Methylmorpholine (0.0370 mol) was added to a solution of intermediate (86) (0.0340 mol) in dry $CH_2Cl_2$ (100 ml). Then 2-methyl-propyl chloroformate was added slowly to the reaction mixture and stirred at 0° C. for 30 minutes. The reaction mixture was stirred for 30 minutes at room temperature. NH$_3$ was added to the reaction mixture at 0° C. for 30 minutes. The solvent was evaporated, yielding 10 g of intermediate (87).

d) Preparation of

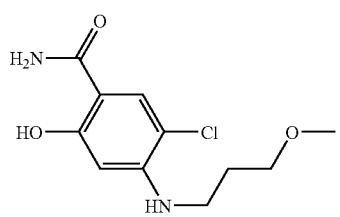

intermediate (88)

A solution of intermediate (87) (0.0370 mol) and piperazine (0.370 mol) in 1-methyl-2-pyrrolidinone (200 ml) was stirred at 140° C. for 14 hours. The solvent was evaporated. Water was added to the crude and this mixture was extracted 3 times with ethyl acetate. The separated organic layer was dried (MgSO$_4$), filtered and the solvent was evaporated. The residue was purified by column chromatography over silica (eluent: petroleum ether/CH$_2$Cl$_2$ from 50/50 to 0/100). The desired product fractions were collected and the solvent was evaporated, yielding 7 g of intermediate (88).

Example A.33 a) Preparation of

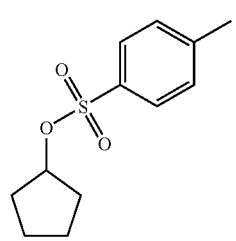

intermediate (89)

Cyclopentanol (0.2400 mol), 4-methylbenzenesulfonyl chloride (0.1400 mol) and potassium hydroxide (0.9600 mol) were dissolved in CH$_2$Cl$_2$ (200 ml) The reaction mixture was stirred at room temperature overnight. The mixture was washed with water. The organic layers were collected and the solvent was evaporated, yielding 21.5 g of intermediate (89).

b) Preparation of

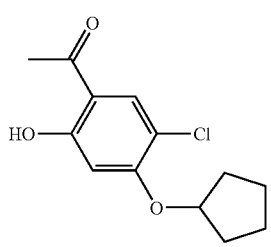

intermediate (90)

1-(5-Chloro-2,4-dihydroxy-phenyl)-ethanone (0.0550 mol) was dissolved in DMSO (150 ml), intermediate (89) (0.0660 mol) and NaHCO$_3$ (11 g) were added. The reaction mixture was stirred at 100° C. for 3 hours. Water was added. The precipitate was filtered and washed with water, yielding intermediate (90).

Example A.34

Preparation of

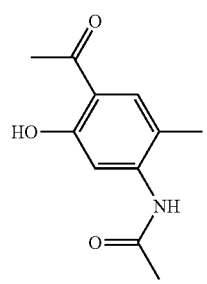

intermediate (91)

A mixture of N-[5-(acetyloxy)-2-methylphenyl]-acetamide (0.087 mol), aluminium-trichloride (0.27 mol) and sodium chloride (4 g) was stirred at 160° C. for 2 hours. The reaction mixture was cooled. Ice was added. The reaction mixture was extracted with dichloromethane. the organic layer was separated, dried, filtered and the filtrate's solvent was removed by evaporation. the residue was dried under vacuum, yielding 9 g of intermediate (91).

Example A.35 a) Preparation of

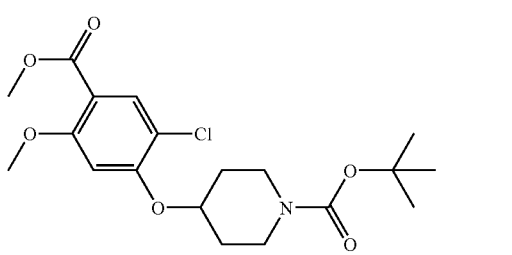

intermediate (92)

A mixture of 5-chloro-4-hydroxy-2-methoxybenzoic acid (0.0420 mol), intermediate (23) (0.0730 mol) and K$_2$CO$_3$ (10.1 g) in DMSO (200 ml) was stirred at 125° C. The solvent was evaporated. The residue was washed with water and CH$_2$Cl$_2$. The separated organic layer's solvent was evaporated, yielding 15 g of intermediate (92).

b) Preparation of

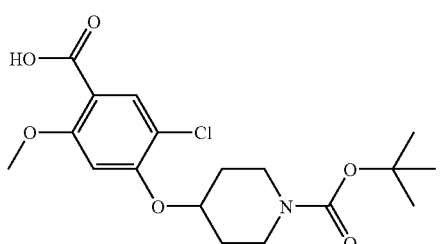

intermediate (93)

A mixture of intermediate (92) (0.0375 mol) in 2N LiOH (500 ml) and THF (150 ml) was stirred for 12 hours at room temperature. HCl was added tot the reaction mixture until the pH between 6 to 7. The reaction mixture was extracted with ether. The separated organic layer's solvent was evaporated, yielding 10 g of intermediate (93).

c) Preparation of

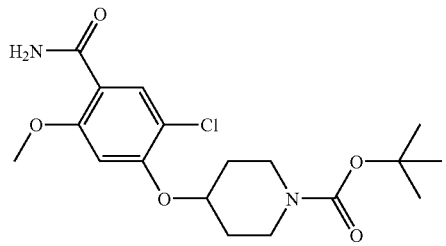

intermediate (94)

Di-1H-imidazol-1-yl-methanone (0.0143 mol) was added portion wise to a stirring solution of intermediate (93) (0.0119 mol) in dry $CH_2Cl_2$ (150 ml) and then stirred for 1 hour at room temperature. This reaction mixture was added drop wise to $NH_3$ in methanol (7N) (200 ml) within 30 minutes. The reaction mixture was stirred for 1 hour at 0° C. and then 2 hours at room temperature. The solvent was evaporated, yielding intermediate (94).

d) Preparation of

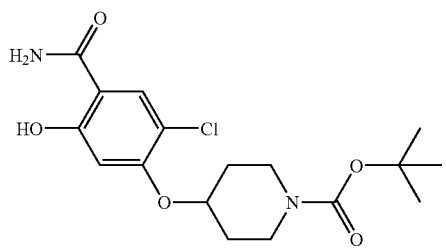

intermediate (95)

A mixture of intermediate (94) (0.0130 mol) and piperazine (0.1169 mol) in 1-methyl-2-pyrrolidinone (50 ml) was stirred for 16 hours at 140° C. Piperazine and 1-methyl-2-pyrrolidinone were evaporated (vacuum). The residue was purified by column chromatography (eluent: from petroleum ether/$CH_2Cl_2$ 50/50 to $CH_2Cl_2$ and then $CH_2Cl_2$/ethyl acetate 4/1). The desired product fractions were collected and the solvent was evaporated, yielding 4.1 g of intermediate (95).

Example A.36

Preparation of

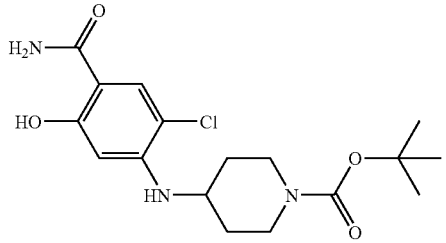

intermediate (96)

A mixture of 4-[[4-(aminocarbonyl)-2-chloro-5-methoxyphenyl]amino]-1-piperidinecarboxylic acid 1,1-dimethylethyl ester (0.021 mol) and piperazine (0.063 mol) in 1-methyl-2-pyrrolidinone (21 ml) was stirred for 16 hours at 140° C. The reaction mixture was cooled to room temperature, then poured out into ice-water (300 ml). The mixture was acidified to pH=±4 with acetic acid. The resulting precipitate was filtered off, washed with water, then taken up into $CH_2Cl_2$. The separated organic layer was dried ($MgSO_4$), filtered and the solvent evaporated. The residue was stirred in DIPE, filtered off and dried in vacuum, yielding 7.3 g of intermediate (48).

Example A.37 a) Preparation of

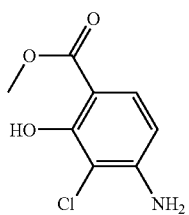

intermediate (97)

A solution of 1-chloro-2,5-pyrrolidinedione (0.2270 mol) in DMF was added drop wise to a solution of 4-amino-2-hydroxybenzoic acid methyl ester (0.2510 mol) in DMF and stirred overnight at 40° C. The solvent was evaporated. The residue was purified by high performance liquid chromatography. The desired product fractions were collected and washed with $Na_2CO_3$ aqueous solution until the pH reached 8-9. $CH_2Cl_2$ (1000 ml) was added. The separated organic layer was washed twice with water, dried ($MgSO_4$), filtered and the solvent was evaporated, yielding 14 g of intermediate (97).

b) Preparation of

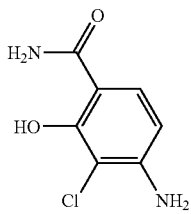
intermediate (98)

A solution of intermediate (97) (0.0496 mol) in CH₃OH (600 ml) saturated with NH₃ was stirred in an autoclave at 125° C. for 14 hours. The reaction mixture was cooled to room temperature and the solvent was evaporated. The residue was washed with DIPE, yielding 8.5 g of intermediate (98).

Example A.38

Preparation of intermediate (99)

1-(2,4-Dihydroxy-5-methylphenyl)ethanone (0.0120 mol) and 2-bromopropane (0.0120 mol) were dissolved in 2-butanone (8 ml). K₂CO₃ (0.0210 mol), potassium iodide (catalytic quantity) and DMSO (1.5 ml) were added. The reaction mixture was stirred and refluxed for 5 hours. The mixture was cooled to 40° C. and diluted with water (22 ml). The product was extracted with toluene (2 times 30 ml). The toluene solution was washed with 0.5N NaOH (2 times 20 ml), 1 time with 1N HCl (20 ml) and 2 times with water (20 ml). The organic layer was dried, filtered and the solvent was evaporated, yielding 1.3 g of intermediate (99).

Example A.39

Preparation of intermediate (100)

To a well stirred mixture of 20% NaOH (aqueous solution) (500 ml) and benzene (200 ml) at +5° C. was added 2-bromoethanamine hydrobromide (0.3300 mol). The mixture was stirred for 10 minutes at +3° C. (ice-salt bath); then a solution of 2,6-dichlorobenzoyl chloride (0.3320 mol) in benzene (50 ml) was added in course of 20 minutes maintaining the temperature below +7° C. The resulting mixture was stirred for 15 minutes at 20° C. The product precipitated was filtered off, washed with water (5×200 ml) until pH of about 7, dried and then dissolved in CH₃CN (200 ml); the solution was treated with active charcoal, concentrated to 135 g and allowed to crystallize for 15 hours at +25° C. and then for 2 hours at −10° C. The crystals were decanted, dried in vacuum, then triturated to the degree of fine powder and dried at 100° C. and 0.05 mm Hg for 1 hour, yielding 82 g of intermediate (100) (mp.: 110-111° C.).

Example A.40 a) Preparation of

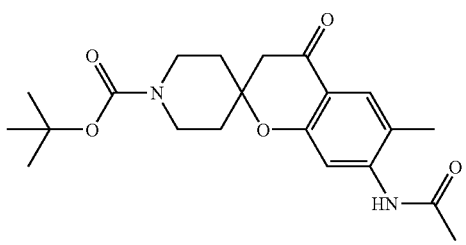
intermediate (101)

A mixture of intermediate (91) (0.0220 mol), 1,1-dimethylethyl ester 4-oxo-1-piperidinecarboxylic acid (0.0250 mol) and pyrrolidine (0.0480 mol) in methanol (150 ml) was stirred at 80° C. for 20 hours. The reaction mixture was cooled, filtered, and the solvent was evaporated. The residue was partitioned between CH₂Cl₂ and 1N NaOH. The organic layer was separated, dried (MgSO₄), filtered and the solvent was evaporated. The residue was suspended in DIPE and CH₃CN, filtered off, then dried under vacuum at 50° C., yielding 3.5 g of intermediate (101).

b) Preparation of intermediate (102)

Intermediate (101) (0.0130 mol) in THF (100 ml) was stirred under nitrogen atmosphere. Sodium hydride (0.0170 mol) was added. The reaction mixture was stirred at 50° C. for 15 minutes. 1-Bromo-3-methoxypropane (0.0250 mol) was added. The reaction mixture was stirred and refluxed for 20 hours. Extra 1-bromo-3-methoxy-propane was added. The solvent was evaporated. The residue was partitioned between CH₂Cl₂ and water. The organic layer was separated, dried (MgSO₄), and the solvent was evaporated. The residue was purified by column chromatography over silica gel (eluent: CH$_2$Cl$_2$/CH$_3$OH 98/2). The product fractions were collected and the solvent was evaporated, yielding 4.5 g of intermediate (102).

c) Preparation of

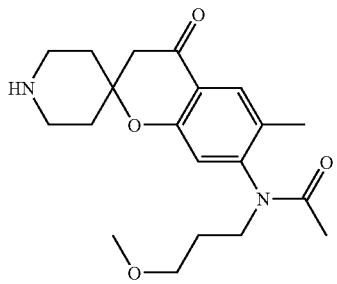

intermediate (103)

A mixture of intermediate (102) (0.0100 mol) in 6N HCl (17 ml) and EtOH (50 ml) was stirred and refluxed for 3 hours, then cooled, and the EtOH was evaporated off. The aqueous layer was alkalized with NaOH 50% (while cooling!). The mixture was extracted with CH$_2$Cl$_2$. The separated organic layer was dried (MgSO$_4$), filtered and the solvent evaporated, yielding 1.8 g of intermediate (103).

Example A.41 a) Preparation of

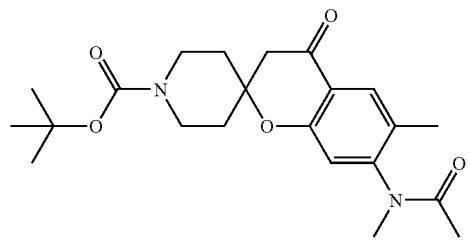

intermediate (104)

Intermediate (101) (0.0103 mol) in THF under nitrogen atmosphere. Sodium hydride (0.0120 mol) was added and then stirred at 40° C. for 15 minutes. Then iodomethane (0.0200 mol) was added and stirred at reflux for 20 hours. The reaction mixture was cooled and the solvent was evaporated. The residue was taken up in CH$_2$Cl$_2$/water. The organic layer was separated, dried (MgSO$_4$), filtered and the solvent was evaporated. The residue was purified by column chromatograhpy (silica, eluent: CH$_2$Cl$_2$/CH$_3$OH 98/2). The product fractions were collected and the solvent was evaporated, yielding 3 g of intermediate (104).

Preparation of

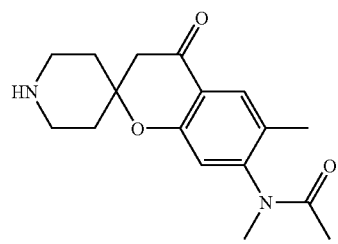

intermediate (105)

A mixture of intermediate (104) (0.0075 mol) in 6N HCl (15 ml) and EtOH (50 ml) was refluxed for 20 hours. The reaction mixture was cooled, EtOH was evaporated, residue was alkalized with NaOH 50% under cooling. This mixture was extracted with CH$_2$Cl$_2$, the organic layer was separated, dried (MgSO$_4$), filtered, and the solvent was evaporated. The residue was suspended in DIPE, filtered off and dried under vacuum, yielding 1.9 g of intermediate (105).

Example A.42 a) Preparation of

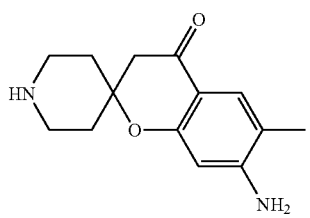

intermediate (106)

A mixture of intermediate (101) (0.0050 mol) in EtOH (25 ml). 6N HCl (7 ml) was added and the resultant reaction mixture was stirred and refluxed for 1 hour. The reaction mixture was cooled and the EtOH solvent was evaporated. The aqueous acidic concentrate was alkalized with NaOH 50%, while cooling on an ice-bath. The solid was filtered, washed with water and dried under vacuum at 50° C., yielding 1 g of intermediate (106).

b) Preparation of

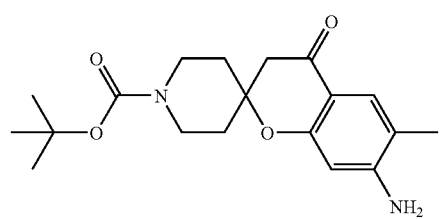

intermediate (107)

A mixture of di-tert-butyl dicarbonate in CHCl$_3$ (5 ml) was added to a mixture of intermediate (106) (0.0040 mol) in CHCl$_3$ (10 ml) at 0° C. The reaction mixture was stirred for 5 minutes and washed with water. The organic layer was separated, dried (MgSO$_4$), filtered and the solvent was evaporated. The residue was suspended in DIPE and dried under vacuum at 50° C., yielding 1 g of intermediate (107).

c) Preparation of intermediate (108)

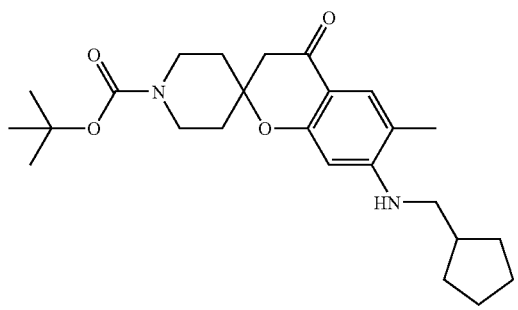

Cyclopentanecarboxaldehyde (0.0080 mol) was added to a mixture of intermediate (107) (0.0060 mol) in CH$_2$Cl$_2$ (120 ml) and acetic acid (1.2 ml), then titanium isopropoxide (excess) was added and the reaction mixture was stirred for 30 minutes at room temperature. NaBH$_3$CN (0.5 g) was added and the reaction mixture was stirred for 2 hours at room temperature. The mixture was washed with a 1N NaOH solution. The organic layer was separated, dried (MgSO$_4$), filtered and the solvent was evaporated. The residue was suspended in DIPE, yielding 2.5 g of intermediate (108).

d) Preparation of intermediate (109)

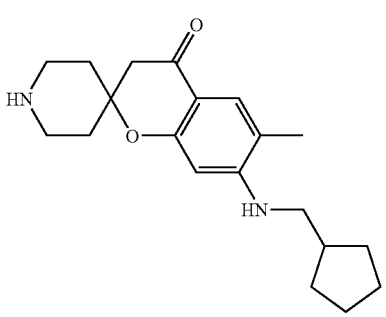

Trifluoroacetic acid (20 ml) was added on ice bath to a mixture of intermediate (108) (0.0060 mol) in CHCl$_3$ (25 ml). The reaction mixture was stirred at room temperature for 1 hour and the solvent was evaporated. The residue was washed with CH$_2$Cl$_2$/1N NaOH, then the organic layer was separated, dried (MgSO$_4$), filtered and the solvent was evaporated, yielding 1.8 g of intermediate (109).

Example A.43

Preparation of intermediate (110)

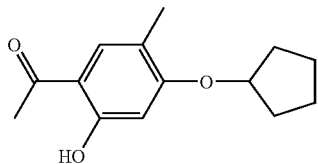

1-(2,4-Dihydroxy-5-methylphenyl)ethanone (0.024 mol) and bromocyclopentane (2.7 ml) were dissolved in 2-butanone (16 ml). K$_2$CO$_3$ (5.8 g), potassium iodide (catalytic quantity) and DMSO (3 ml) were added. The reaction mixture was stirred and refluxed for 5 hours. The mixture was cooled to 40° C. and diluted with water (50 ml). The product was extracted with toluene (twice 30 ml). The toluene solution was washed with 0.5N NaOH (twice 20 ml), with 1N HCl (once 20 ml) and with water (twice 20 ml). The organic layer was separated, dried, filtered and the solvent was evaporated, yielding 3.5 g of intermediate (110).

Example A.44

Preparation of intermediate (111)

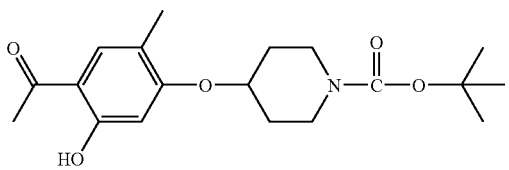

1-(2,4-Dihydroxy-5-methylphenyl)ethanone (0.018 mol) and intermediate (23) (0.019 mol) were dissolved in 2-butanone (12 ml). K$_2$CO$_3$ (4.4 g), potassium iodide (catalytic quantity) and DMSO (2.2 ml) were added. The reaction mixture was stirred and refluxed overnight. The mixture was cooled to 40° C. and diluted with water (50 ml). The product was extracted with toluene (2 times 30 ml). The toluene solution was washed with 0.5N NaOH (twice 20 ml), with 1N HCl (once 20 ml) and water (twice 20 ml). The organic layer was dried, filtered and the solvent was evaporated, yielding 4.9 g of intermediate (111).

Example A.45 a) Preparation of intermediate (112)

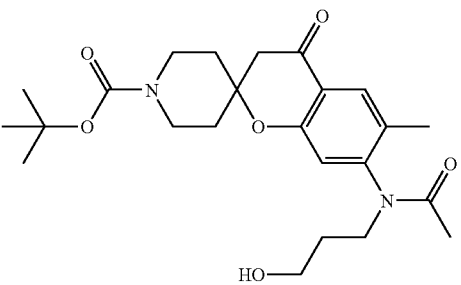

Intermediate (101) (0.013 mol) in THF (150 ml) was stirred under nitrogen flow. Sodium hydride (0.017 mol) was added. The reaction mixture was stirred at 50° C. for 15 minutes. 3-Bromo-1-propanol (0.025 mol) was added. The reaction mixture was stirred and refluxed for 20 hours, then cooled and the solvent was evaporated. The residue was partitioned between $CH_2Cl_2$ and water. The organic layer was separated, dried ($MgSO_4$), filtered and the filtrate's solvent was evaporated. The residue was purified by column chromatography over silica gel (eluent: $CH_2Cl_2/CH_3OH$ 98/2). The product fractions were collected and the solvent was evaporated, yielding 1.8 g of intermediate (112).

b) Preparation of

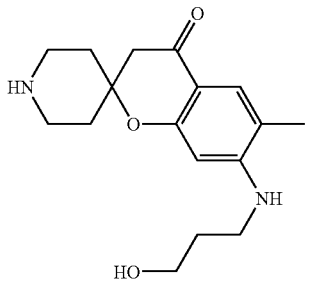

intermediate (113)

A mixture of intermediate (112) (0.004 mol) and 6N HCl (5.4 ml) in EtOH (20 ml) was stirred and refluxed for 2 hours. The reaction mixture was cooled and the ethanol solvent was evaporated. The aqueous concentrate was alkalized with 50% NaOH. The solvent was evaporated. The residue was stirred in $CH_2Cl_2$ (+$CH_3OH$)/a little water+sodium chloride. The mixture was stirred and filtered. The separated organic layer was dried ($MgSO_4$), filtered and the solvent evaporated, yielding 0.7 g of intermediate (113).

Example A.46 a) Preparation of intermediate (114)

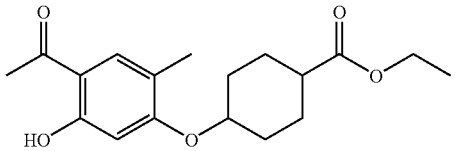

To a mixture of 1-(2,4-dihydroxy-5-methylphenyl)-ethenone (12.035 mmol) and 4-[[(4-methylphenyl)sulfonyl]oxy]-cyclohexanecarboxylic acid, ethyl ester (12.035 mmol) in 2-butanone (8 ml), potassium iodide (catalytic quantity), potassium carbonate (3 g) and DMSO (2 ml) were added. The reaction mixture was refluxed for 20 hours and cooled. Water was added, the reaction mixture was extracted with toluene. The organic layer was washed with 1 N sodium hydroxide, dried (MgSO4), filtered and the solvent was evaporated, yielding 1.7 g of intermediate (114).

Example A.47 a) Preparation of

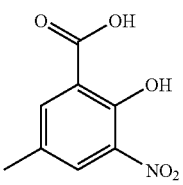

intermediate (115)

2-Hydroxy-5-methyl-benzoic acid (328.6 mmol) was dissolved in sulfuric acid (concentrated 175 ml). The mixture was cooled to 0° C. A mixture of nitric acid (concentrated 15.2 ml) and sulfuric acid (concentrated, 15.2 ml) was added dropwise. The mixture was stirred at 20° C. for another 7 hours. The mixture was filtered off and the residue was extracted with ethyl acetate. The organic layer was washed with water (100 ml*3), dried ($Na_2SO_4$), filtered, evaporated. The product was dried in the vacuum at 60° C. for 8 hours, yielding 30 g of intermediate (115).

b) Preparation of

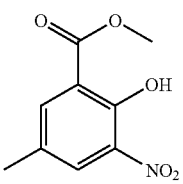

intermediate (116)

Intermediate (115) (152.17 mmol) was dissolved in $CH_3OH$ (150 ml). Sulfuric acid (concentrated, 30 ml) was added at 0° C. The mixture was stirred at 85° C. for 16 hour. The precipitate was filtered off and dried in the vacuum at 60° C. for 12 hours, yielding 13 g of intermediate (116).

c) Preparation of

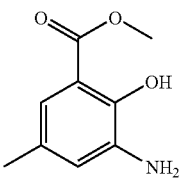

intermediate (117)

Intermediate (116) was dissolved in THF (165 ml). $NaHCO_3$ (260.5 mmol) was added, followed by water (165 ml). $Na_2S_2O_4$ (156.3 mmol) was added in portions, followed by $CH_3OH$ (165 ml). The reaction mixture was stirred for 30 minutes. The solvent was evaporated under vacuum. The residue was dissolved in HCl (2 N) solution. The residue was extracted with $CH_2Cl_2$ (2*50 ml). The water layer was basified with solid NaHCO₃ until pH to 8, and extracted with ethyl acetate. The organic layer was washed with water (50 ml*3) and dried (Na₂SO₄), filtered off, evaporated, yielding 6.6 g of intermediate (117).

d) Preparation of

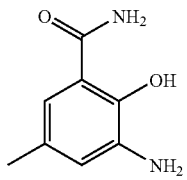

intermediate (118)

Ammonia gas was introduced to CH₃OH at −78° C. for 1.5 hours to give NH₃/CH₃OH and was used immediately in this reaction. Intermediate (117) was dissolved in NH₃/CH₃OH. The mixture was stirred at 125° C. in an autoclave for 24 hours. The solvent was evaporated at reduced pressure at 50° C. The crude was purified by column (gradient elution: petroleum ether/ethyl acetate from 15/0 to 4/1). The desired fractions were collected and the solvent was evaporated. The product was dried in vacuum at 60° C. for 12 hours, yielding 4 g of intermediate (118).

Example A.48 a) Preparation of

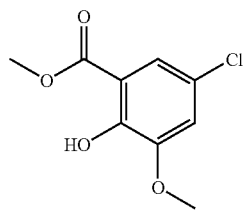

intermediate (119)

2-Hydroxy-3-methoxy-benzoic acid, methyl ester (137.2 mmol) was dissolved in toluene (600 ml). Sulfuryl chloride (22.2 ml) was added dropwise. The mixture was stirred at 25° C. for 12 hours and then heated to 60° C. for 6 hours. Water (100 ml) was added and the mixture was adjusted to pH=7 with Na₂CO₃. The organic layer was separated out and water phase was extracted by ethyl acetate (100 ml). The organic layers were combined and washed with brine and water, dried over Na₂SO₄, filtered and evaporated. The residue was recrystallized from dioxane to afford 7.6 g of pure product. Then the mother liquid was evaporated to dryness and purified by preparative high performance liquid chromatography over RP-18 (eluent: CH₃CN/water from 45/55 to 85/15 v/v with 0.1% CF₃COOH). The desired fractions were collected and the solvent was evaporated to give 9.6 g of pure product. Two batches of pure product were combined and used in the next step, yielding 17.2 g of intermediate (119).

b) Preparation of

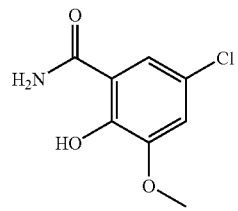

intermediate (120)

Intermediate (119) (35.09 mmol) was dissolved in saturated ammonia in CH₃OH (400 ml). The reaction was stirred at 125° C. in sealed-tube for 24 hours. The solvent was evaporated. The residue was washed with the mixture of petroleum ether (20 ml) and isopropyl ether (20 ml). The precipitate was filtered off and dried, yielding 6.2 g of intermediate (120).

Example A.49 a) Preparation of

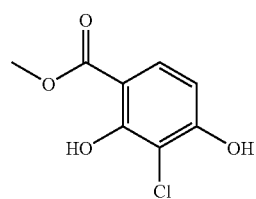

intermediate (121)

2,4-Dihydroxy-benzoic acid, methyl ester (892.9 mmol) was dissolved in DMF (1200 ml). 1-chloro-2,5-pyrrolidinedione (892.9 mmol) was added. The reaction mixture was stirred at 50° C. for 4 hours. The solvent was evaporated under reduced pressure. The residue was purified by High Performance Liquid Chromatography (eluent: CH₃CN/H₂O from 30/70 to 60/30 with 0.1% CF₃COOH). The product fractions were collected and the solvent was evaporated. The product was dried in vacuum at 50° C. for 12 hours, yielding 45 g of intermediate (121).

b) Preparation of

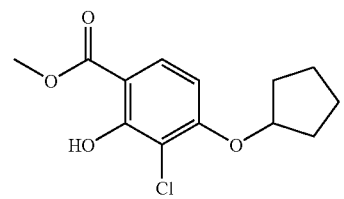

intermediate (122)

Intermediate (121) (148.08 mmol) was dissolved in DMF (350 ml). Sodium iodide (7.40 mmol) and Na₂CO₃ (296.15 mmol) were added. A solution of bromo-cyclo-pentane (296.15 mmol) in DMF (100 ml) was added at 25° C. for 30 minutes. The mixture was stirred at 60° C. for 3 hours. The mixture was cooled to 25° C., the Na₂CO₃ was filtered off.

The filtrate was washed with 2N NaOH solution (200 ml). The mixture was extracted with $CH_2Cl_2$. The organic layers were combined, washed with water, dried ($Na_2SO_4$), filtered and the solvent was evaporated. The residue was crystallized from ethyl acetate, yielding 21.5 g of intermediate (122).

c) Preparation of

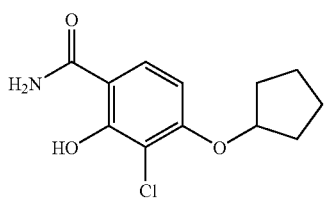

intermediate (123)

Ammonia gas was assimilated into $CH_3OH$ in the dry ice/acetone bath for 30 minutes to give $NH_3/CH_3OH$. Intermediate (122) (70.1832 mmol) was dissolved in $NH_3/CH_3OH$ (1000 ml). The mixture was stirred at 125° C. and 3 MPa in the autoclave for 24 hours. The reaction was followed by Thin Layer Chromatograph (petroleum ether/ethyl acetate 1:1, v/v). The solvent was evaporated under reduced pressure. The residue was washed with di-isopropyl ether. The precipitate was filtered off and dried in vacuum at 50° C. for 24 hours, yielding 16.4 g of intermediate (123).

Example A.50 a) Preparation of

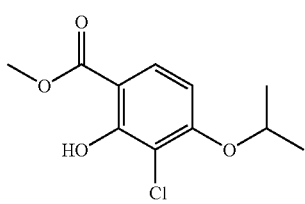

intermediate (124)

Intermediate (121) (98.7 mmol) was dissolved in DMF (200 ml). 2-Bromo-propane (197 mmol), sodium iodide (4.9 mmol) and $K_2CO_3$ (197 mmol) were added. The reaction mixture was stirred at 80° C. for 15 hours. $K_2CO_3$ was filtered off. The solvent was evaporated. The residue was dissolved in $CH_2Cl_2$ (200 ml). The mixture was washed with water (30 ml). The organic were separated, dried ($Na_2SO_4$), filtered off and evaporated. The residue was purified by column over silica gel (eluent: petroleum ether/$CH_2Cl_2$ from 99/1 to 30/1). The product fractions were collected and dried, yielding 6.1 g of intermediate (124).

b) Preparation of

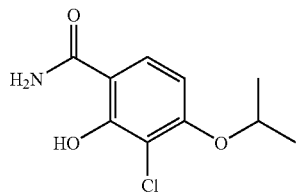

intermediate (125)

Intermediate (124) (24.9 mmol) was dissolved in saturated ammonia in $CH_3OH$ (180 ml). The reaction was stirred at 125° C. in sealed-tube for 24 hours. The solvent was evaporated. The residue was washed with a mixture of petroleum ether (20 ml) and isopropyl ether (20 ml). The precipitate was filtered off and dried, yielding 5.4 g of intermediate (125).

Example A.51 a) Preparation of

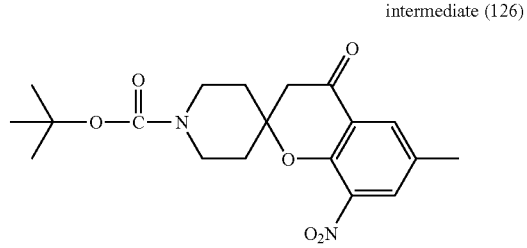

intermediate (126)

A mixture of 1-(2-hydroxy-5-methyl-3-nitrophenyl)-ethenone (92 mmol), 4-oxo-1-piperidinecarboxylic acid, 1,1-dimethylethyl ester (110 mmol) and pyrrolidine (220 mmol) in $CH_3OH$ (600 ml) was stirred for 3 hours at 80° C. The reaction mixture was cooled. The solvent was evaporated. The residue was suspended in DIPE, filtered off and dried under vacuum at 50° C., yielding 17 g of intermediate (126).

b) Preparation of

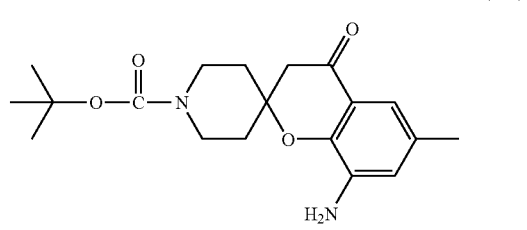

intermediate (127)

Intermediate (126) (44 mmol) was dissolved in methanol (300 ml) and the mixture was hydrogenated at 25° C. with Pd/C (10%) (3 g) as a catalyst and in the presence of a thiophene solution (1 ml). After uptake of hydrogen (3 equivalents), the reaction mixture was filtered to remove the catalyst. The filtrate was concentrated to dryness, suspended in DIPE, filtered and dried under vacuum at 50° C., yielding 14 g of intermediate (127).

c) Preparation of

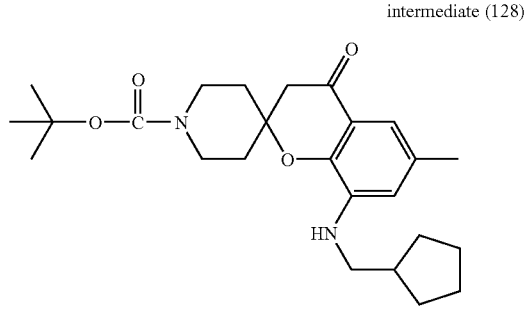

intermediate (128)

Titaniumisopropoxide (10 ml) was added to a mixture of intermediate (127) (5.7 mmol) in $CH_2Cl_2$ (120 ml) and $CH_3COOH$ (1.2 ml). Cyclopentanecarboxaldehyde (7 mmol) was added. The reaction mixture was stirred at room temperature for 30 minutes. $NaBH_3CN$ (0.5 g) was added. The mixture was stirred at room temperature for 20 hours, washed with water, dried with $MgSO_4$, filtered and the solvent was evaporated. The residue was purified by column chromatography over silica gel ($CH_2Cl_2/CH_3OH$ 98/2). The pure fractions were collected and the solvent was evaporated, yielding 1.7 g of intermediate (128).

d) Preparation of

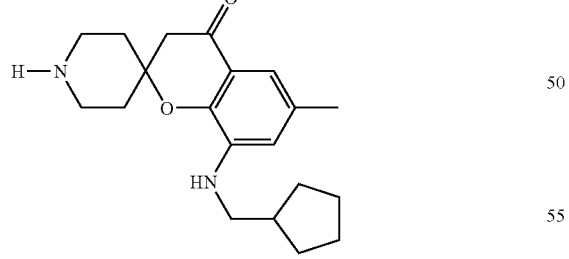

intermediate (129)

$CF_3COOH$ (13 ml) was added on an ice bath to a mixture of intermediate (128) (4 mmol) in $CHCl_3$ (20 ml). The reaction mixture was stirred at room temperature for 1 hour. The solvent was evaporated. The residue was extracted in $CH_2Cl_2$/NaOH 1N. The organic layer was separated, dried ($MgSO_4$), filtered and the solvent was evaporated. The residue was suspended in DIPE, filtered and dried under vacuum, yielding 0.66 g of intermediate (129).

Example A.52 a) Preparation of

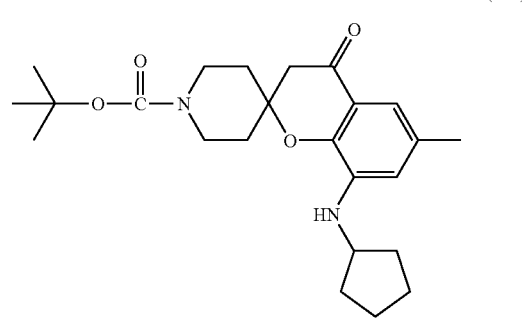

intermediate (130)

Titaniumisopropoxide (10 ml) was added to a mixture of intermediate (127) (7.2 mmol) in $CH_2Cl_2$ (120 ml) and $CH_3COOH$ (1.2 ml). Cyclopentanone (7 mmol) was added. The reaction mixture was stirred at room temperature for 30 minutes. $NaBH_3CN$ (0.6 g) was added. The mixture was stirred at room temperature for 20 hours, washed with water, dried with $MgSO_4$, filtered and the solvent was evaporated. The residue was purified by column chromatography over silica gel ($CH_2Cl_2/CH_3OH$ 98/2). The pure fractions were collected and the solvent was evaporated, yielding 2.8 g of intermediate (130).

b) Preparation of

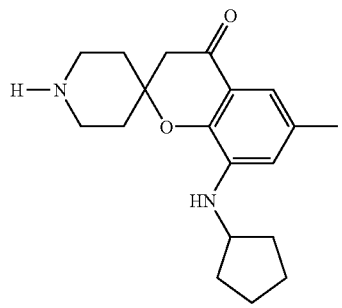

intermediate (131)

$CF_3COOH$ (20 ml) was added on an ice bath to a mixture of intermediate (130) (6.7 mmol) in $CHCl_3$ (40 ml). The reaction mixture was stirred at room temperature for 1 hour and then neutralized with a saturated solution of $NaHCO_3$. The organic layer was separated, dried with $MgSO_4$, filtered and the solvent was evaporated. The residue was suspended in DIPE, yielding 1.5 g of intermediate (131).

Example A.53 a) Preparation of intermediate (132)

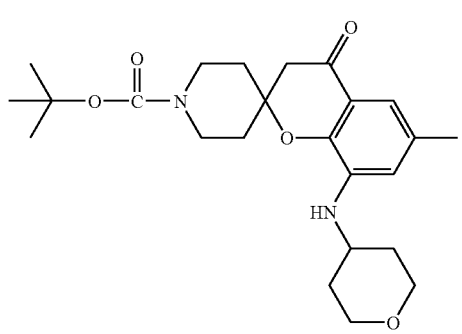

Tetrahydro-4H-pyran-4-one (10 mmol) was added to a mixture of intermediate (127) (5.7 mmol) in $CH_2Cl_2$ (120 ml) and acetic acid (1.2 ml). Titaniumisopropoxide (12 mmol) was added. The reaction mixture was stirred at room temperature for 30 minutes. $NaBH_3CN$ (0.7 g) was added. The reaction mixture was stirred at room temperature for 20 hours, washed with water, dried ($MgSO_4$), filtered and the solvent was evaporated. The residue was purified by column chromatography ($CH_2Cl_2/CH_3OH$ 99/1). The pure fractions were collected and the solvent was evaporated, yielding 2.2 g of intermediate (132).

b) Preparation of intermediate (133)

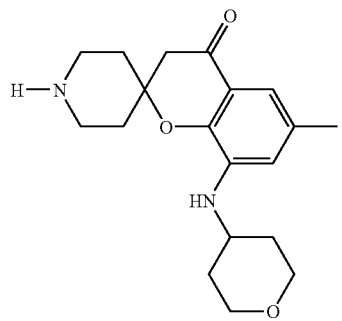

$CF_3COOH$ (17 ml) was added on an ice bath to a mixture of intermediate (132) (5.3 mmol) in $CHCl_3$ (30 ml). The reaction mixture was stirred at room temperature for 1 hour. The reaction mixture was neutralized with a saturated solution of $NaHCO_3$. The organic layer was separated, dried with $MgSO_4$, filtered and the solvent was evaporated. The residue was suspended in DIPE, yielding 1 g of intermediate (133).

Example A.54 a) Preparation of intermediate (134)

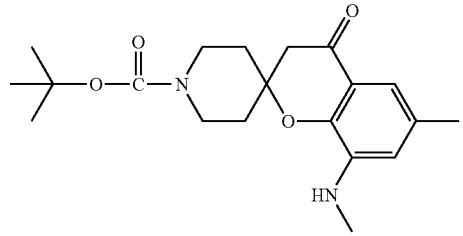

A mixture of intermediate (127) (8.7 mmol) and paraform (0.26 g) in $CH_3OH$ was hydrogenated with Pd/C 10% (0.5 g) as a catalyst in the presence of thiophene solution (0.5 ml). After uptake of hydrogen (1 equivalent), the catalyst was filtered off and the filtrate was evaporated. The residue was suspended in DIPE, filtered off and dried under vacuum, yielding 2 g of intermediate (134).

b) Preparation of intermediate (135)

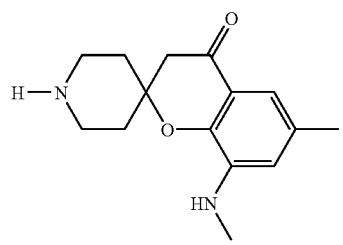

Intermediate (134) (5.5 mmol) was stirred in $CHCl_3$ (30 ml). $CF_3COOH$ (18 ml) was added on an ice bath. The reaction mixture was stirred on an ice bath for one hour. The mixture was neutralized with a saturated aqueous $NaHCO_3$ solution. The organic layer was separated, dried ($MgSO_4$), filtered and the solvent was evaporated, yielding 1.55 g of intermediate (135). This product was used without further purification.

Example A.55 a) Preparation of intermediate (136)

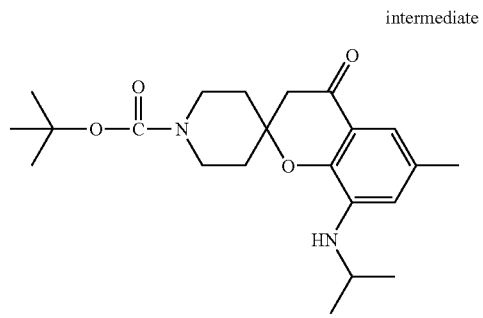

To a stirred solution of intermediate (127) (8.7 mmol) in 1,2-dichloro-ethane (26 ml) under N₂ was added 2-methoxy-1-propene (13 mmol), acetic acid (0.5 ml) and NaBH(OAc)₃ (2.8 g). The reaction mixture was stirred at room temperature for 24 hours. The mixture was washed with 1 N NaOH. The organic layer was separated, dried (MgSO₄), filtered and the solvent was evaporated. The residue was purified by column chromatography over silica gel (eluent: CH₂Cl₂/CH₃OH 99/1). The product fractions were collected and the solvent was evaporated, yielding 1.8 g of intermediate (136).

b) Preparation of

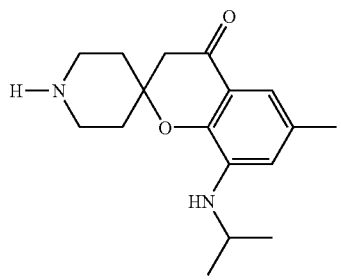

intermediate (135)

Intermediate (136) (4.7 mmol) in CHCl₃ (25 ml) was stirred. CF₃COOH (14 ml) was added on an ice bath. The reaction mixture was stirred for one hour. The mixture was neutralized with a saturated aqueous NaHCO₃ solution, under cooling. The organic layer was separated, dried (MgSO₄), filtered and the solvent was evaporated, yielding 1.3 g of intermediate (137).

Example A.56

Preparation of

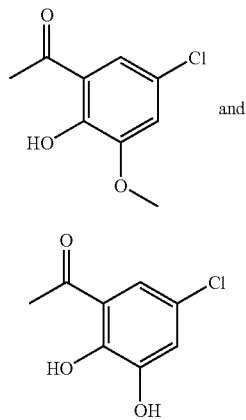

intermediate (138)

and intermediate (139)

4-Chloro-2-methoxy-phenol (63.058 mmol) was dissolved in BF₃.HOAc (72 ml). The mixture was heated to 135° C. for 24 hours. After cooling to 40° C. the mixture was poured into ice. The mixture was extracted (CH₂Cl₂). The organic layers were washed with water. The organic layer was dried, filtered and the solvent was evaporated. The residue (10 g) was purified with column chromatography (CH₂Cl₂/Heptane 70/30), yielding intermediate (138) and 4.9 g of intermediate (139).

Example A.57 a) Preparation of

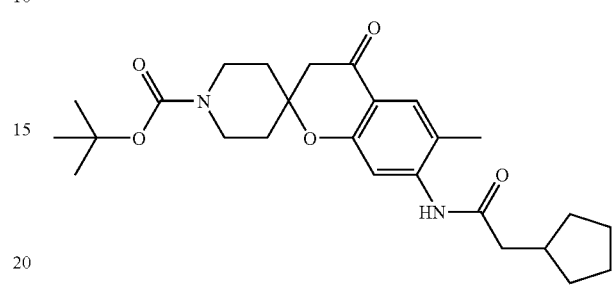

intermediate (140)

Intermediate (107) (8.66 mmol) was dissolved in CH₂Cl₂. Triethylamine (9.526 mmol) and cyclopentaneacetyl chloride (9.526 mmol) were added. After stirring at room temperature for 1 hour, water was added to the reaction mixture. The mixture was extracted (CH₂Cl₂) and the organic layer was dried, filtered and the solvent was evaporated. The residue was used as such, yielding 4.5 g of intermediate (140).

b) Preparation of

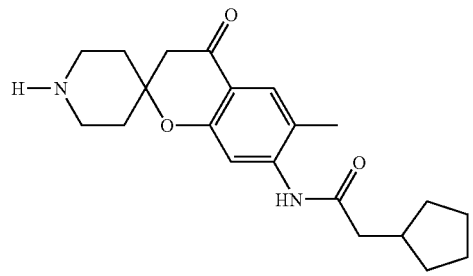

intermediate (141)

Intermediate (140) (4.38 mmol) was dissolved in EtOH (30 ml). HCl (6M, 43.804 mmol) was added. The reaction mixture was refluxed for 1 hours and cooled to room temperature. The precipitate was filtered, washed with DIPE and dried. The residue was used crude, yielding 1.66 g of intermediate (141).

Other intermediate compounds that were used in the preparation of the final compounds are art known compounds such as, 2-hydroxy-4-methoxy-benzamide, 2-acetyl-4-chloro-5-methylphenyl, 2-hydroxy-4-acetamido-5-chlorobenzamide, 5-chloro-2,4-dihydroxy-benzamide, 2-acetyl-5-aminophenol, 2-acetylphenol, 2-acetyl-4,5-dimethylphenol, 2-acetyl-4-methylphenol, 2-acetylbenzene-1,3-diol, 2-acetyl-5-ethoxyphenol, 2-acetyl-4-methoxyphenol, 1-(2-ethyl-6-methoxy-phenyl)-ethanone, 1-(2-hydroxy-3,4-dimethoxyphenyl)-ethanone, 1-(2-hydroxy-4,5-dimethoxyphenyl)-ethanone, 1-(4-ethoxy-2-hydroxy-3-methylphenyl)-ethanone, 1-(2-hydroxy-4,6-dimethoxyphenyl)-ethanone, 1-(2-hydroxy-4-methoxyphenyl)-ethanone, 1-(4-fluoro-2-hydroxyphenyl)-ethanone, 4-amino-1-methylpiperidine, 1-(3,5-dichloro-2-hydroxy-phenyl)-ethanone, 1-(5-fluoro-2-hydroxyphenyl)-ethanone, 1-(5-ethoxy-2-hydroxy-phenyl)-ethanone, 1-(3-bromo-5-chloro-2-hydroxyphenyl)-ethanone, 1-(2,6-dihydroxy-4-methoxyphenyl)-ethanone, 1-(5-chloro-2-hydroxyphenyl)-ethanone, 1-[2-hydroxy-6-(2-propenyloxy)-phenyl]-ethanone, 1-(2-hydroxy-4-methylphenyl)-ethanone, 1-(4-fluoro-2-hydroxy-phenyl)-ethanone, 1-(3,5-dibromo-2-hydroxyphenyl)-ethanone, 1-(3-amino-2-hydroxy-5-methylphenyl)-ethanone, 1-[2-hydroxy-3-methyl-4-(phenyl-methoxy)phenyl]-ethanone, 1-(3,5-difluoro-2-hydroxyphenyl)-ethanone, 1-(5-ethyl-2-hydroxyphenyl)-ethanone, 1-[2-hydroxy-5-(trifluoromethoxy)phenyl]-ethanone, 1-(2-hydroxy-3,6-dimethoxyphenyl)-ethanone, 1-(5-bromo-2-hydroxyphenyl)-ethanone, 1-(2-hydroxy-5-nitrophenyl)-ethanone, 1-(2-fluoro-6-hydroxyphenyl)-ethanone, 1-(tert-butoxy-carbonyl)-4-aminopiperidine, 1,1-dimethylethyl ester N-(3-acetyl-2-hydroxy-5-methylphenyl)-carbamic acid, 1-(3-chloro-2-hydroxyphenyl)-ethanone, 3-methoxy-1-propanamine, N-(4-acetyl-3-hydroxyphenyl)-acetamide, tetrahydro-2H-pyran-4-amine, trifluoroacetic acid anhydride, cyclopentanemethanamine hydrochloride, 2'-hydroxy-3'-methoxy-5'-methyl-acetophenone, 2',3'-dihydroxy-5'-methyl-acetophenone, and 3-amino-5-chloro-2-hydroxy-benzamide.

B. Preparation of the Final Compounds

Example B.1

Preparation of compound (1)

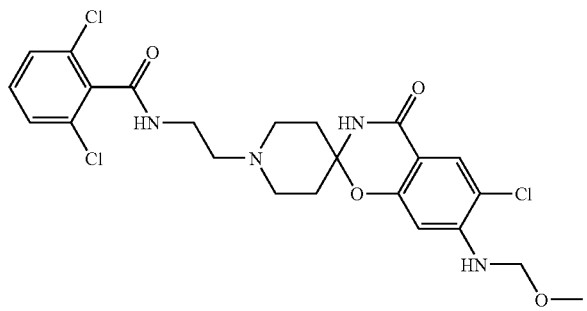

2,6-Dichlorobenzoyl chloride (0.00723 mol) was added drop by drop at room temperature in 5 minutes to a mixture of intermediate (5) (0.00482 mol) and DIPEA (0.024 mol) in $CH_2Cl_2$ (20 ml) and DMF (20 ml). The reaction mixture was stirred for 3 hours at room temperature. The solvent was evaporated. The residue was purified by column chromatography over silica gel (eluent: $CH_2Cl_2/(CH_3OH/NH_3)$ 95/5). The product fractions were collected and the solvent was evaporated. The residue was precipitated in DIPE and the precipitate was filtered off, yielding 0.710 g of compound (1).

Example B.2

Preparation of compound (2)

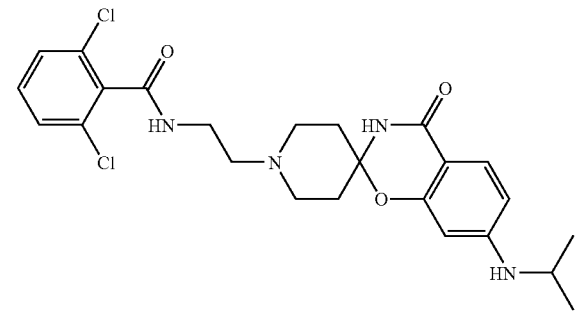

A mixture of compound (1) (0.0021 mol) and formaldehyde (0.124 g) in THF (50 ml) and methanol (100 ml) was hydrogenated with platinum-on-carbon (5%; 0.3 g) as a catalyst in the presence of a thiophene solution (0.3 ml). After uptake of hydrogen (1 equivalent), the catalyst was filtered off and the filtrate was evaporated. The residue was purified by high-performance liquid chromatography. The product fractions were collected and the solvent was evaporated. The residue was re-crystallized from $CH_3CN$ and the precipitate was filtered off, yielding 0.143 g of compound (2).

Example B.3

Preparation of compound (3)

Pyrrolidine (0.0009 mol) was added to a mixture of intermediate (8) (0.009 mol) and intermediate (9) (0.009 mol) in toluene. The reaction mixture was stirred and refluxed for 16 hours using a Dean Stark water-separator. Toluene was evaporated off under reduced pressure. The residue was dissolved in $CH_2Cl_2$. This mixture was washed with water, washed with brine and then washed again with water. The separated organic layer was dried ($MgSO_4$), filtered and the solvent was evaporated under reduced pressure. The residue was purified by high-performance liquid chromatography. The product fractions were collected and the solvents were evaporated. The residue was triturated under DIPE and the precipitate was filtered off and dried, yielding 0.151 g of compound (3).

Example B.4

Preparation of compound (17)

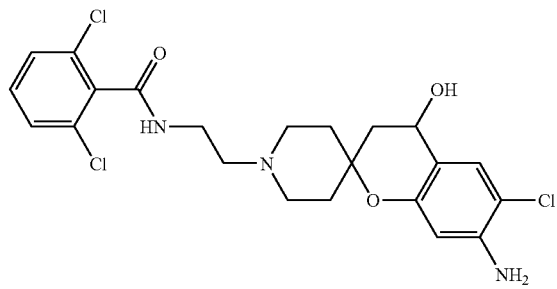

NaBH₄ (0.00055 mol) was added to a solution of compound (7) (0.00046 mol) in EtOH (5 ml) and stirred overnight at 50° C. The reaction mixture was quenched with NH₄Cl. This mixture was extracted 2 times with ethyl acetate. The separated organic layer was washed with brine, dried (MgSO₄), filtered and the solvent was evaporated, yielding 0.190 g of compound (17).

Example B.5

Preparation of compound (10)

Compound (17) (0.00039 mol) and triethylsilane (0.0039 mol) in trifluoroacetic acid (0.00235 mol) and CH₂Cl₂ (5 ml) were heated overnight at 60° C. in a sealed tube. The solvent was evaporated. The residue was dissolved in CH₂Cl₂. This mixture was washed with NH₃ aqueous solution and washed with water. The separated organic layer was dried (MgSO₄), filtered and the solvent was evaporated. The residue was purified by column chromatography over silica gel (eluent: CH₂Cl₂/CH₃OH 97/3). The product fractions were collected and the solvent was evaporated, yielding 0.089 g of compound (10).

Example B.6

Preparation of compound (22)

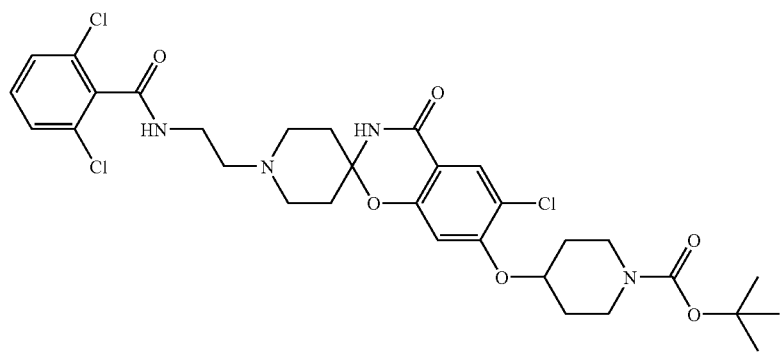

A mixture of compound (21) (0.0167 mol), 4-[[(4-methylphenyl)sulfonyl]oxy]-1-piperidinecarboxylic acid 1,1-dimethylethyl ester (0.0283 mol) and K₂CO₃ (6.9 g) in CH₃CN was stirred and refluxed for 16 hours. The solvent was evaporated under reduced pressure. Water (200 ml) was added. This mixture was extracted with CH₂Cl₂ (3×150 ml). The organic layer was separated, dried (MgSO₄), filtered and the solvent was evaporated under reduced pressure. CH₃CN (50 ml) was added. The crude oily solution was left to stand and the resulting white precipitate was filtered off, washed with DIPE and dried, yielding 6.16 g of compound (22).

Example B.7

Preparation of compound (23)

Compound (22) (0.0092 mol) was dissolved in CH$_2$Cl$_2$ (100 ml). A solution of trifluoroacetic acid in CH$_2$Cl$_2$ (50%) (40 ml) was added dropwise and the reaction mixture was stirred for one hour at room temperature. The solvent was evaporated. The residue was dissolved in CH$_2$Cl$_2$ (100 ml). The organic solution was washed with 1N NaOH, then dried (MgSO$_4$), filtered and the solvent was evaporated. The residue was precipitated in DIPE, filtered off and dried (vacuum, 50° C.), yielding 3.28 g of compound (23).

This reaction may also be performed using HCl dissolved in isopropanol or dioxane.

Compound (99) was prepared analogously starting from compound (103) using HCl dissolved in dioxane.

Example B.8

Preparation of compound (26)

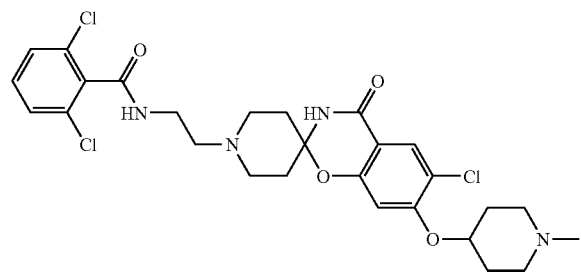

Compound (23) (0.00264 mol) was dissolved in methanol (20 ml). Formaldehyde (0.00792 mol) was added in one portion, followed by the addition of NaBH(OAc)$_3$ (95%) (0.0792 mol). The reaction mixture was stirred for 3 hours at 55° C. Extra NaBH(OAc)$_3$ (95%) (1 g) was added (gas evolution over 10 minutes). The solvent was evaporated under reduced pressure. Water (100 ml) was added and 1N NaOH (up to 50 ml) was added. This mixture was extracted with ethyl acetate (3×200 ml). The combined organic layers were dried (MgSO$_4$), filtered and the solvent was evaporated. The residue was precipitated in DIPE, then filtered off and dried (50° C., overnight, under reduced pressure), yielding 0.984 g of compound (26).

Example B.9

Preparation of compound (27)

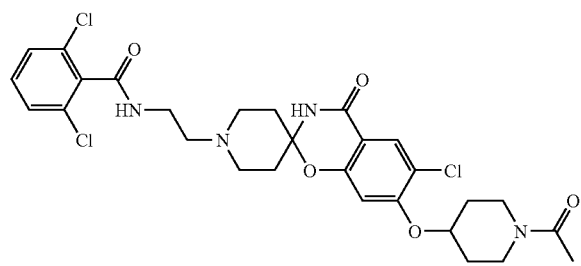

Compound (23) (0.00176 mol) and DIPEA (0.00880 mol) were dissolved in CH$_2$Cl$_2$ and cooled to 0° C. Acetyl chloride (0.00352 mol) was added dropwise. The reaction mixture was stirred for one hour at 0° C. The solvent was evaporated. The residue was dissolved in CH$_2$Cl$_2$, washed with water, dried, filtered and the solvent evaporated under reduced pressure. The residue (crude oil) was crystallized from CH$_3$CN. The product fractions were collected and the solvent was evaporated. The precipitate was filtered off and dried, yielding 0.825 g of compound (27).

Example B.10

Preparation of compound (43)

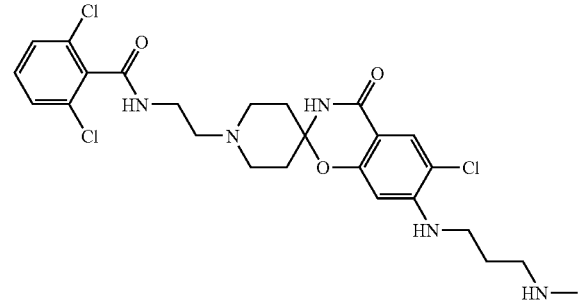

A mixture of compound (42) (0.00173 mol) in CH$_2$Cl$_2$ (11 ml) was stirred at room temperature. A mixture of trifluoroacetic acid (4 ml) and CH$_2$Cl$_2$ (p.a.) (5 ml) was added dropwise and the reaction mixture was stirred for 2 hours at room temperature. The solvent was evaporated. The residue was taken up into water/CH$_3$CN and alkalized with 1N NaOH. The resulting precipitate was filtered off and dried, yielding 0.501 g of compound (43).

Example B.11

Preparation of compound (45)

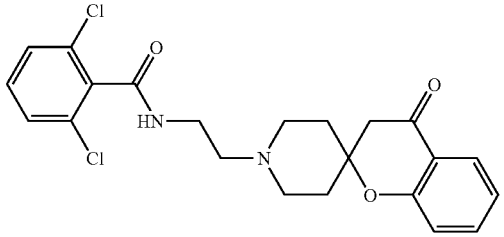

1-(2-Hydroxyphenyl)ethanone (0.021 mol) was added to a mixture of intermediate (8) (0.013 mol) and pyrrolidine (0.043 mol) in methanol (40 ml). The reaction mixture was stirred for 12 hours at 80° C., then cooled. The solvent was evaporated. The residue was dissolved in CH$_2$Cl$_2$ (200 ml). The organic solution was washed with water, then with brine, then dried (Na$_2$SO$_4$), filtered and the solvent was evaporated in vacuum. The residue was purified by column chromatography over silica gel (eluent: CH$_2$Cl$_2$/CH$_3$OH 200/1). The product fractions were collected and the solvent was evaporated. The residue was recrystallized from CH₃CN. The precipitate was filtered off and dried, yielding 2.6 g of compound (45).

Compound (103) was prepared analogously using intermediates (8) and (84).

Example B.12

Preparation of

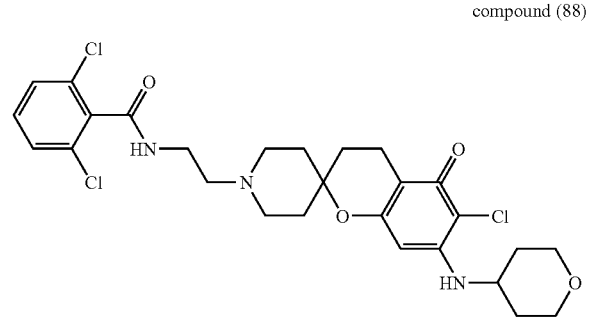

compound (88)

Reaction in microwave oven. Compound (87) (0.00549 mol), Pd(OAc)₂ (0.24 g), BINAP (0.27 g) and Cs₂CO₃ (0.01097 mol) were dissolved in 1-methyl-2-pyrrolidinone (60 ml). Then, tetrahydro-2H-pyran-4-amine (0.01097 mol) was added. The reaction mixture was stirred for 50 minutes at 110° C. The solvent was evaporated. The residue was diluted with CH₂Cl₂, then washed with water (2×), dried (MgSO₄), filtered and the solvent was evaporated. The residue was purified by preparative high-performance liquid chromatography. The product fractions were collected and the solvent was evaporated. The residue was acidified with HCl/1,4-dioxane. The salt was filtered off and dried, yielding 0.48 g of compound (88).

Example B.13

Preparation of

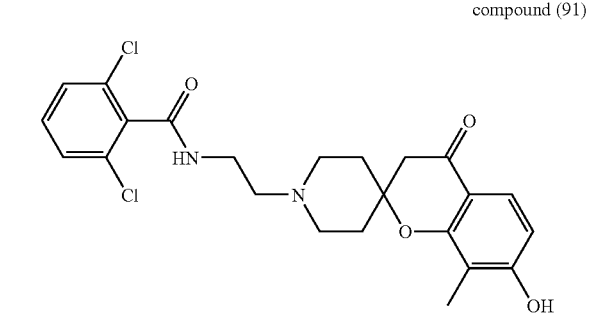

compound (91)

Compound (74) (0.0107 mol) was dissolved in methanol (150 ml). Raney Nickel (catalytic quantity) was added. The mixture was hydrogenated for 12 hours. After uptake of hydrogen (1 equivalent), the catalyst was filtered off and the filtrate was evaporated. The residue was purified by column chromatography over silica gel (eluent: ethyl acetate). The product fractions were collected and the solvent was evaporated. The residue was dissolved in 1,4-dioxane and converted into the hydrochloric acid salt (1:1) with HCl/2-propanol. The precipitate was filtered off and dried (vacuum), yielding 0.75 g of compound (91).

Example B.14

Preparation of

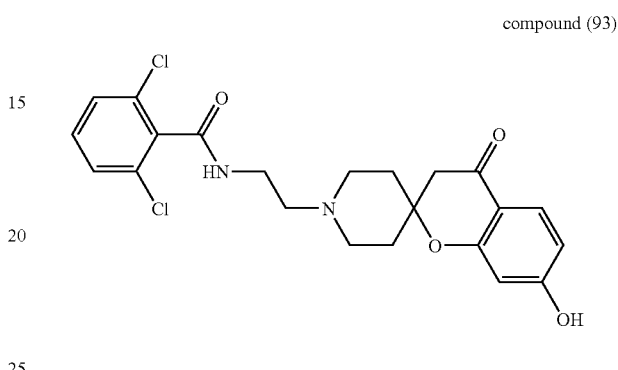

compound (93)

Reaction under nitrogen atmosphere. Compound (58) (0.0065 mol) was dissolved in CH₂Cl₂ and cooled to −20° C. BBr₃ (30 ml) was added at −20° C. The reaction mixture was stirred for 12 hours at room temperature. Water was added (quenching BBr₃). The pH was adjusted to pH=7 by adding K₂CO₃.CH₂Cl₂ was added. The mixture was washed with water (2×). The organic layer was separated, and the solvent was evaporated under reduced pressure. The residue was purified by high-performance liquid chromatography. The product fractions were collected and sodium chloride was added until saturation. K₂CO₃ was added to bring pH to value 9. CH₂Cl₂ was added. The organic layer was separated, and the solvent was evaporated under reduced pressure. The residue was dried (vacuum oven), yielding 0.350 g of compound (93).

Example B.15

Preparation of

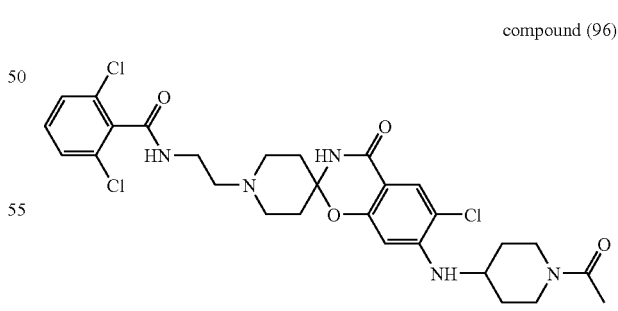

compound (96)

Compound (83) (0.0110 mol) was dissolved in CH₂Cl₂ (400 ml). Acetyl acetate (0.0100 mol) and Et₃N (6.8 ml) were added. The reaction mixture was stirred for 1 hour at room temperature. The reaction mixture was washed with water, then with a saturated aqueous Na₂CO₃ solution and again with water. The organic layer was separated, dried, filtered and the solvent was evaporated, yielding compound (96).

Compound (100) was prepared analogously starting from compound (99).

Example B.16

Preparation of compound (97)

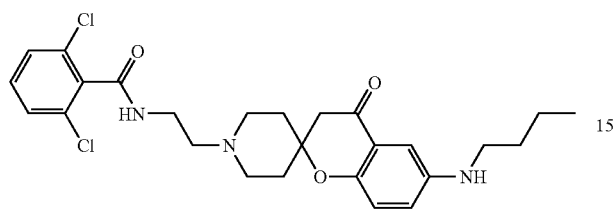

$K_2CO_3$ (0.0056 mol) and 1-bromobutane (0.0022 mol) were added to a solution of compound (121) (0.0022 mol) in DMF (20 ml) and the reaction mixture was stirred for 12 hours at 80° C. The reaction mixture was poured in water (30 ml). This mixture was extracted with $CH_2Cl_2$. The separated organic layer was washed with water. The separated organic layer's solvent was evaporated. The residue was purified by high-performance liquid chromatography. The product fractions were collected and the solvent was evaporated, yielding 0.6 g compound (97).

Example B.17

Preparation of compound (151)

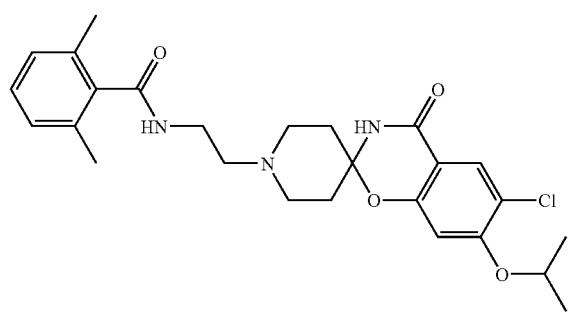

Molecular sieves 4 Å (15 g) and then PTSA (0.0013 mol) were added to a solution of intermediate (17) (0.0132 mol) and intermediate (82) (0.0158 mol) in toluene (30 ml) and was stirred and refluxed for 12 hours at 50° C. Toluene was evaporated (vacuum). The residue was dissolved in $CH_2Cl_2$. The mixture was washed with NaOH (2N) and then washed with brine. The separated organic layer was dried ($Na_2SO_4$), filtered and the filtrate's solvent was evaporated. The residue was purified by column chromatography over silica (eluent: petroleum ether/EtOAc/(7N $NH_3$ in methanol) 100/100/1 and 0/50/1). The product fractions were collected and the solvent was evaporated. The residue was crystallized from EtOH and the precipitate was filtered off, yielding 2.2 g of compound (151).

Compound (135) was prepared analogously using intermediates (8) and (98).

Example B.18

Preparation of compound (106)

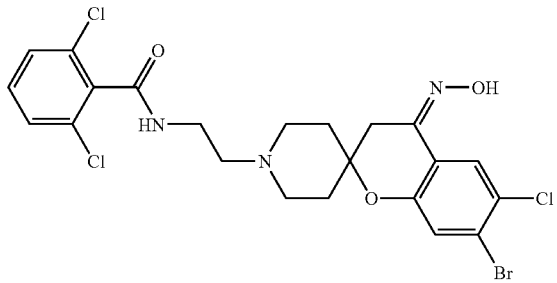

A mixture of compound (87) (0.0005 mol), $NH_2OH.HCl$ (0.0009 mol) and NaOAc (0.075 g) in EtOH was stirred and refluxed for 4 hours. After the reaction was completed, the reaction mixture was cooled to room temperature. The precipitate was filtered off and crystallized from methanol, yielding compound (106).

Example B.19

Preparation of compound (108)

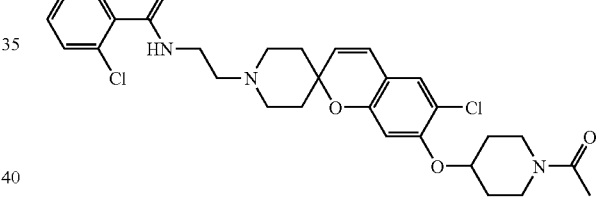

Compound (104) (0.0003 mol) was dissolved in THF (10 ml) and then 1N HCl (0.8 ml) was added The reaction mixture was stirred overnight at 70° C. The reaction was alkalized with $NaHCO_3$, extracted and washed with water. The mixture was dried over isolute and the solvent was evaporated, yielding compound (108).

Example B.20

Preparation of compound (117)

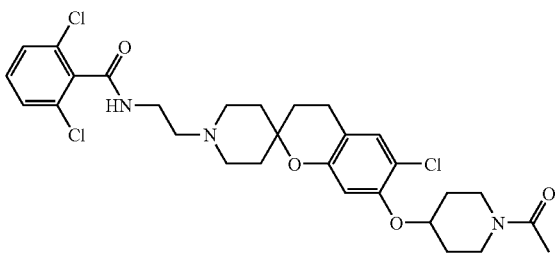

Compound (108) (0.0015 mol) was hydrogenated using platinum-on-carbon (5%) (0.3 g) in methanol (40 ml). After uptake of hydrogen (1 equivalent), the reaction mixture was filtrated. The solvent was evaporated. The product was purified by reversed-phase high-performance liquid chromatography. The residue was extracted ($CH_2Cl_2/H_2O$), dried and filtered and the solvent was evaporated, yielding compound (117).

Example B.21

Preparation of

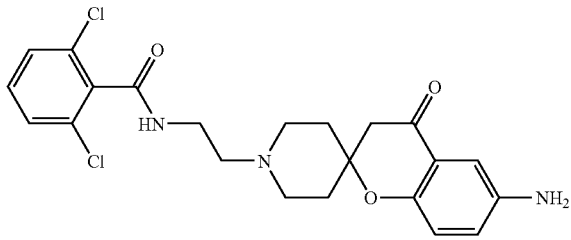

compound (121)

A mixture of compound (81) in methanol was hydrogenated for 12 hours with Raney Nickel as catalyst. After uptake of hydrogen (3 equivalents) the catalyst was filtered off and the solvent was evaporated, yielding 0.92 g of compound (121).

Example B.22

Preparation of

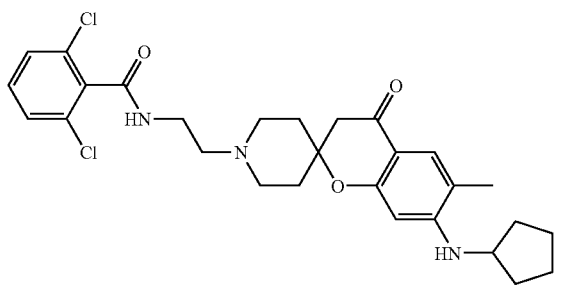

compound (127)

A mixture of compound (120) (0.0012 mol) and iodocyclopentane (0.0050 mol) was heated in a microwave oven for 40 minutes at 180° C. The crude residual reaction mixture was partitioned between $CH_2Cl_2$ (+methanol) and an aqueous ammonia solution. The organic layer was separated, dried ($MgSO_4$), filtered and the solvent evaporated. The reaction was done 4 times. The residue was purified by high-performance liquid chromatography. The product fractions were collected and part of the solvent was evaporated. The concentrate was partitioned between $CH_2Cl_2$ and water (with a drop of ammonia). The organic layer was separated, dried ($MgSO_4$), filtered and the solvent was evaporated. The residue was suspended in DIPE, filtered off and dried under vacuum at 50° C., yielding 0.09 g of compound (127).

Example B.23

Preparation of

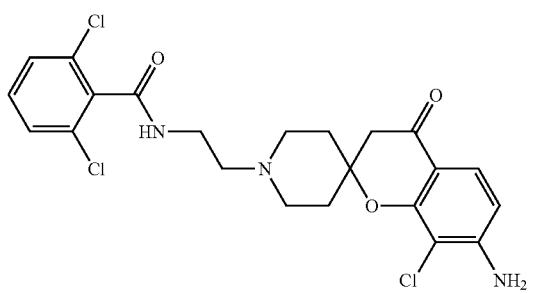

compound (130)

To a mixture of compound (41) (0.0020 mol), sodium chloride (0.482 g) and oxone (0.0020 mol) in 2-propanone (150 ml), water (150 ml) was added. The mixture was stirred at room temperature over the weekend. The solvent was evaporated. The product was extracted with $CH_2Cl_2$, few drops of methanol and an aqueous $NaHCO_3$ solution. The organic layer was separated, dried, filtered and the solvent was evaporated. The residue was purified by column chromatography ($CH_2Cl_2$ to 90/10 $CH_2Cl_2/CH_3OH(NH_3)$). The desired fractions were collected and the solvent was evaporated, yielding compound (130).

Example B.24

Preparation of

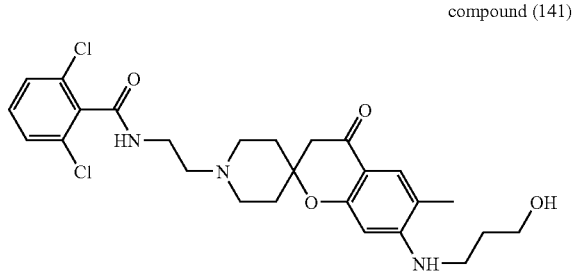

compound (141)

A mixture of intermediate (113) (0.0043 mol), intermediate (100) (0.0050 mol) and DIPEA (0.0055 mol) in DMF (25 ml) was stirred for 24 hours at room temperature. The solvent was evaporated. The residue was partitioned between $CH_2Cl_2$ and water. The organic layer was separated, dried ($MgSO_4$), filtered and the solvent was evaporated. The residue was purified by column chromatography over silica gel (eluent: $CH_2Cl_2/(CH_3OH/NH_3)$ 97/3). The product fractions were collected and the solvent was evaporated. The residue was suspended in DIPE, filtered off and dried (vacuum, 40° C.), yielding 0.4 g of compound (141).

Example B.25

Preparation of compound (180)

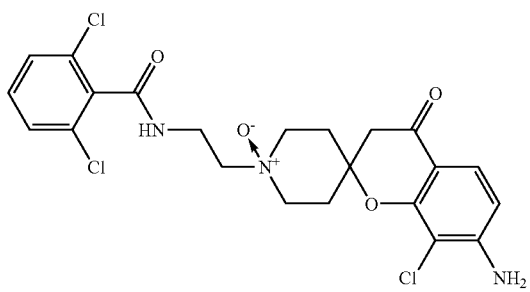

To a mixture of compound (40), sodium chloride (0.157 g) and oxone (0.0007 mol) in acetone (50 ml), water (50 ml) was added. The mixture was stirred at room temperature for 3 hours. The solvent was evaporated. The product was extracted with $CH_2Cl_2$, few drops of methanol and $NaHCO_3$. The organic layer was separated, dried, filtered and the solvent was evaporated. The residue was purified with column chromatography (eluent: $CH_2Cl_2$ to 90/10 $CH_2Cl_2/CH_3OH$ ($NH_3$)) The desired fractions were collected and the solvent was evaporated, yielding compound (180).

Example B.26

Preparation of compound (181)

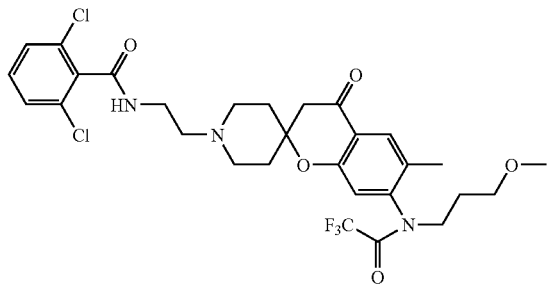

A solution of compound (123) (0.0016 mol) in DMF (5 ml) was stirred under nitrogen atmosphere. Sodium hydride (0.0016 mol) was added and the reaction mixture was stirred at 50° C. for 10 minutes. 1-Bromo-3-methoxypropane (0.0027 mol) was added and the resultant reaction mixture was stirred for one hour at 70° C. The reaction mixture was cooled. The solvent was evaporated. The residue was partitioned between $CH_2Cl_2$ and water. The organic layer was separated, dried ($MgSO_4$), filtered and the solvent was evaporated, yielding 0.8 g of compound (181).

Example B.27

Preparation of compound (133)

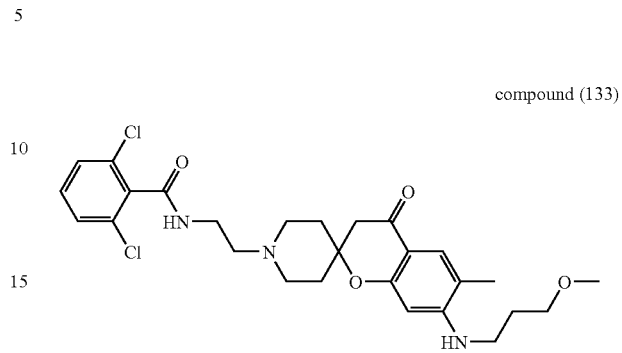

Compound (120) (0.0011 mol) and 1-bromo-3-methoxypropane (0.5 g) was stirred at 180° C. for 30 minutes. The mixture was cooled. The mixture was partitioned between $CH_2Cl_2$ (+methanol) and water. The organic layer was separated, dried ($MgSO_4$), filtered and the solvent was evaporated. The residue was purified by column chromatography over silica gel (eluent: $CH_2Cl_2/(CH_3OH/NH_3)$ 98/2). The product fractions were collected and the solvent was evaporated. The residue was purified by reversed-phase high-performance liquid chromatography. The product fractions were collected and the solvent was evaporated. The residue was stirred in water (+drop $NH_3$)/$CH_2Cl_2$. The organic layer was separated, dried ($MgSO_4$), filtered and the solvent was evaporated. The residue was suspended in DIPE, and filtered off. The fraction was resubmitted to high-performance liquid chromatography. The product fractions were collected and the solvent was evaporated. The residue was crystallized as an oxalate from ethyl acetate, then filtered and dried under vacuum at 50° C., yielding 0.035 g of compound (133).

Example B.28

Preparation of compound (208)

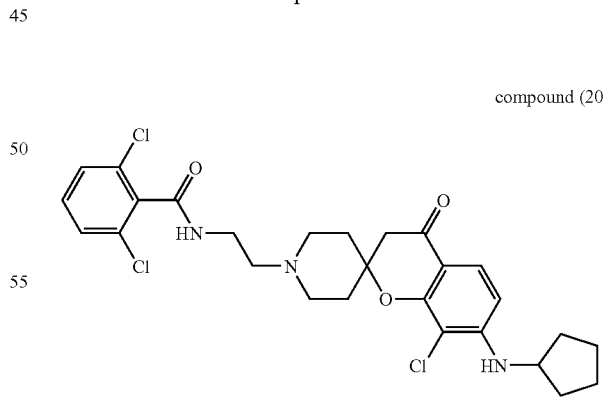

Compound (129) (0.4 mmol) was dissolved in $CH_3CN$ (5 ml). N-chlorosuccinimide (0.051 g) was added. The reaction mixture was stirred at 65° C. for 8 hours and further stirred at room temperature overnight. The solvent was evaporated, the mixture was extracted ($CH_2Cl_2/H_2O$, $NaHCO_3$). The organic phase was dried, filtered and the solvent was evaporated. The

Example B.29

Preparation of compound (189)

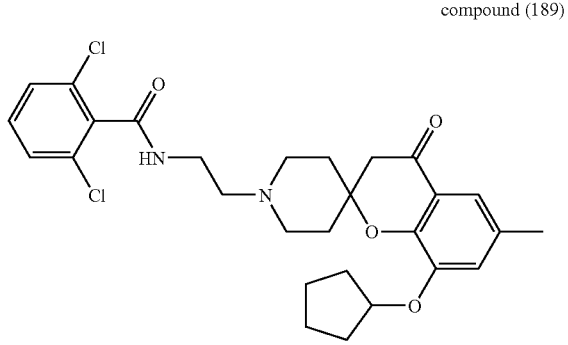

Bromo-cyclopentane (4.856 mmol) was added to a mixture of compound (235) (3.237 mmol), $K_2CO_3$ (4.208 mmol) and potassium iodide (catalyst) in DMF (40 ml). The reaction mixture was stirred for 22 hours at 60° C. More bromo-cyclopentane (0.1 ml) was added and the reaction mixture was stirred for another 3 hours. After cooling to room temperature, water was added. The reaction mixture was extracted ($CH_2Cl_2/H_2O$). The organic layers were dried, filtered and the solvent was evaporated. The mixture was purified with column chromatography ($CH_2Cl_2/CH_3OH(NH_3)$ 96/4). The desired fractions were collected, the solvent was evaporated (1 g). The residue was crystallised from DIPE, yielding 530 mg of compound (189).

Example B.30

Preparation of compound (239)

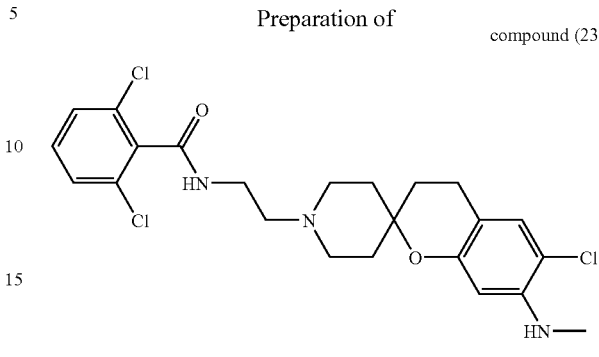

A mixture of compound (233) (1.4 g) and paraform (0.090 g) in $CH_3OH$ (40 ml) was hydrogenated with Pt/C 5% (0.05 g) as a catalyst in the presence of thiophene solution (0.1 ml). After uptake of hydrogen (1 equivalent), the catalyst was filtered off and the filtrate was evaporated. The residue was purified with high performance column chromatography. The solvent was evaporated. The second fraction needed to be purified again with high performance column chromatography using method A. The solvent was evaporated. The residue was suspended in DIPE, filtered off and dried, yielding 77 mg of compound (239).

Example B.31

Preparation of compound (222)

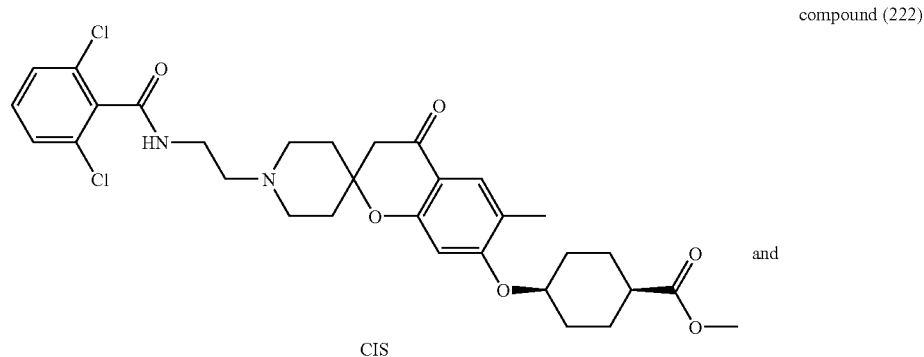

and

CIS compound (199)

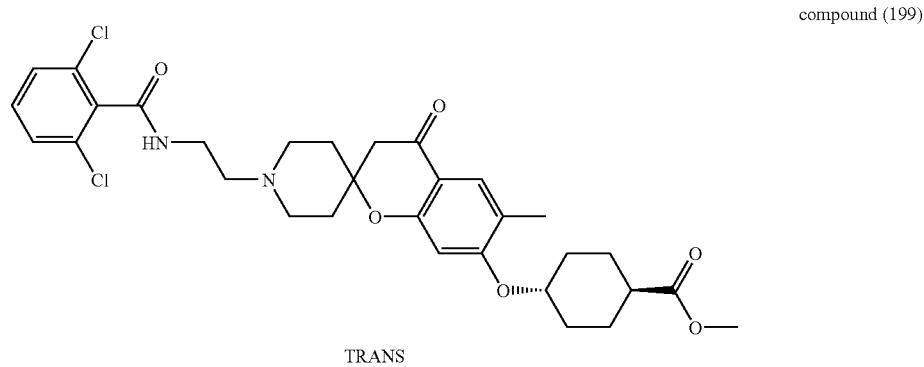

TRANS

A mixture of 2,6-dichloro-N-[2-(4-oxo-1-piperidinyl) ethyl]-benzamide (9 mmol), intermediate (114) (12.485 mmol) and pyrrolidine (18 mmol) in CH$_3$OH (300 ml) was stirred at 80° C. for 48 hours and cooled. The solvent was evaporated. The residue was extracted in CH$_2$Cl$_2$/H$_2$O. The organic layer was separated, dried (MgSO$_4$), filtered and the solvent was evaporated. The residue was purified by chromatography using method A. Two fractions were collected and the solvent was evaporated. Fraction 1 was crystallized as an oxalate in ethyl acetate, filtered and dried under vacuum at 50° C., yielding 305 mg of compound (222). Fraction 2 was crystallized as an oxalate in ethyl acetate, filtered and dried under vacuum at 50° C., yielding 147 mg of compound (199).

Example B.32

Preparation of compound (223)

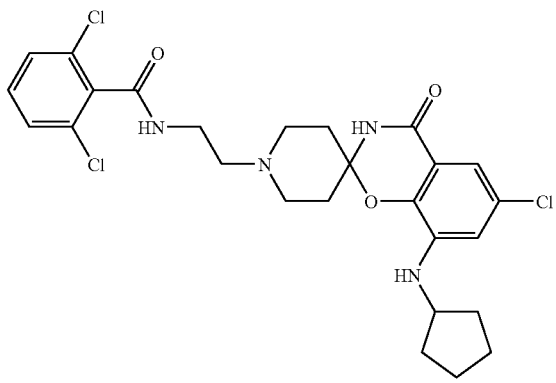

The reaction was carried out under N2 atmosphere. Compound (226) (5.58 mmol) was dissolved in acetic acid (dry glacial, 30 ml) and cyclopentanone (39.06 mmol) was added. The mixture was stirred at 25° C. for 2 hours. NaBH$_3$CN (33.5 mmol) was added portionwise. The reaction mixture was stirred at 25° C. for 2 hours. Another 500 mg of cyclopentanone was added and the reaction was continued to stir for 1 hour at 25° C. Water (30 ml) and CH$_2$Cl$_2$ (100 ml) were added and this solution was adjusted to pH=8 by solid Na$_2$CO$_3$. Then this mixture was filtered to remove inorganic salt. The water phase was extracted again with CH$_2$Cl$_2$. The organic layers were combined, washed by brine and water, dried over Na$_2$SO$_4$, filtered and evaporated. The residue was purified by preparative high performance liquid chromatography over RP-18 (eluent: CH$_3$CN/H$_2$O from 45/55 to 85/15 v/v with 0.1% CF$_3$COOH). The desired fractions were collected, basified to pH=8 with NaHCO$_3$ and extracted twice by ethyl acetate. The organic layers were combined, washed twice with water, dried over Na$_2$SO$_4$, filtered and evaporated to afford pure product. The product was further dried in vacuum oven at 60° C. for 12 hours, yielding 1.16 g of compound (223).

Example B.33

Preparation of compound (205)

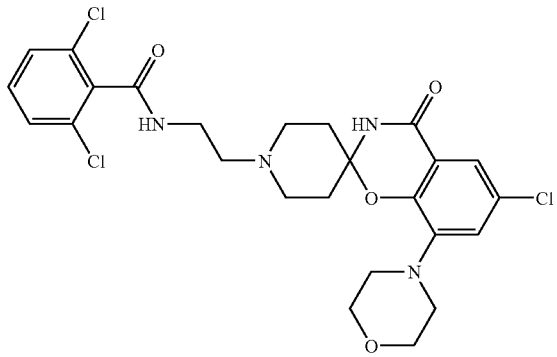

The reaction was carried out in a microwave oven. A mixture of compound (226) (6.20103 mmol), 1,1'-oxybis[2-bromo-ethane (31.0051 mmol), potassium carbonate (12.4021 mmol) and sodium iodide (0.6201 mmol) in DMF (30 ml) was stirred at 140° C. for 40 minutes. Potassium carbonate was filtered off The filtrate was concentrated and dissolved in CH$_3$OH and de-colored by active carbon. The mixture was filtered and concentrated. The residue was purified by preparative high performance liquid chromatography (CH$_3$CN/H$_2$O from 15/85 to 40/60 with 0.1% CF$_3$COOH). The product was basified with solid Na$_2$CO$_3$ until pH to 9, and the CH$_3$CN was evaporated. The resulted precipitate was filtered off and washed with water (2 times 10 ml), filtered and then re-crystallization from CH$_3$CN. The precipitate was filtered off and dried in vacuum at 80° C. for 1 hour, yielding 563.36 mg of compound (205).

Tables F-1, F-2, F-3, F-4 and F-5 list the compounds that were prepared according to one of the above Examples.

TABLE F-1

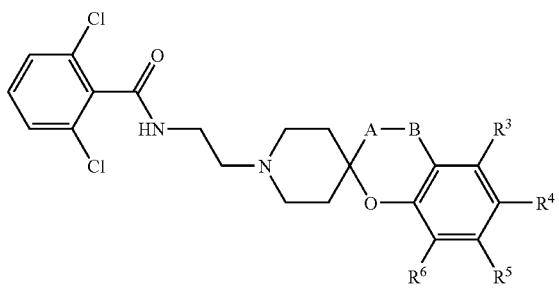

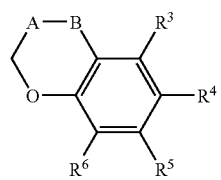

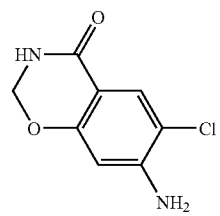

Co. No. 1; Ex. B. 1

TABLE F-1-continued
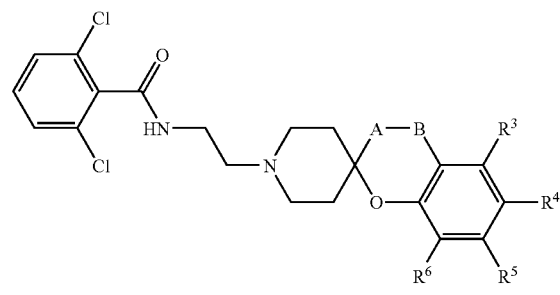
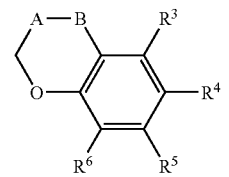
TABLE F-1-continued
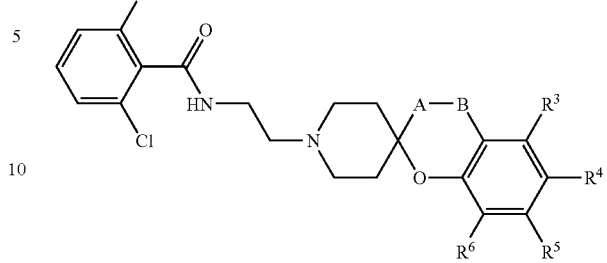
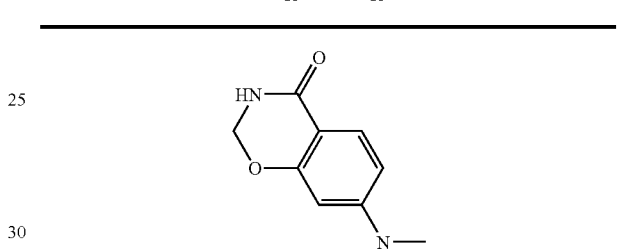
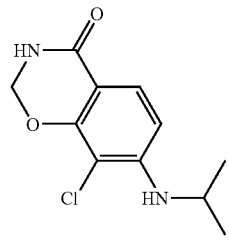
Co. No. 2; Ex. B. 2
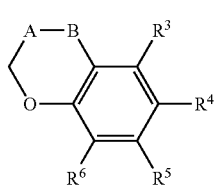
Co. No. 6; Ex. B. 3
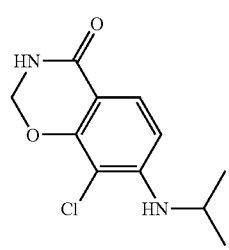
Co. No. 3; Ex. B. 3
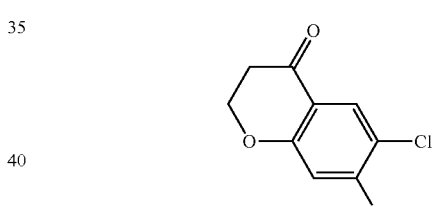
Co. No. 7; Ex. B. 11
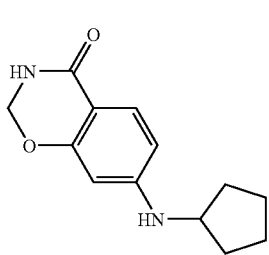
Co. No. 4; Ex. B. 3
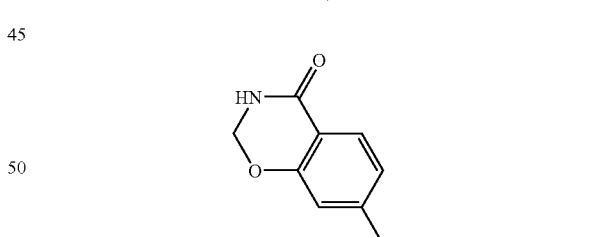
Co. No. 8; Ex. B. 3
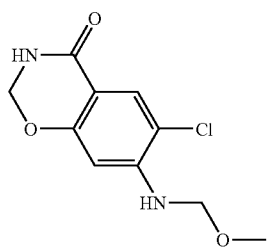
Co. No. 5; Ex. B. 3
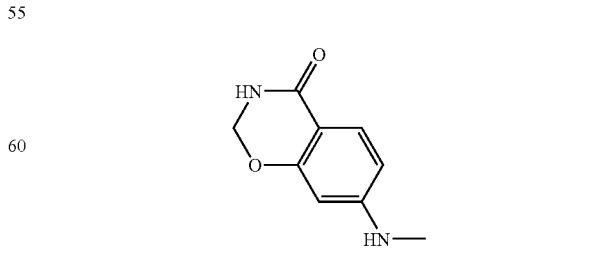
Co. No. 9; Ex. B. 3

TABLE F-1-continued
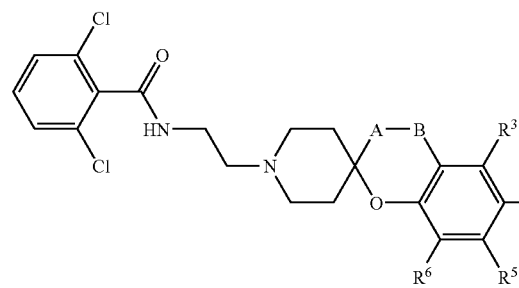
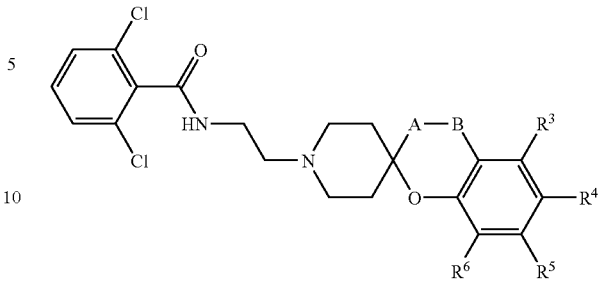
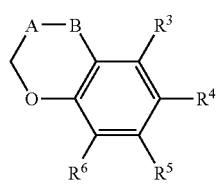
Co. No. 10; Ex. B. 5
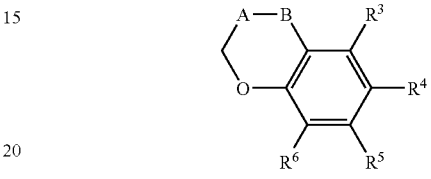
Co. No. 14; Ex. B. 3
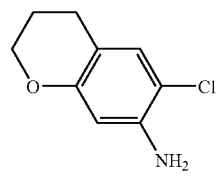
Co. No. 11; Ex. B. 3
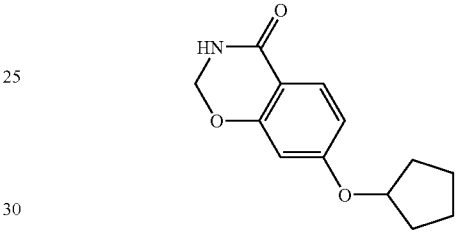
Co. No. 15; Ex. B. 11
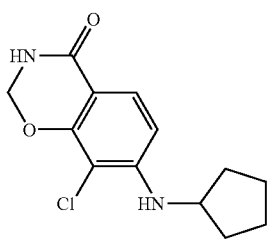
Co. No. 12; Ex. B. 3
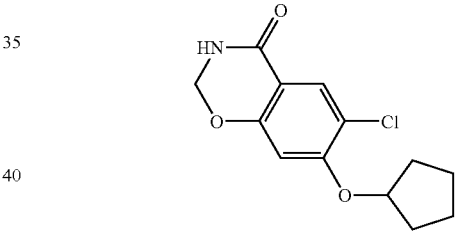
Co. No. 16; Ex. B. 3
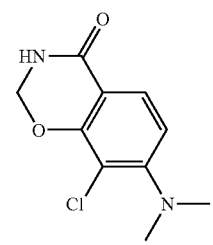
Co. No. 13; Ex. B. 3
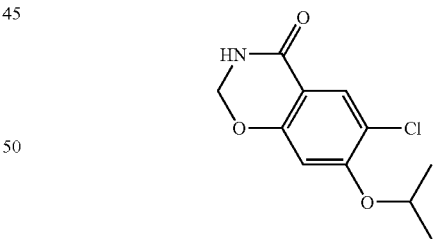
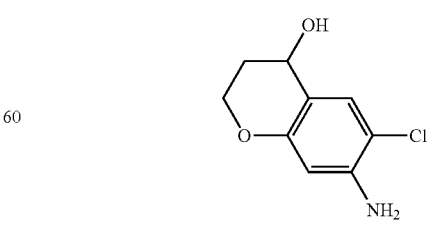
Co. No. 17; Ex. B. 4

TABLE F-1-continued
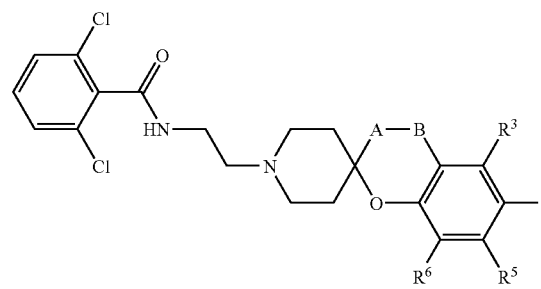
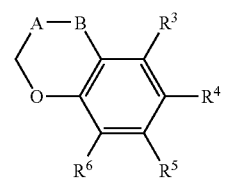
Co. No. 18; Ex. B. 11
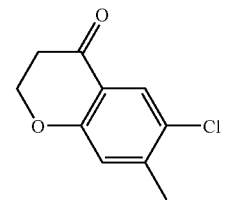
Co. No. 19; Ex. B. 3
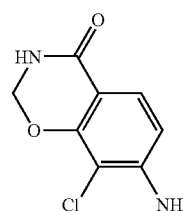
Co. No. 20; Ex. B. 3
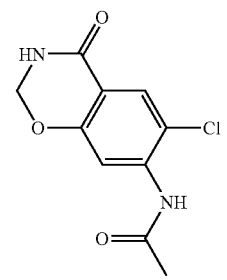
Co. No. 21; Ex. B. 3
TABLE F-1-continued
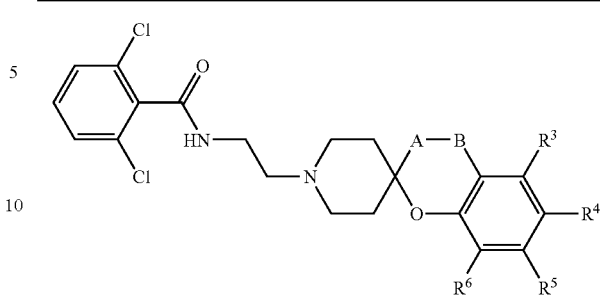
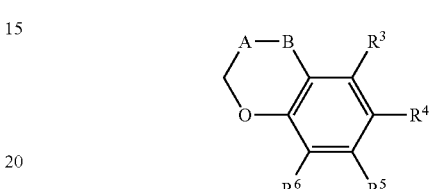
Co. No. 22; Ex. B. 6
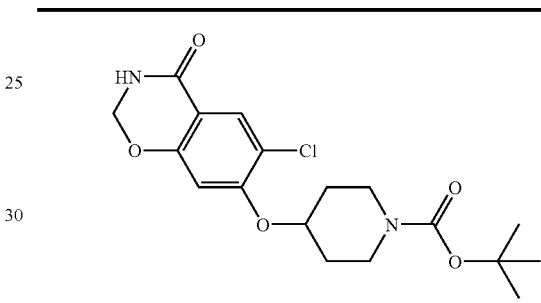
Co. No. 23; Ex. B. 7
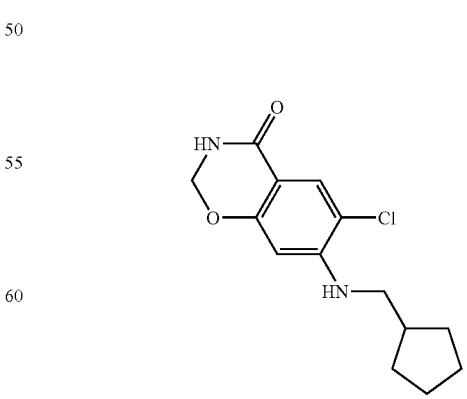
Co. No. 24; Ex. B. 3

TABLE F-1-continued
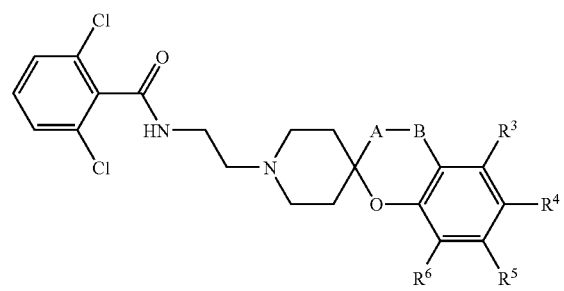
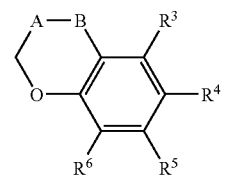
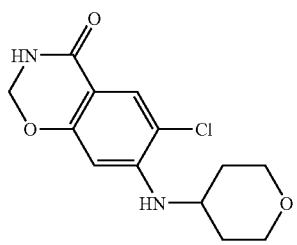
Co. No. 25; Ex. B. 3
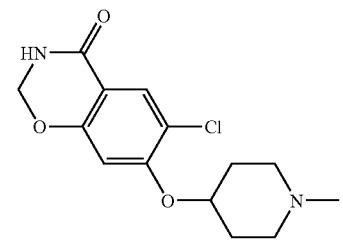
Co. No. 26; Ex. B. 8
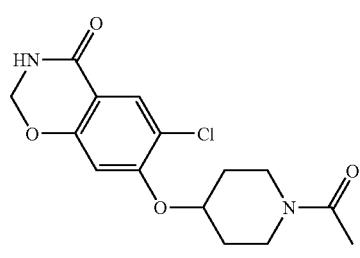
Co. No. 27; Ex. B. 9
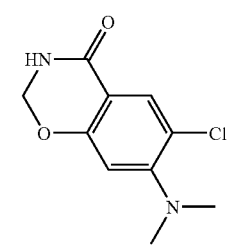
Co. No. 28; Ex. B. 3
TABLE F-1-continued
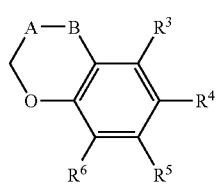
Co. No. 29; Ex. B. 3
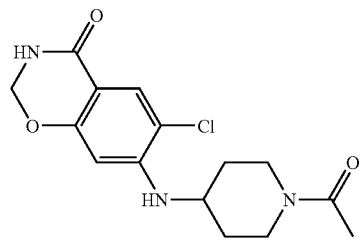
Co. No. 30; Ex. B. 3
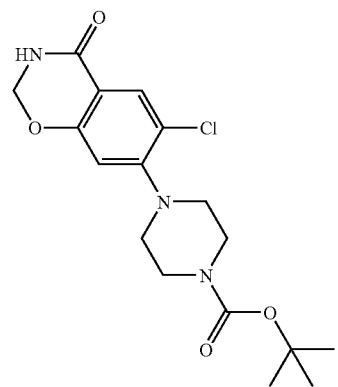
Co. No. 31; Ex. B. 3

TABLE F-1-continued
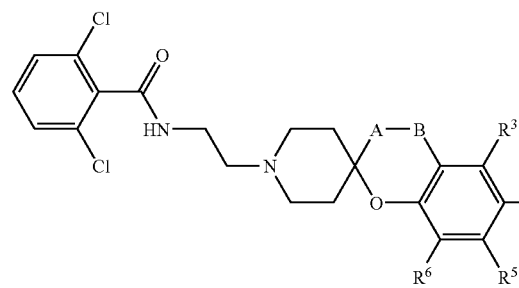
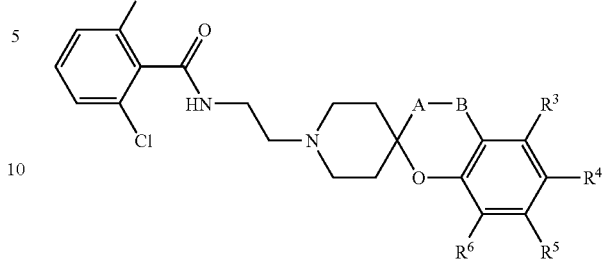
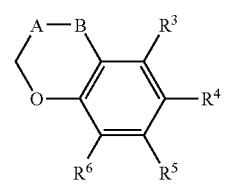
Co. No. 32; Ex. B. 7
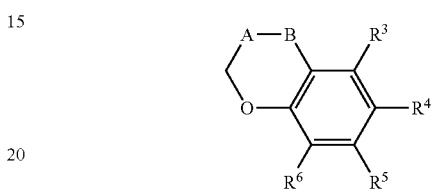
Co. No. 35; Ex. B. 8
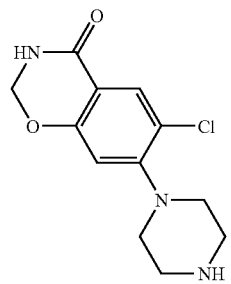
Co. No. 33; Ex. B. 3
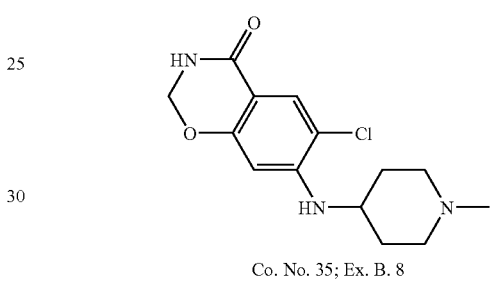
Co. No. 36; Ex. B. 11
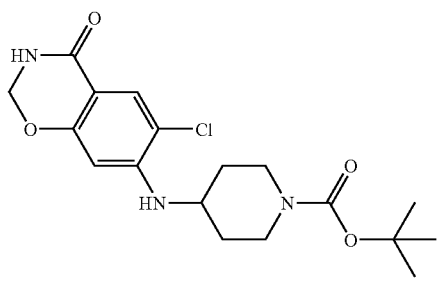
Co. No. 34; Ex. B. 7
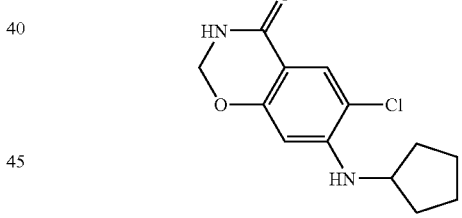
Co. No. 37; Ex. B. 3

TABLE F-1-continued
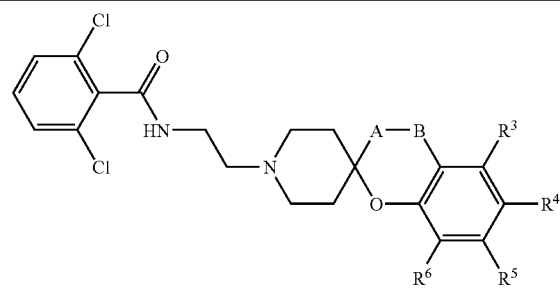
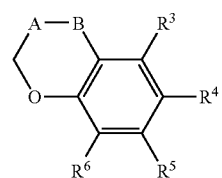
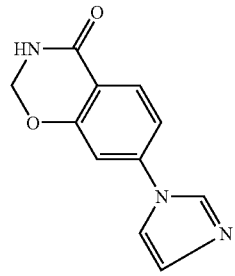
Co. No. 38; Ex. B. 3
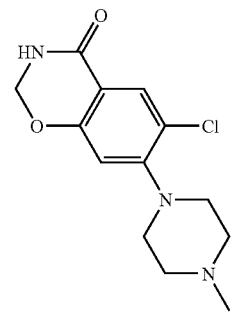
Co. No. 39; Ex. B. 8
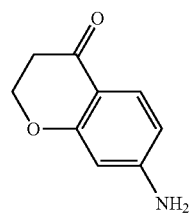
Co. No. 40; Ex. B. 11
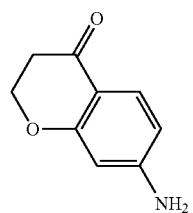
Co. No. 41; Ex. B. 3; ·HCl
TABLE F-1-continued
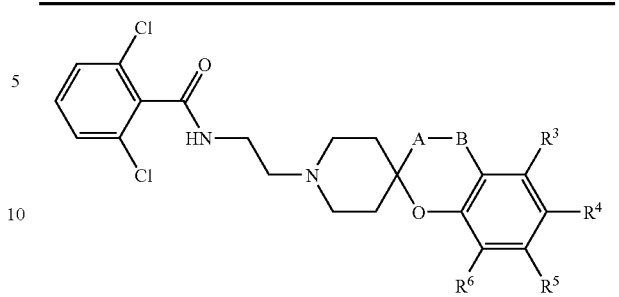
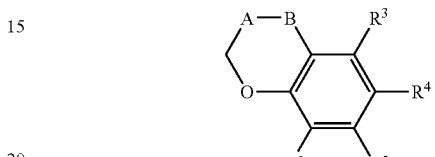
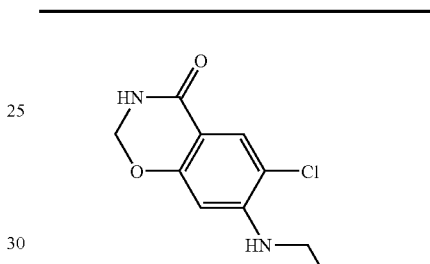
Co. No. 42; Ex. B. 3
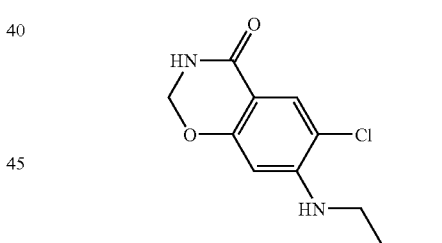
Co. No. 43; Ex. B. 10
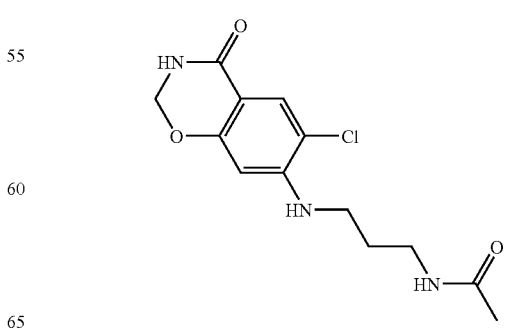
Co. No. 44; Ex. B. 3

TABLE F-1-continued
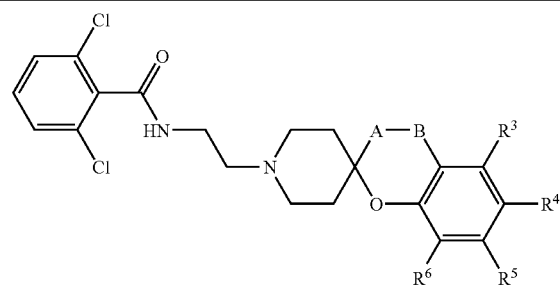
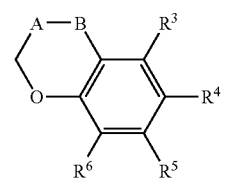
Co. No. 45; Ex. B. 11
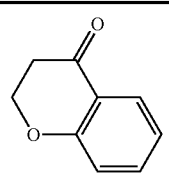
Co. No. 46; Ex. B. 11
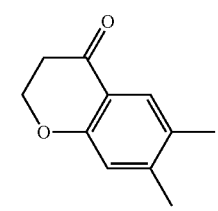
Co. No. 47; Ex. B. 11
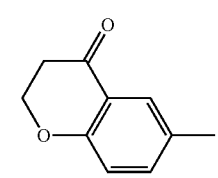
Co. No. 48; Ex. B. 11
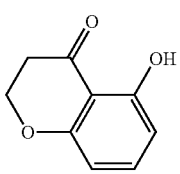
Co. No. 49; Ex. B. 11
TABLE F-1-continued
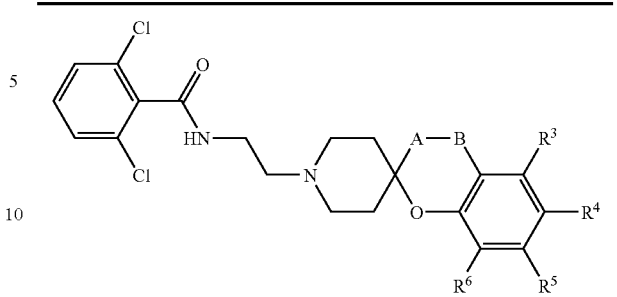
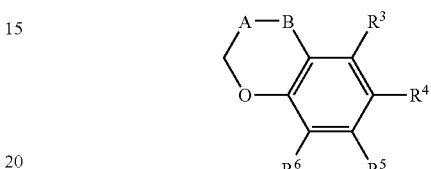
Co. No. 50; Ex. B. 11
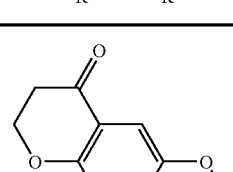
Co. No. 51; Ex. B. 11
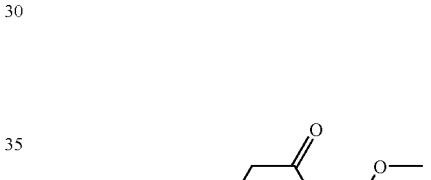
Co. No. 52; Ex. B. 11
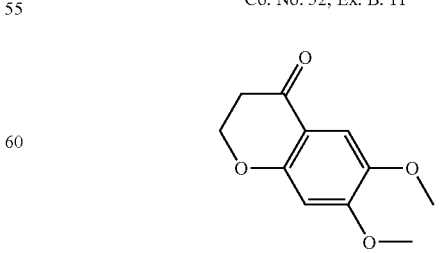
Co. No. 53; Ex. B. 11

TABLE F-1-continued
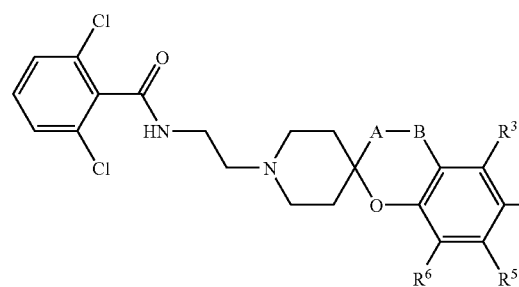
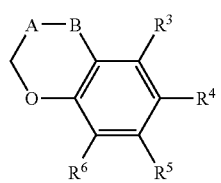
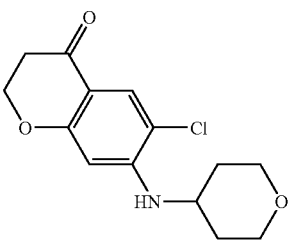
Co. No. 54; Ex. B. 11
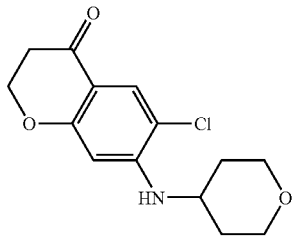
Co. No. 55; Ex. B. 11; •HCl
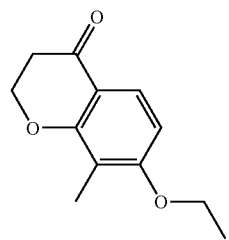
Co. No. 56; Ex. B. 11
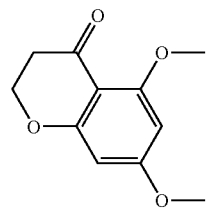
Co. No. 57; Ex. B. 11
TABLE F-1-continued
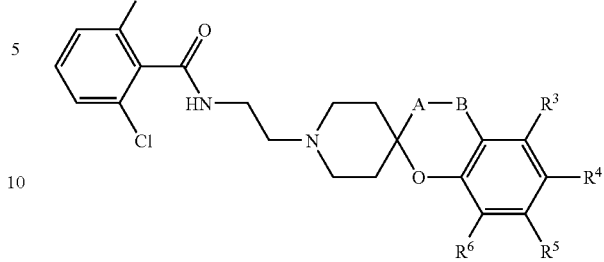
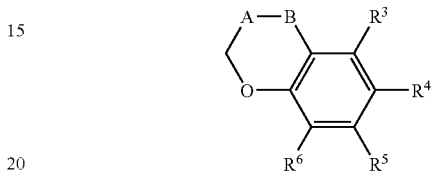
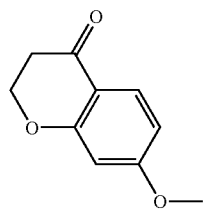
Co. No. 58; Ex. B. 11
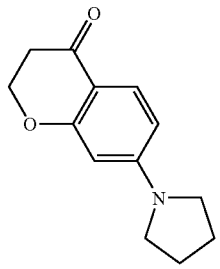
Co. No. 59; Ex. B. 11
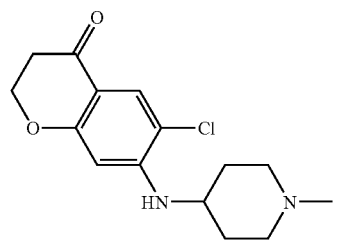
Co. No. 60; Ex. B. 11
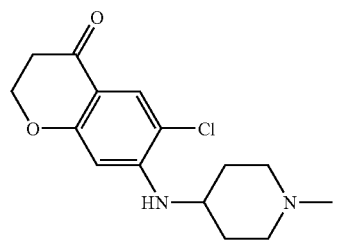
Co. No. 61; Ex. B. 11; •HCl TABLE F-1-continued
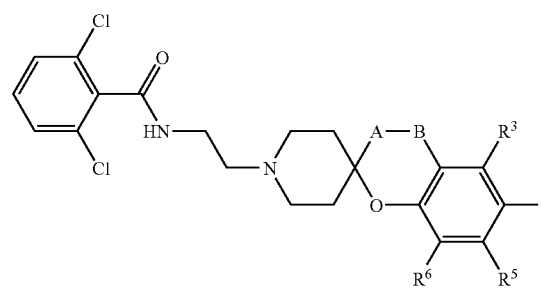
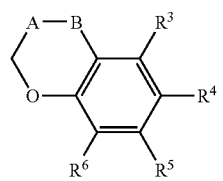
Co. No. 62; Ex. B. 11; •HCl
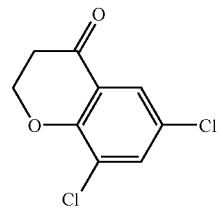
Co. No. 63; Ex. B. 11
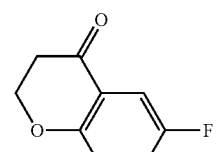
Co. No. 64; Ex. B. 11
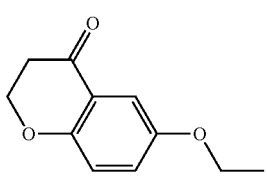
Co. No. 65; Ex. B. 11
TABLE F-1-continued
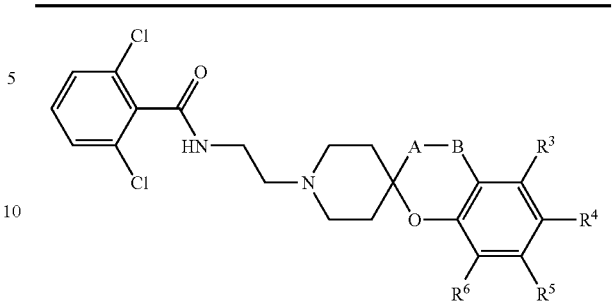
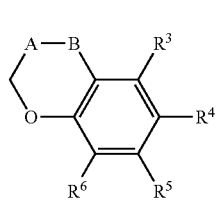
Co. No. 66; Ex. B. 12; •HCl
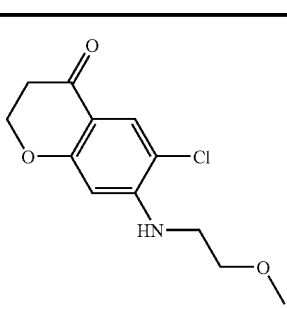
Co. No. 67; Ex. B. 11; •HCl
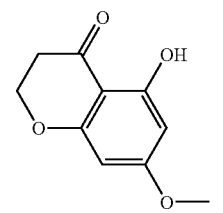
Co. No. 68; Ex. B. 11; •HCl
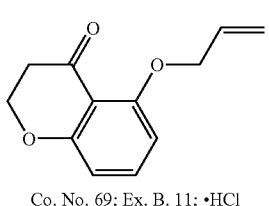
Co. No. 69; Ex. B. 11; •HCl TABLE F-1-continued
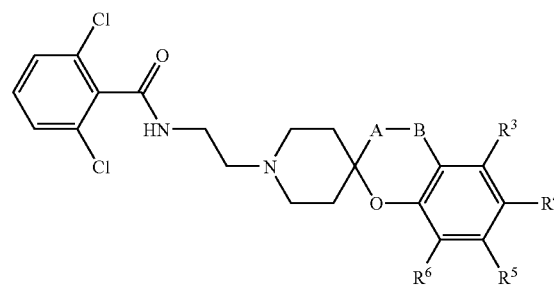
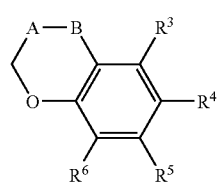
Co. No. 70; Ex. B11.; •HCl
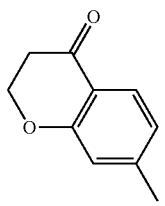
Co. No. 71; Ex. B. 11; •HCl
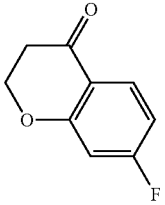
Co. No. 72; Ex. B. 11; •HCl
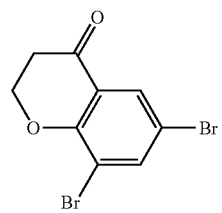
Co. No. 73; Ex. B. 11; •3HCl
TABLE F-1-continued
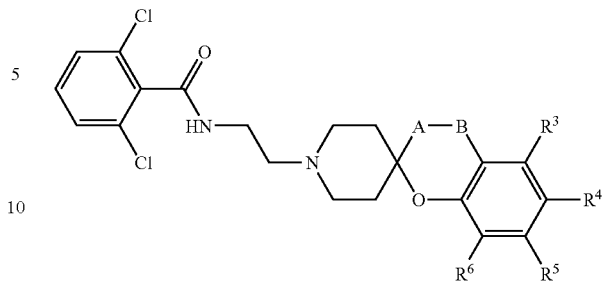
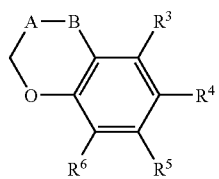
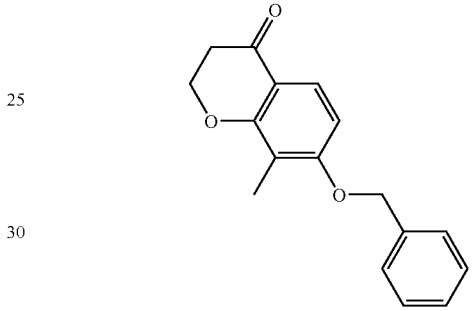
Co. No. 74; Ex. B. 11
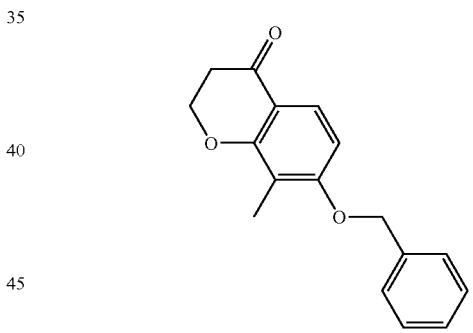
Co. No. 75; Ex. B. 11; •HCl
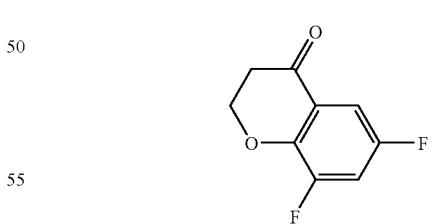
Co. No. 76; Ex. B. 11; •HCl
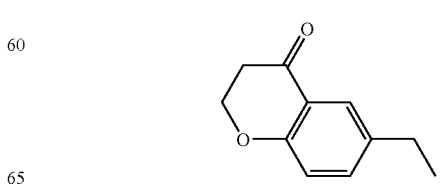
Co. No. 77; Ex. B. 11; •HCl TABLE F-1-continued
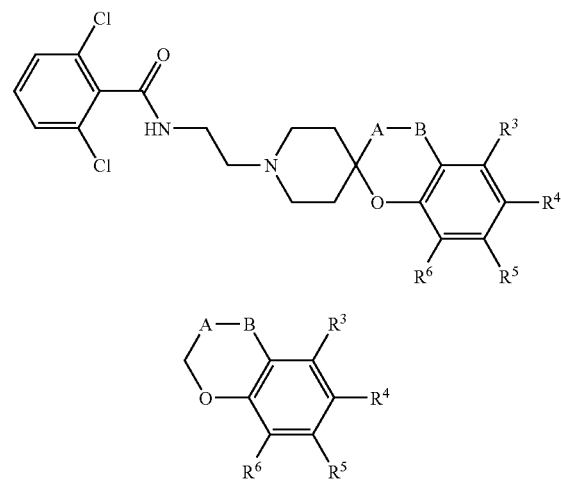
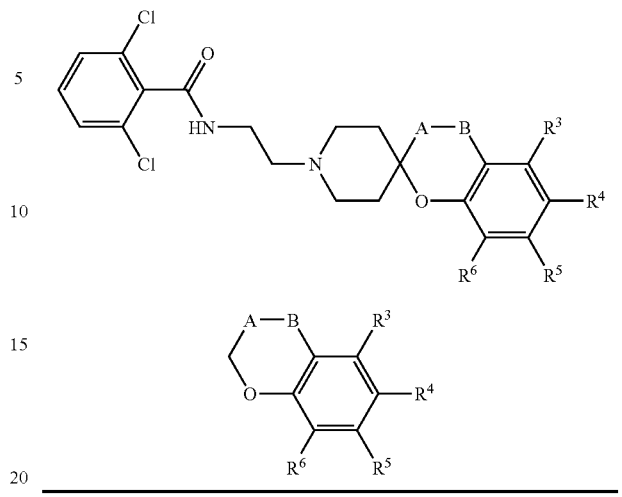
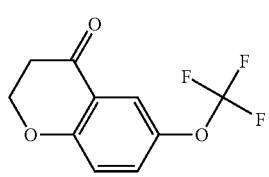
Co. No. 78; Ex. B. 11; •HCl
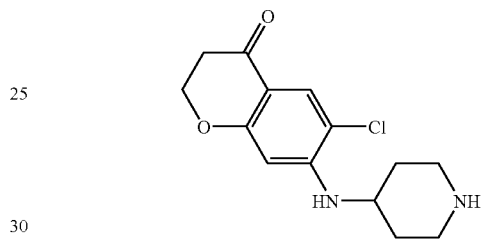
Co. No. 83; Ex. B. 7
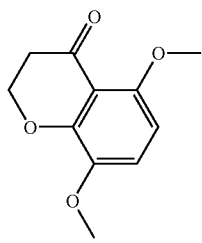
Co. No. 79; Ex. B. 11; •HCl
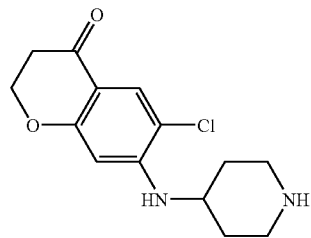
Co. No. 84; Ex. B. 7; •2HCl
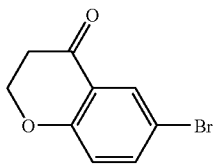
Co. No. 80; Ex. B. 11; •HCl
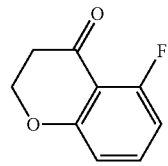
Co. No. 85; Ex. B. 11
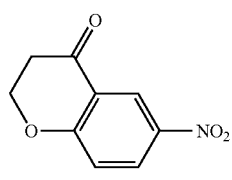
Co. No. 81; Ex. B. 11
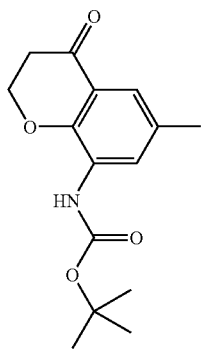
Co. No. 86; Ex. B. 11
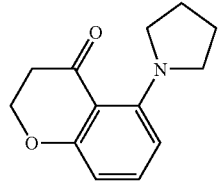
Co. No. 82; Ex. B. 11

TABLE F-1-continued
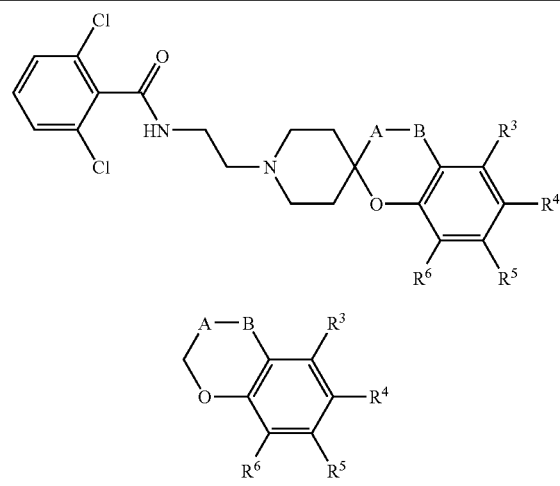
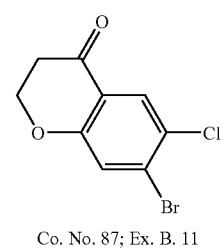
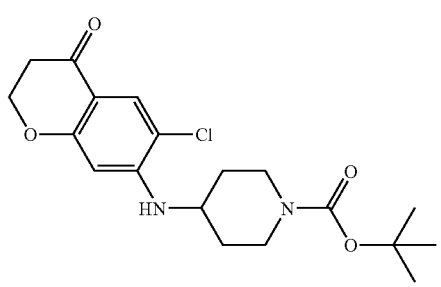
Co. No. 87; Ex. B. 11
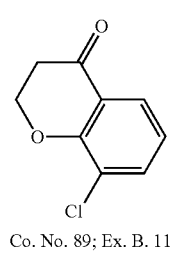
Co. No. 88; Ex. B. 12
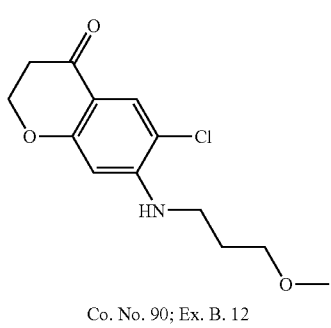
Co. No. 89; Ex. B. 11
Co. No. 90; Ex. B. 12
TABLE F-1-continued
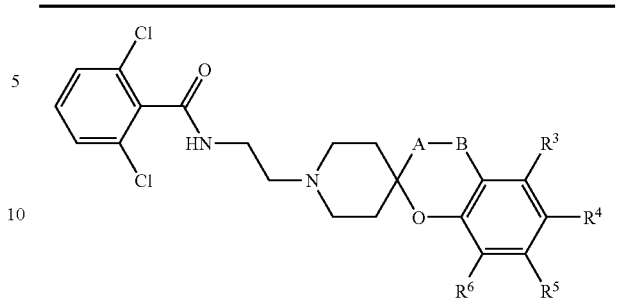
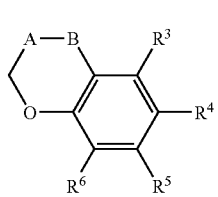
Co. No. 91; Ex. B. 13; •HCl
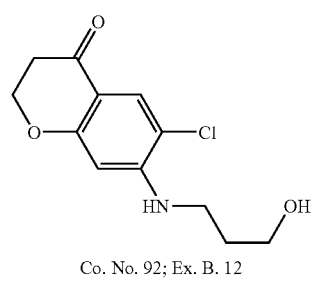
Co. No. 92; Ex. B. 12
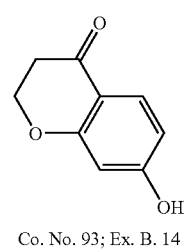
Co. No. 93; Ex. B. 14
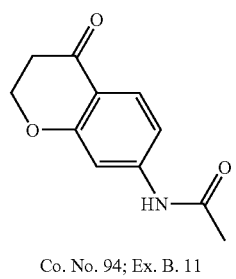
Co. No. 94; Ex. B. 11

TABLE F-1-continued
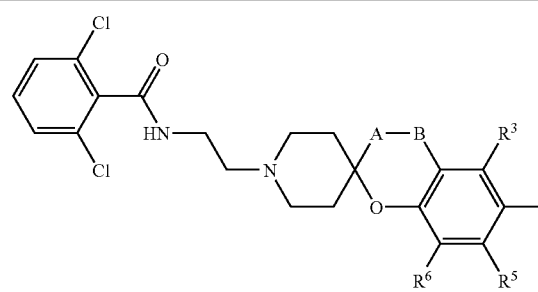
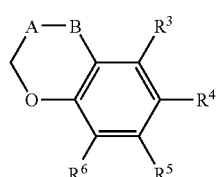
| | |
|---|---|
| 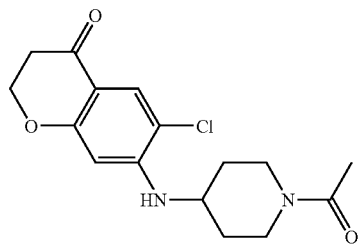 | 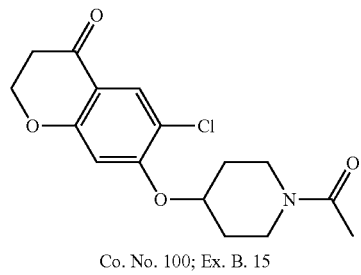 |
| Co. No. 95; Ex. B. 12 | Co. No. 99; Ex. B. 7 |
| 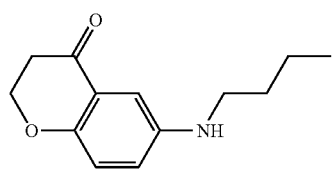 | 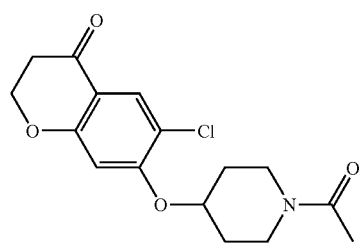 |
| Co. No. 96; Ex. B. 15 | Co. No. 100; Ex. B. 15 |
| 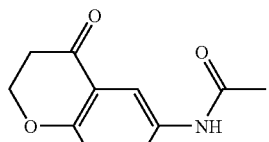 | |
| Co. No. 97; Ex. B. 16 | |
TABLE F-1-continued
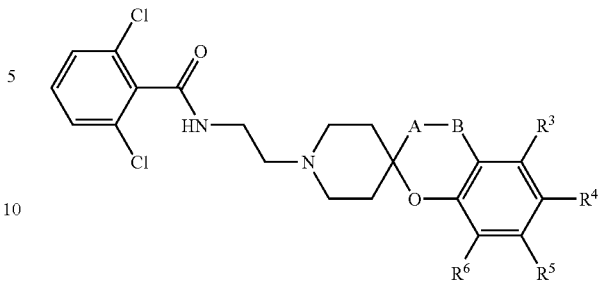
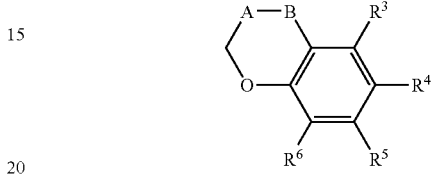
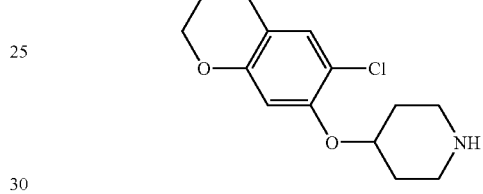
Co. No. 101; Ex. B. 15; •2C$_2$H$_2$O$_4$
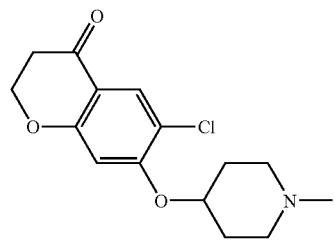
Co. No. 98; Ex. B. 15
Co. No. 102; Ex. B. 8

TABLE F-1-continued
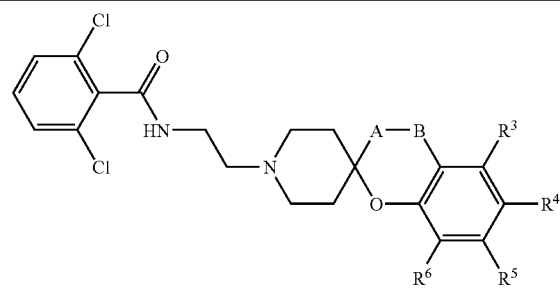
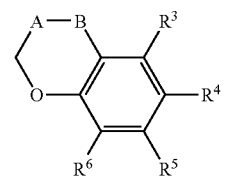
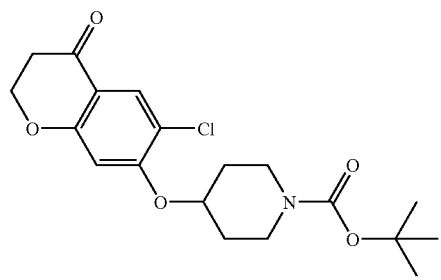
Co. No. 103; Ex. B. 11
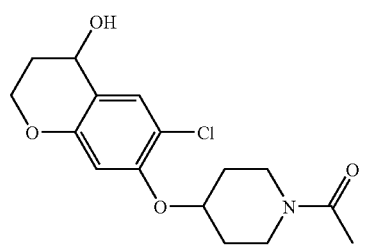
Co. No. 104; Ex. B. 4
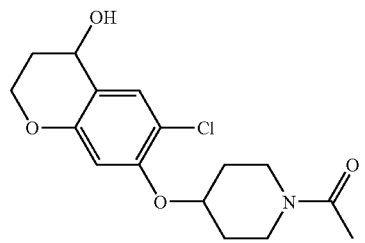
Co. No. 105; Ex. B. 4;
•1.5C$_2$H$_2$O$_4$
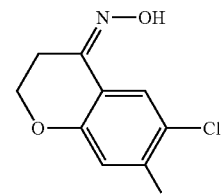
Co. No. 106; Ex. B. 18
TABLE F-1-continued
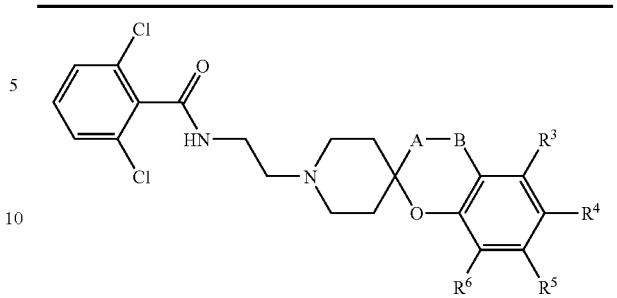
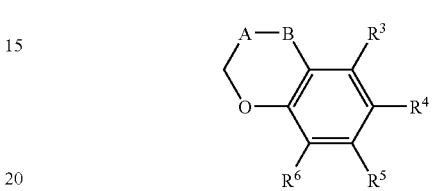
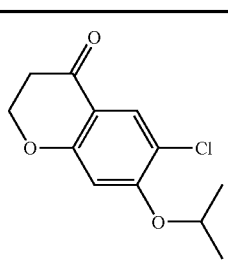
Co. No. 107; Ex. B. 11
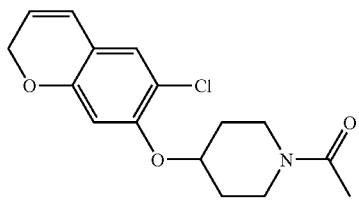
Co. No. 108; Ex. B. 19
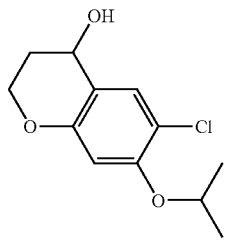
Co. No. 109; Ex. B. 4
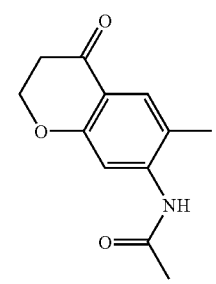
Co. No. 110; Ex. B. 11

TABLE F-1-continued
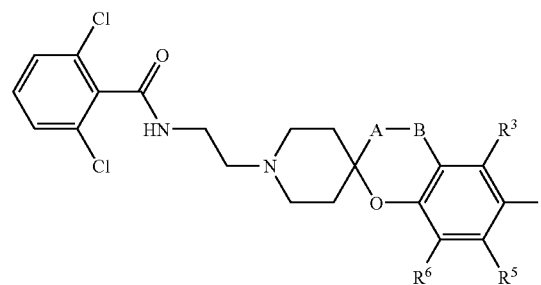
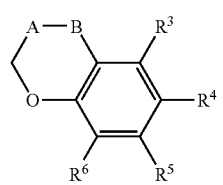
Co. No. 111; Ex. B. 4
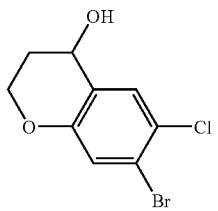
Co. No. 112; Ex. B. 19
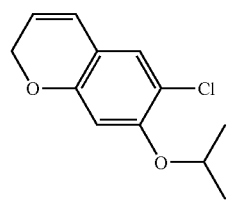
Co. No. 113; Ex. B. 12
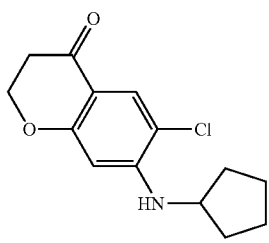
Co. No. 114; Ex. B. 4
TABLE F-1-continued
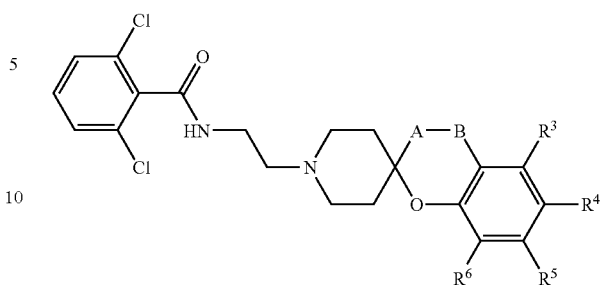
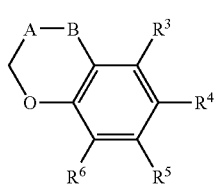
Co. No. 115; Ex. B. 4
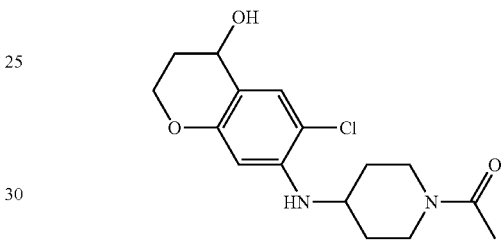
Co. No. 116; Ex. B. 19;
·C$_2$H$_2$O$_4$
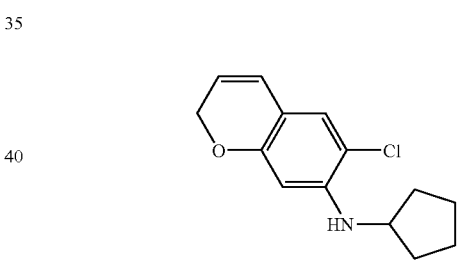
Co. No. 117; Ex. B. 20
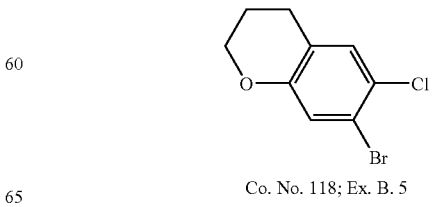
Co. No. 118; Ex. B. 5

TABLE F-1-continued
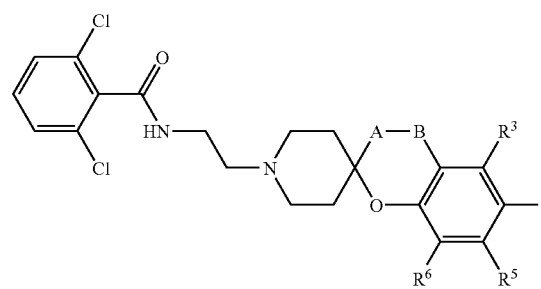
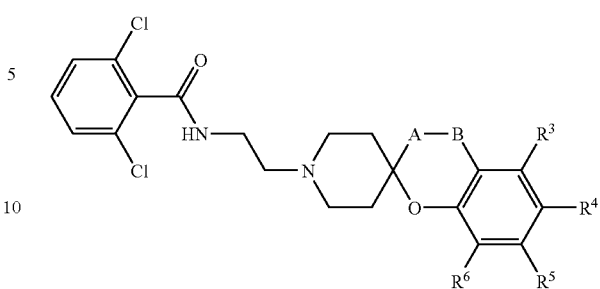
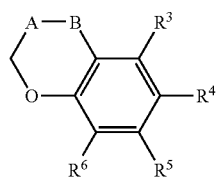
Co. No. 119; Ex. B. 11
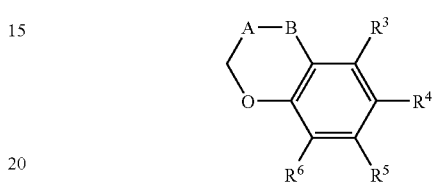
Co. No. 123; Ex. B. 15
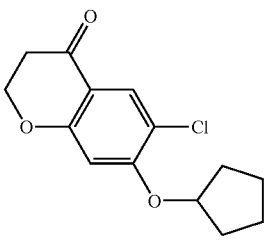
Co. No. 120; Ex. B. 7
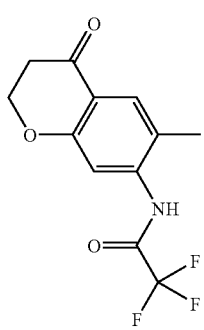
Co. No. 124; Ex. B. 20
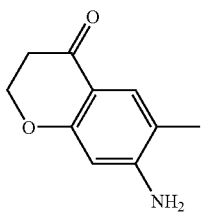
Co. No. 121; Ex. B. 21
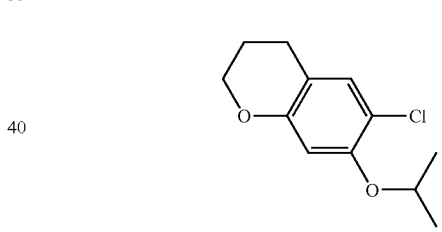
Co. No. 125; Ex. B. 4
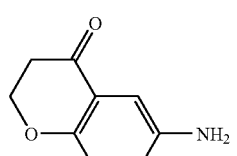
Co. No. 122; Ex. B. 19
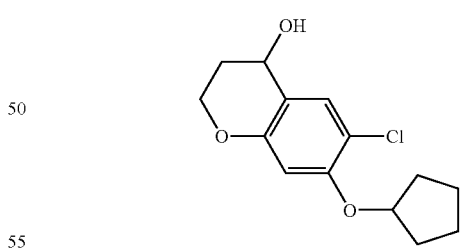
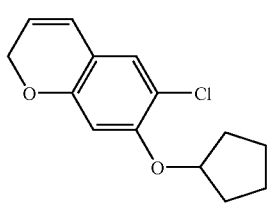
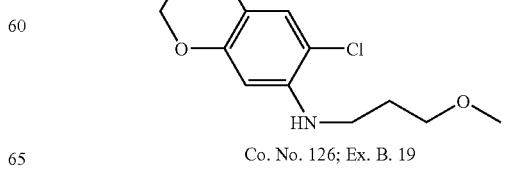
Co. No. 126; Ex. B. 19

TABLE F-1-continued
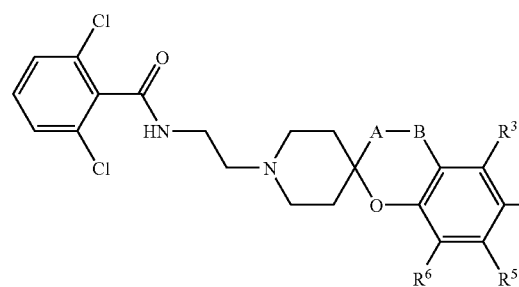
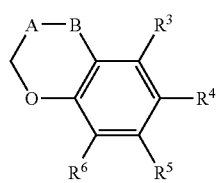
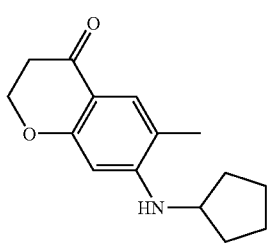
Co. No. 127; Ex. B. 22
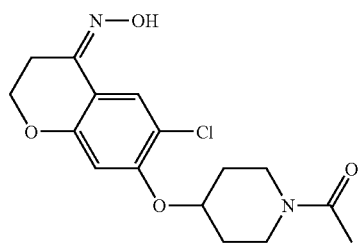
Co. No. 128; Ex. B. 18
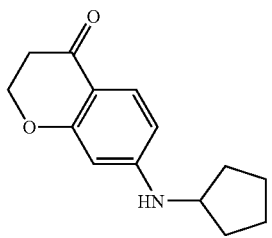
Co. No. 129; Ex. B. 22
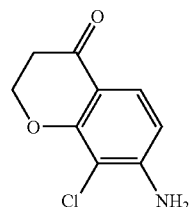
Co. No. 130; Ex. B. 23
TABLE F-1-continued
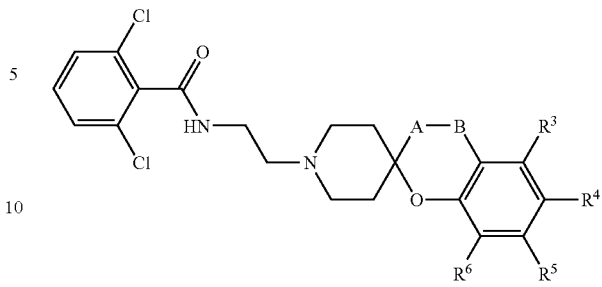
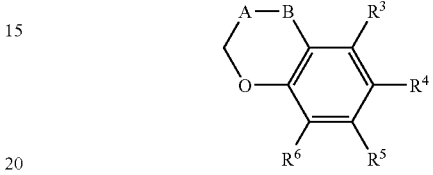
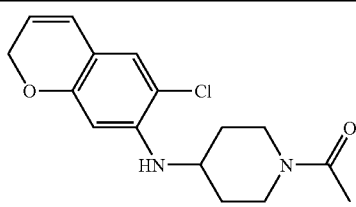
Co. No. 131; Ex. B. 19
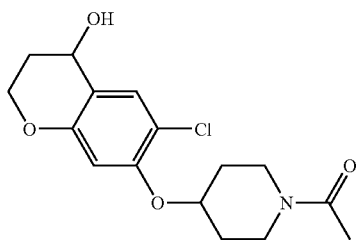
Co. No. 132; Ex. B. 4
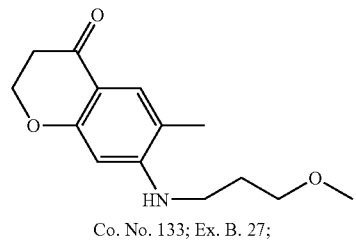
Co. No. 133; Ex. B. 27;
•C$_2$H$_2$O$_4$
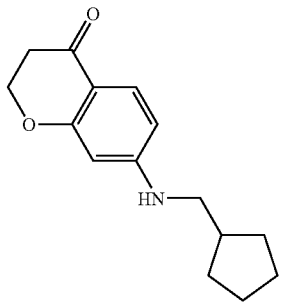
Co. No. 134; Ex. B. 16

TABLE F-1-continued
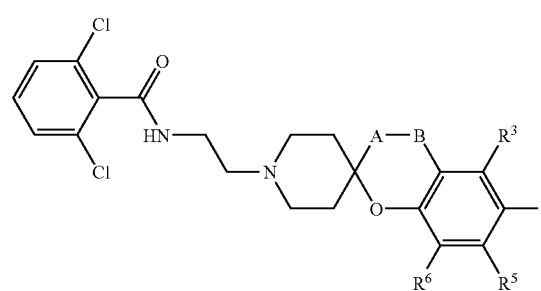
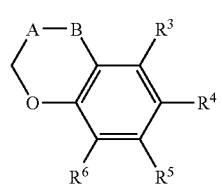
Co. No. 135; Ex. B. 17
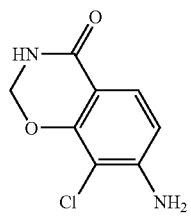
Co. No. 136; Ex. B. 20
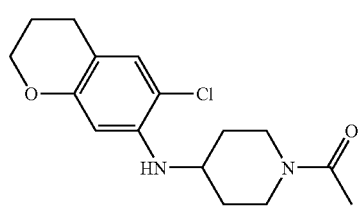
Co. No. 137; Ex. B. 11
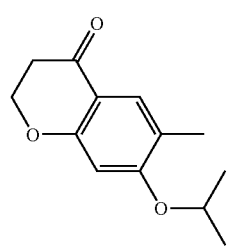
Co. No. 138; Ex. B. 11
TABLE F-1-continued
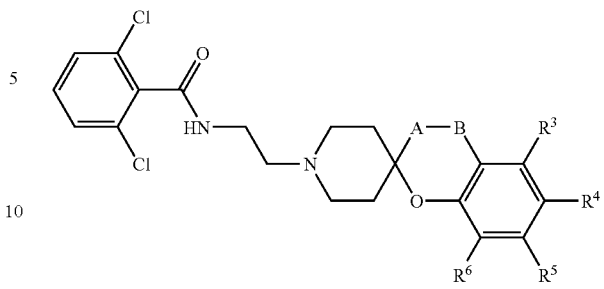
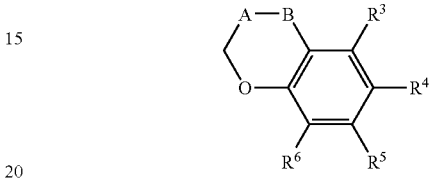
Co. No. 139; Ex. B. 11
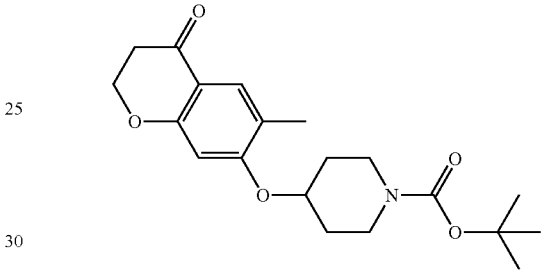
Co. No. 140; Ex. B. 20
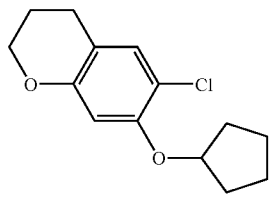
Co. No. 141; Ex. B. 24
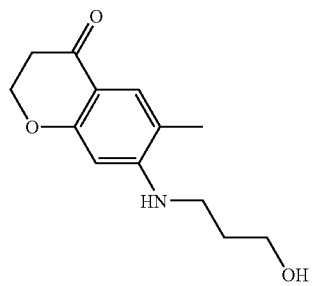
Co. No. 142; Ex. B. 7

TABLE F-1-continued
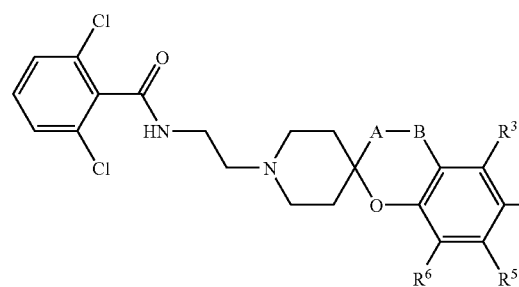
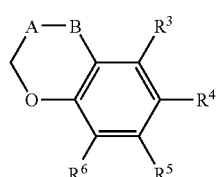
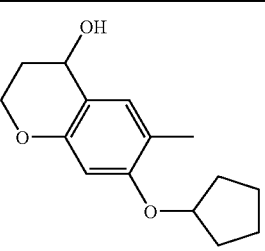
Co. No. 143; Ex. B. 4
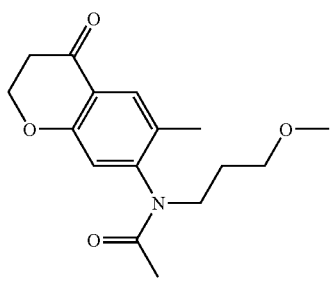
Co. No. 144; Ex. B. 24
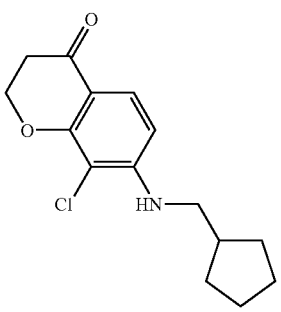
Co. No. 145; Ex. B. 23
TABLE F-1-continued
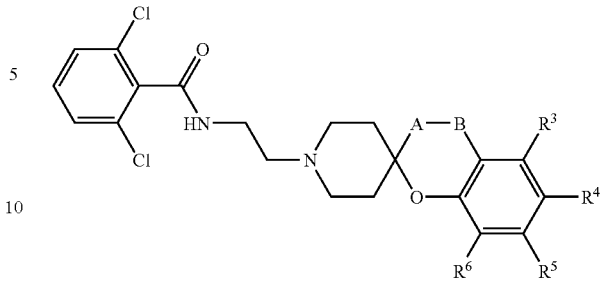
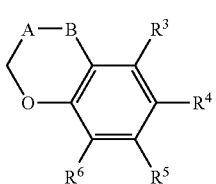
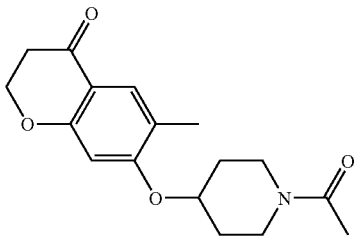
Co. No. 146; Ex. B. 15
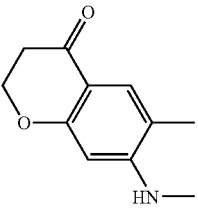
Co. No. 147; Ex. B. 24
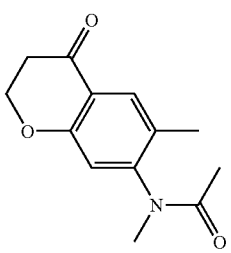
Co. No. 148; Ex. B. 24
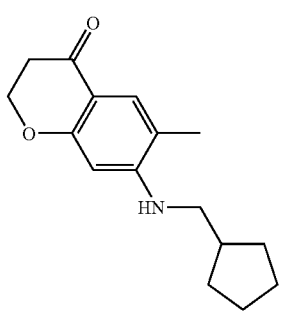
Co. No. 149; Ex. B. 24

TABLE F-1-continued
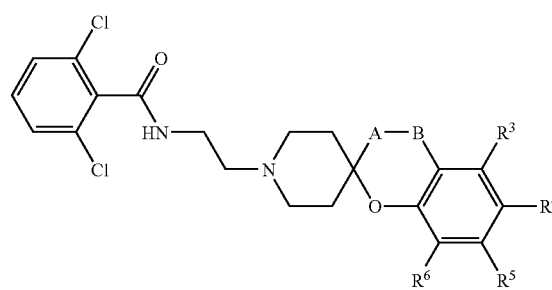
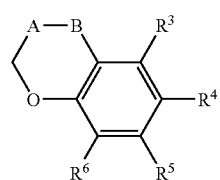
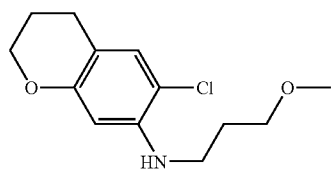
Co. No. 150; Ex. B. 20
TABLE F-2
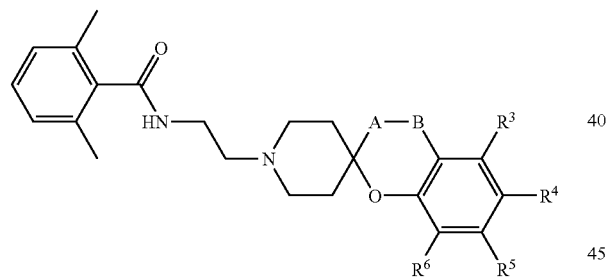
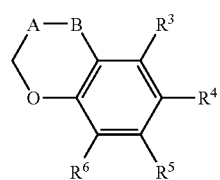
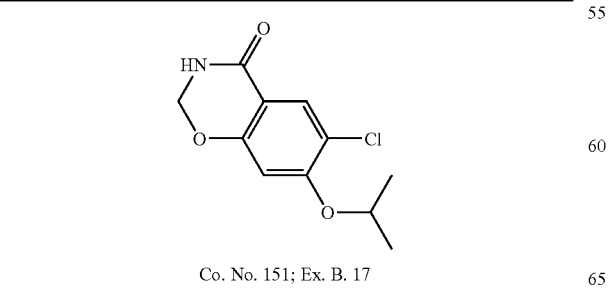
Co. No. 151; Ex. B. 17
TABLE F-2-continued
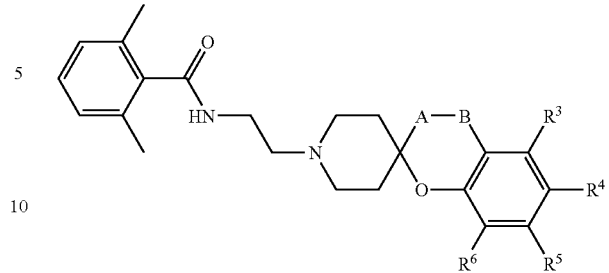
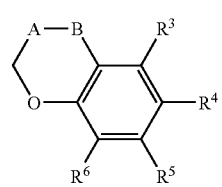
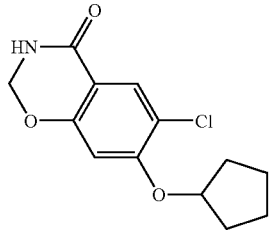
Co. No. 152; Ex. B. 17
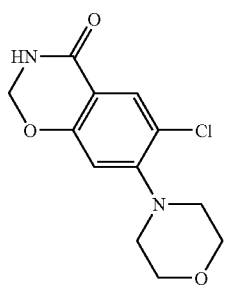
Co. No. 153; Ex. B. 17
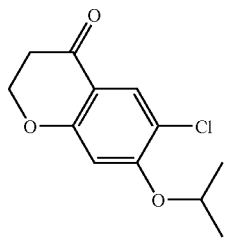
Co. No. 154; Ex. B. 11
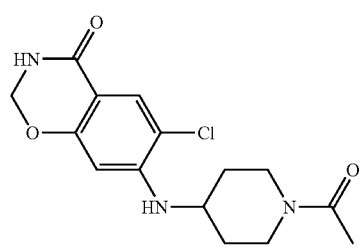
Co. No. 155; Ex. B. 17

TABLE F-2-continued
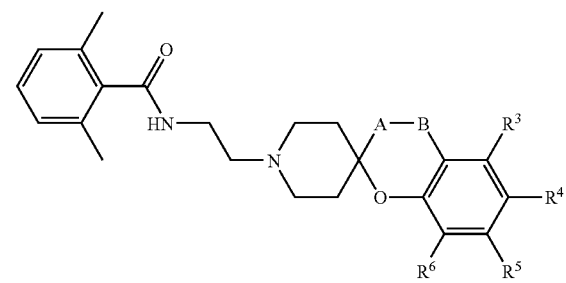
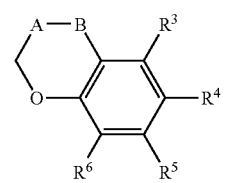
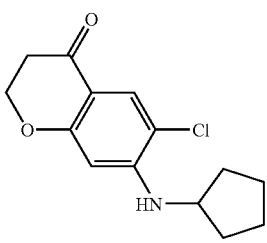
Co. No. 156; Ex. B. 12
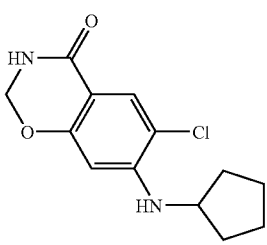
Co. No. 157; Ex. B. 17
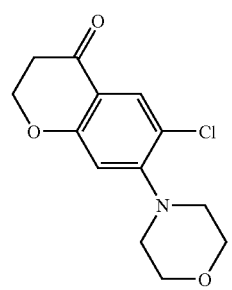
Co. No. 158; Ex. B. 12
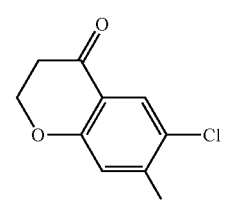
Co. No. 159; Ex. B. 11
TABLE F-2-continued
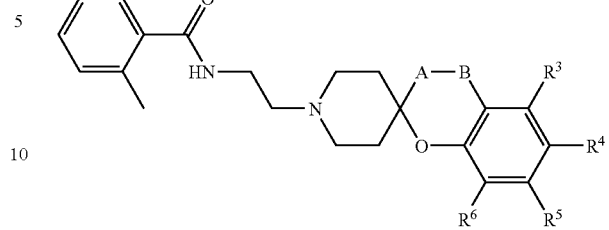
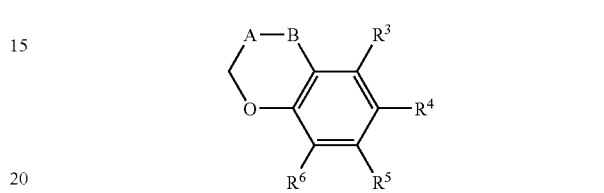
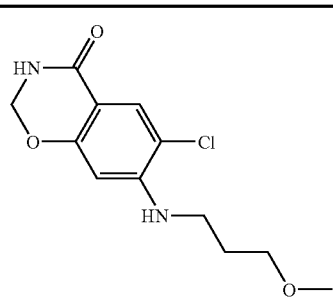
Co. No. 160; Ex. B. 17
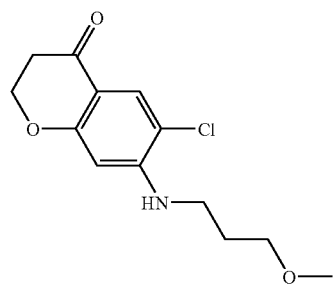
Co. No. 161; Ex. B. 12
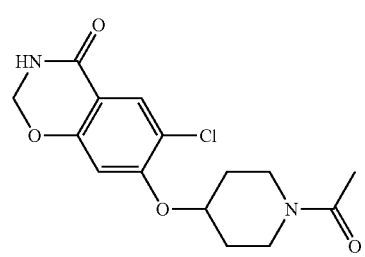
Co. No. 162; Ex. B. 15; •HCl TABLE F-2-continued
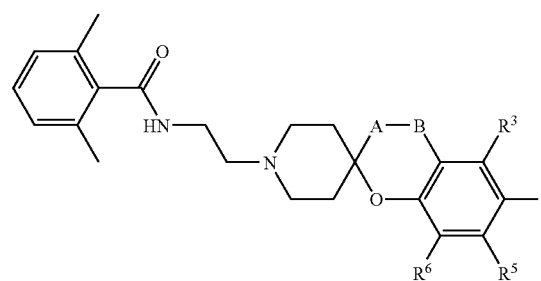
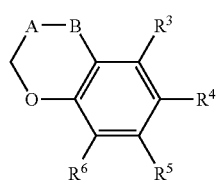
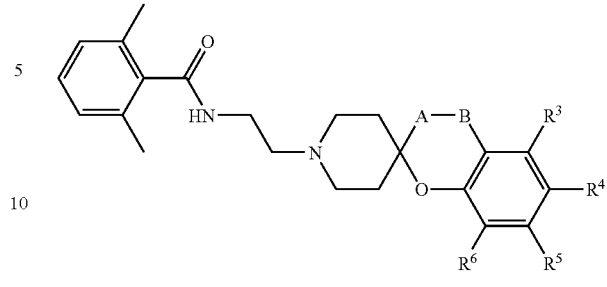
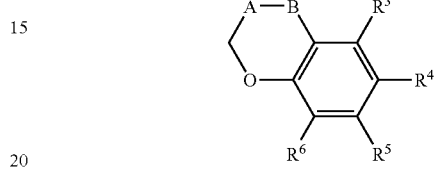
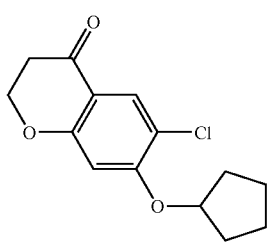
Co. No. 163; Ex. B. 11
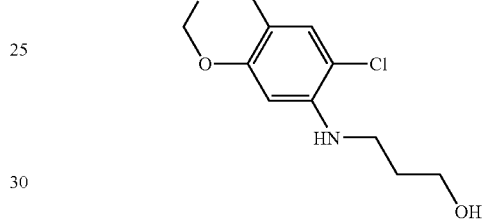
Co. No. 166; Ex. B. 14
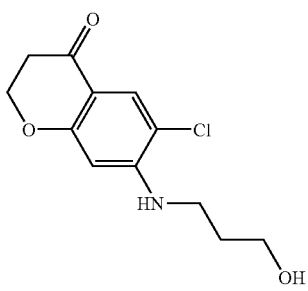
Co. No. 164; Ex. B. 14
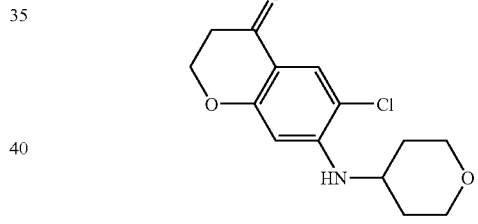
Co. No. 167; Ex. B. 12
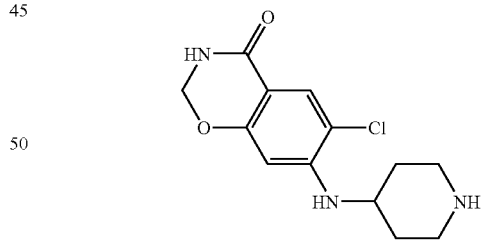
Co. No. 168; Ex. B. 7
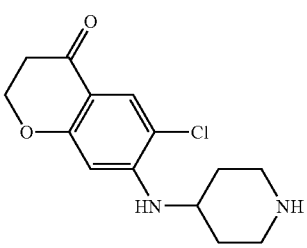
Co. No. 165; Ex. B. 7; ·HCl
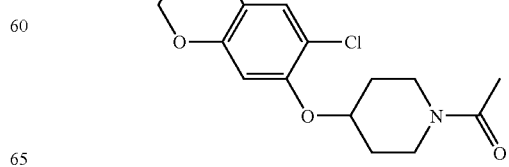
Co. No. 169; Ex. B. 15

TABLE F-2-continued
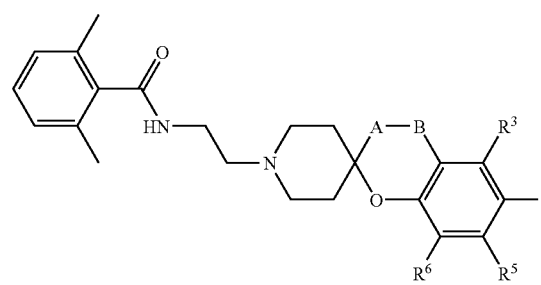
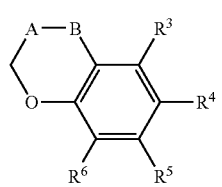
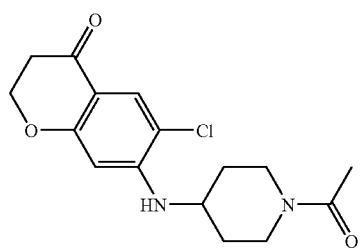
Co. No. 170; Ex. B. 15
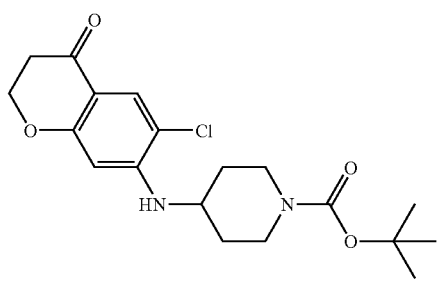
Co. No. 171; Ex. B. 12
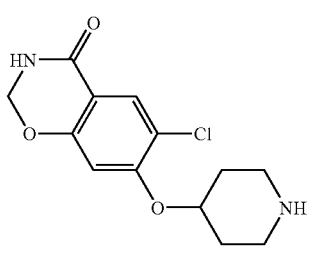
Co. No. 172; Ex. B. 7
TABLE F-2-continued
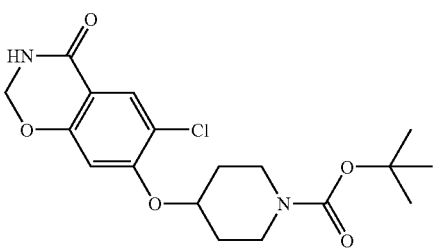
Co. No. 173; Ex. B. 17
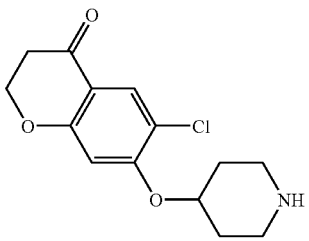
Co. No. 174; Ex. B. 7
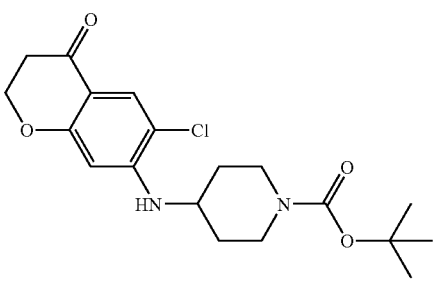
Co. No. 175; Ex. B. 11

TABLE F-2-continued
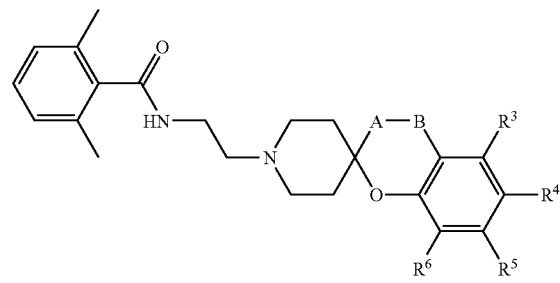
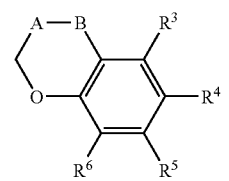
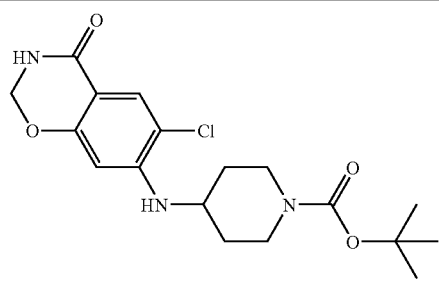
Co. No. 176; Ex. B. 17
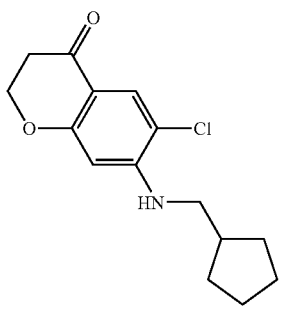
Co. No. 177; Ex. B. 12
TABLE F-2-continued
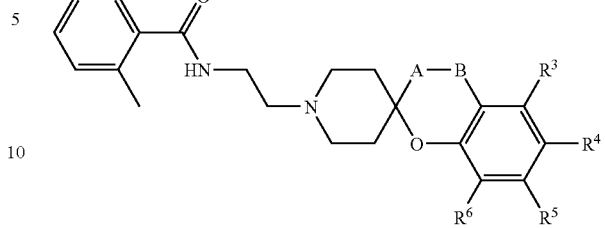
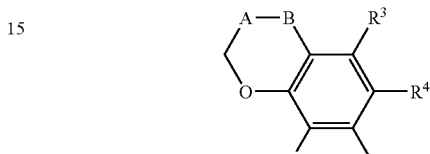
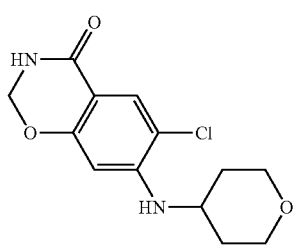
Co. No. 178; Ex. B. 17
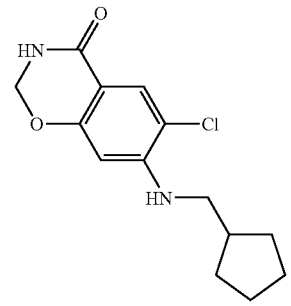
Co. No. 179; Ex. B. 17
TABLE F-3
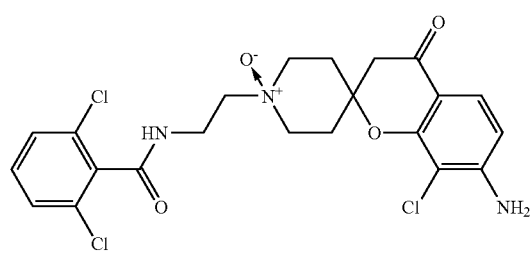
Co. No. 180; Ex. B. 25

TABLE F-3-continued
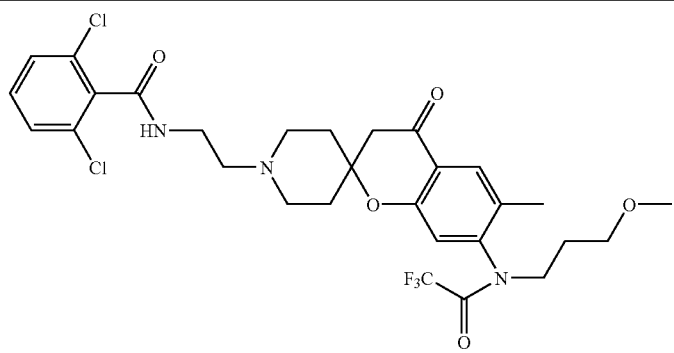
Co. No. 181; Ex. B. 26
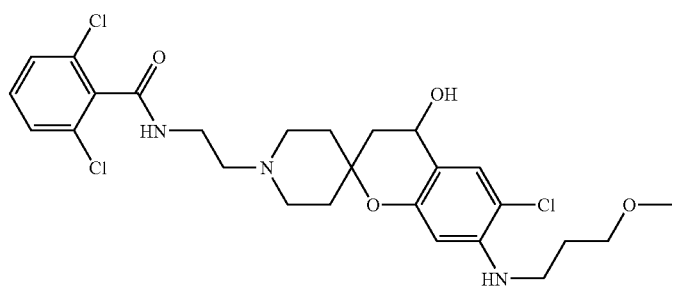
Co. No. 182; Ex. B. 4
TABLE F-4
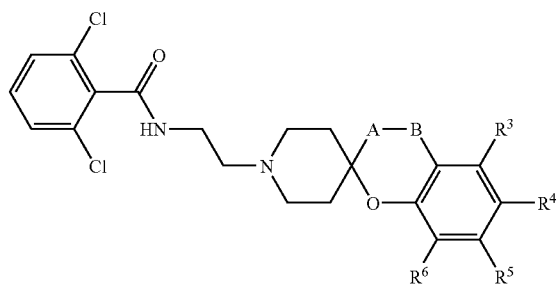
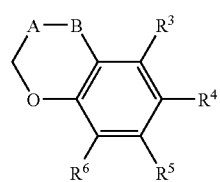
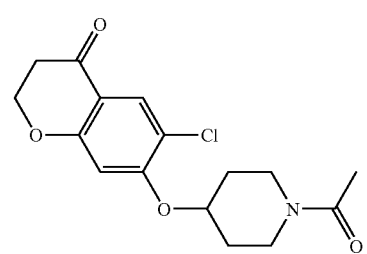
Co. No. 184; Ex. B. 15; •HCl
TABLE F-4-continued
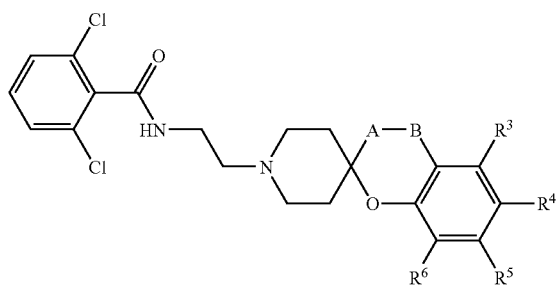
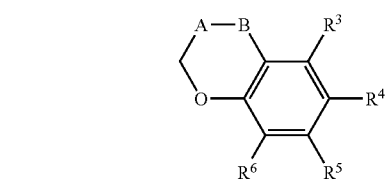
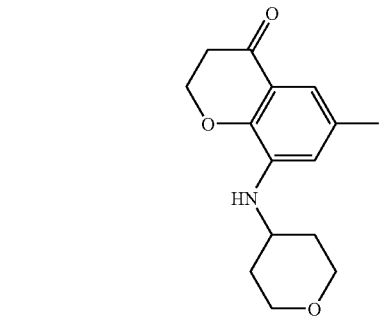
Co. No. 185; Ex. B. 24; •1.8 $C_2H_2O_4$ TABLE F-4-continued
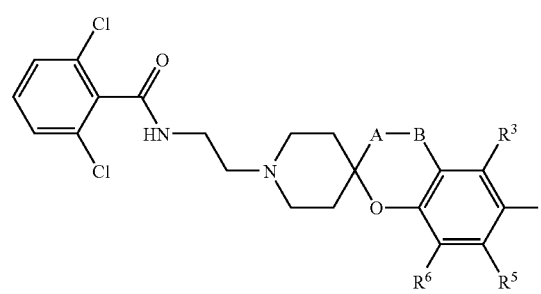
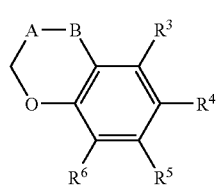
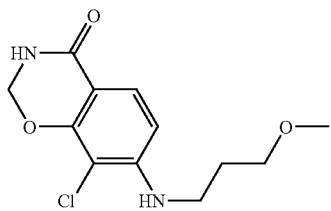
Co. No. 186; Ex. B. 24; •1.4 C₂H₂O₄
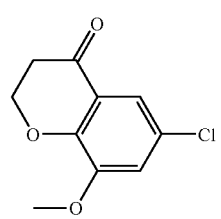
Co. No. 187; Ex. B. 24
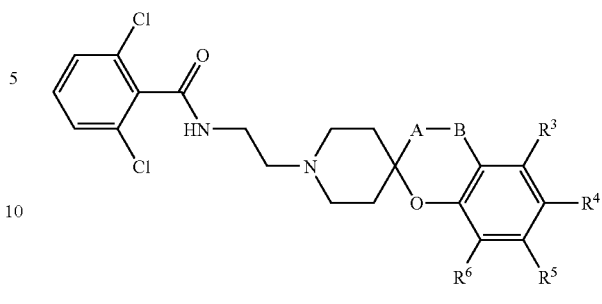
Co. No. 188; Ex. B. 4
TABLE F-4-continued
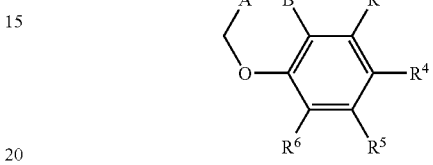
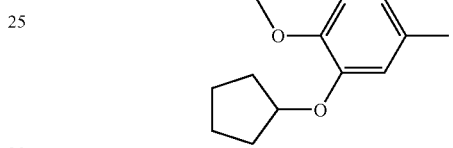
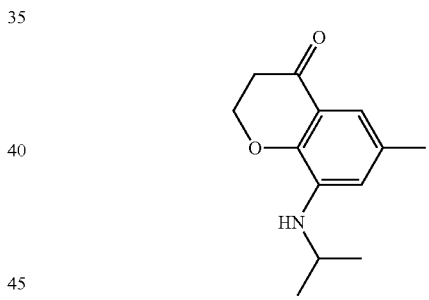
Co. No. 189; Ex. B. 29
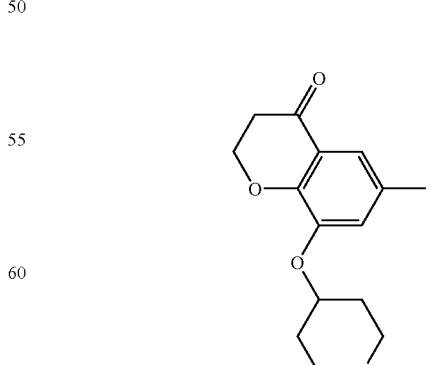
Co. No. 190; Ex. B. 24; •1.8 C₂H₂O₄
Co. No. 191; Ex. B. 7

TABLE F-4-continued
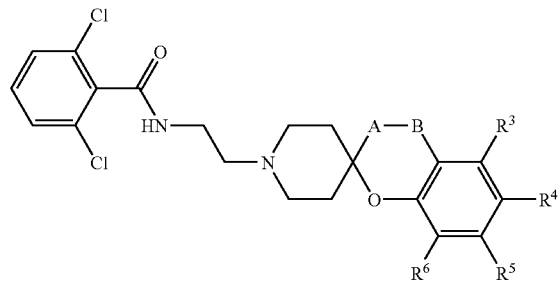
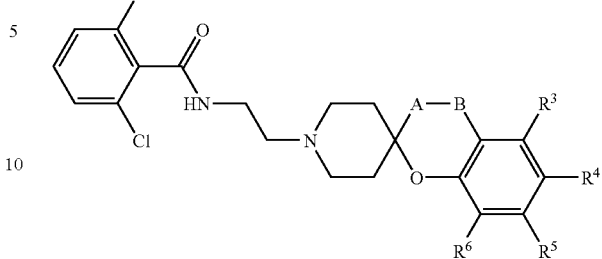
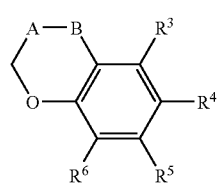
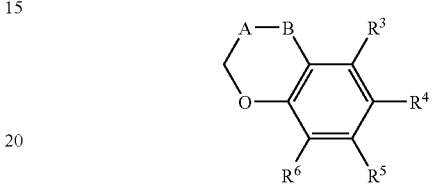
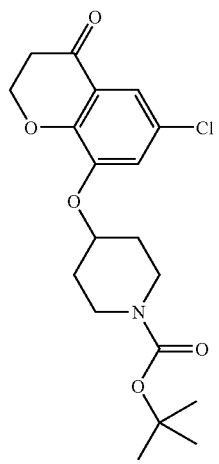
Co. No. 192; Ex. B. 6
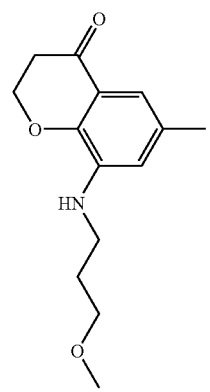
Co. No. 195; Ex. B. 24;
•C$_2$H$_2$O$_4$
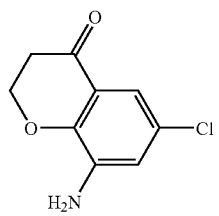
Co. No. 193; Ex. B. 24
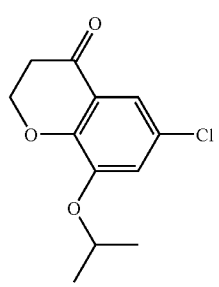
Co. No. 194; Ex. B. 29
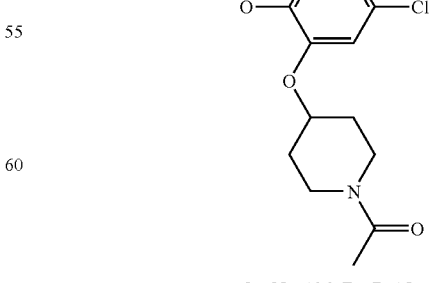
Co. No. 196; Ex. B. 15

TABLE F-4-continued
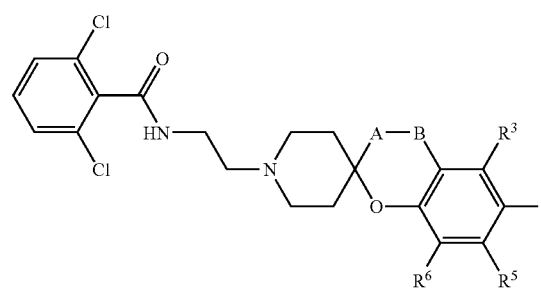
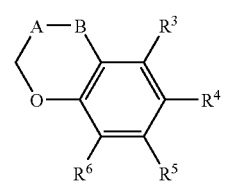
Co. No. 197; Ex. B. 24
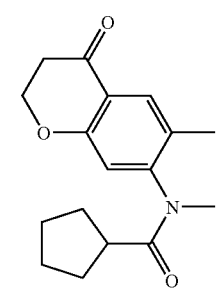
Co. No. 198; Ex. B. 3
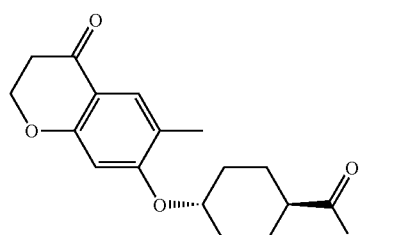
Co. No. 199; Ex. B. 31;
•C₂H₂O₄
TABLE F-4-continued
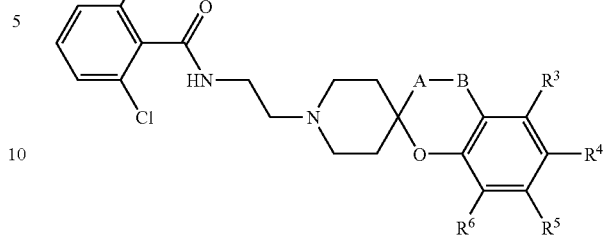
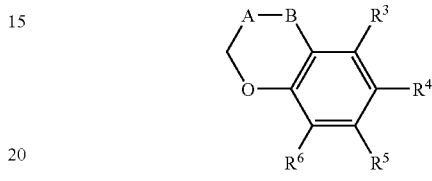
Co. No. 200; Ex. B. 24
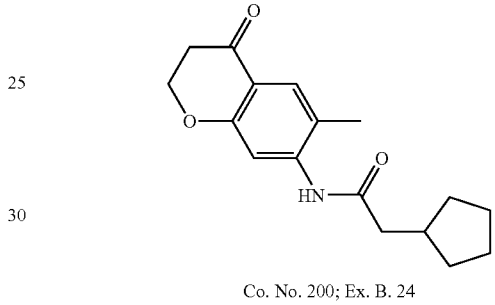
Co. No. 201; Ex. B. 32
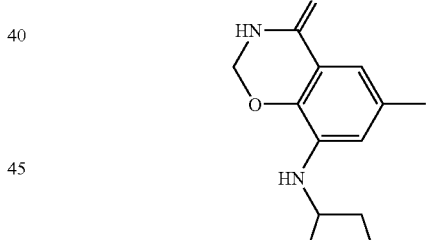
Co. No. 202; Ex. B. 30

TABLE F-4-continued
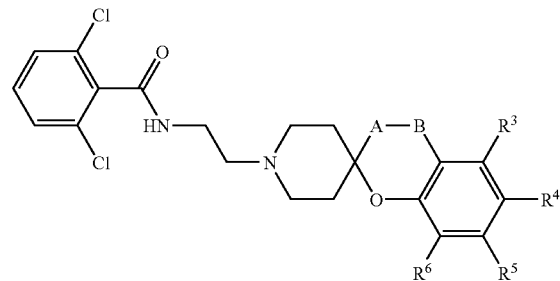
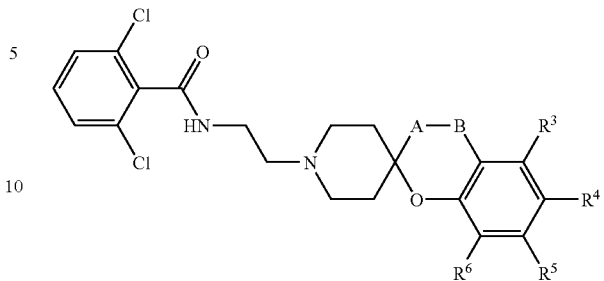
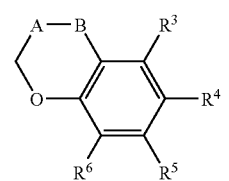
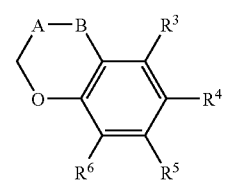
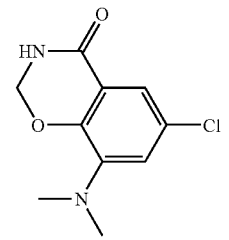
Co. No. 203; Ex. B. 30
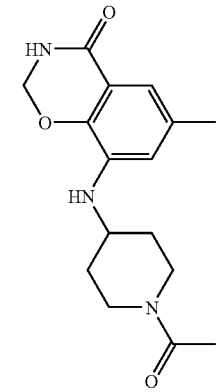
Co. No. 206; Ex. B. 32
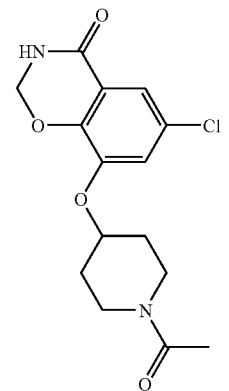
Co. No. 204; Ex. B. 15
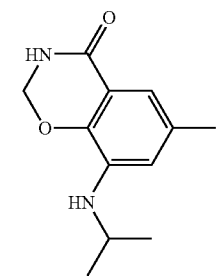
Co. No. 207; Ex. B. 32
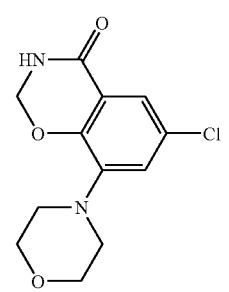
Co. No. 205; Ex. B. 33
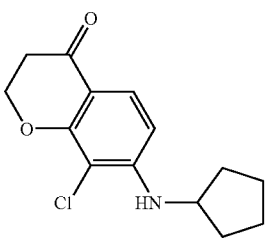
Co. No. 208; Ex. B. 28

TABLE F-4-continued
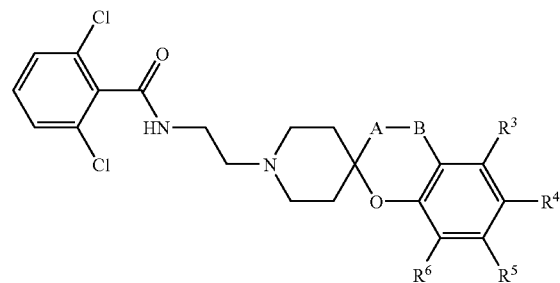
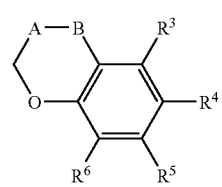
Co. No. 209; Ex. B. 25; •1.8 C₂H₂O₄
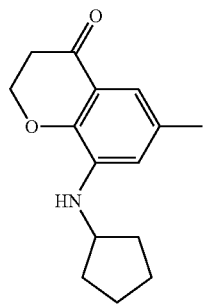
Co. No. 210; Ex. B. 24
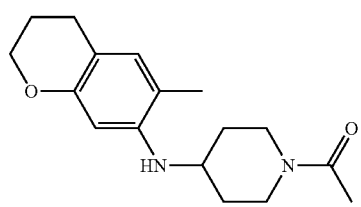
Co. No. 211; Ex. B. 24
TABLE F-4-continued
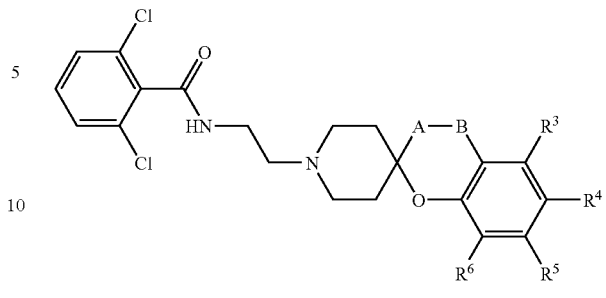
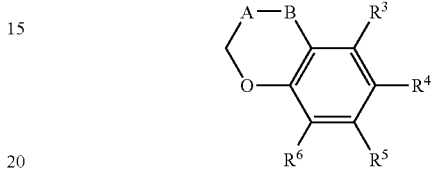
Co. No. 212; Ex. B. 24
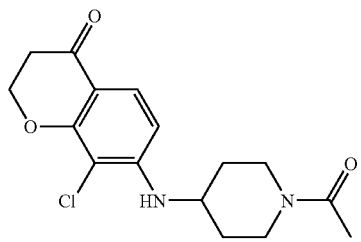
Co. No. 213; Ex. B. 29
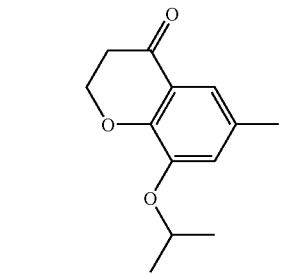
Co. No. 214; Ex. B. 24
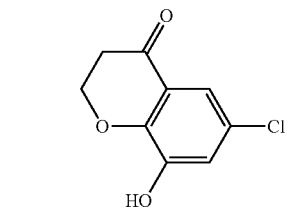
Co. No. 215; Ex. B. 11

TABLE F-4-continued
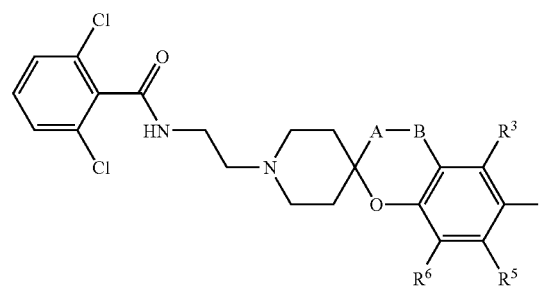
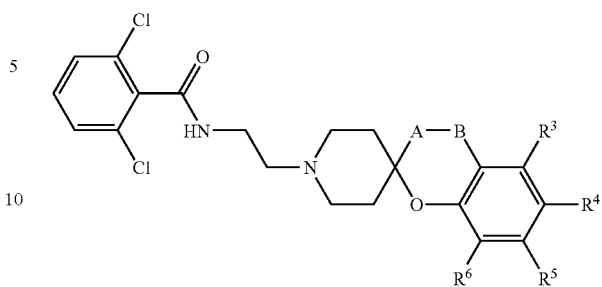
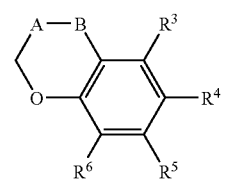
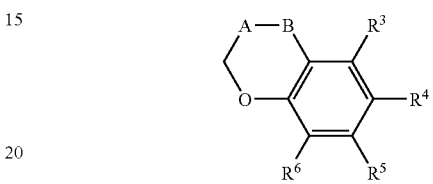
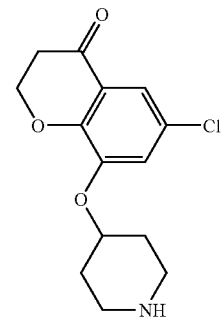
Co. No. 216; Ex. B. 7
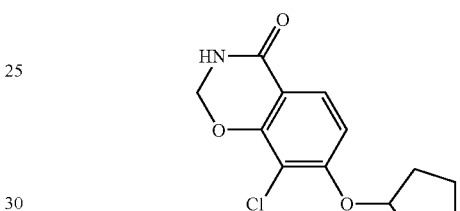
Co. No. 219; Ex. B. 3
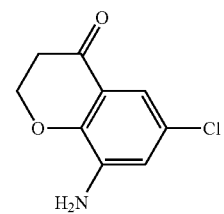
Co. No. 217; Ex. B. 24;
•HBr
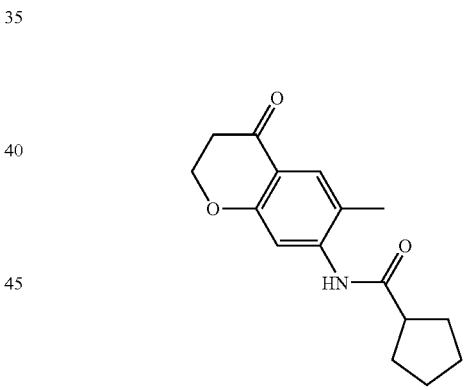
Co. No. 220; Ex. B. 24
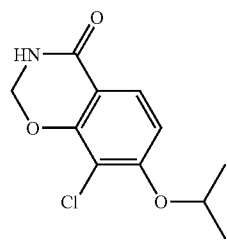
Co. No. 218; Ex. B. 3
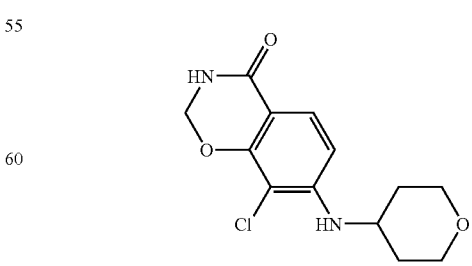
Co. No. 221; Ex. B. 1

TABLE F-4-continued
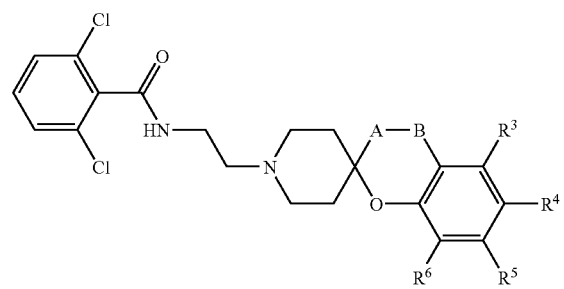
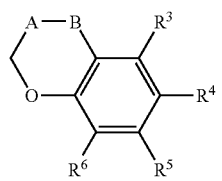
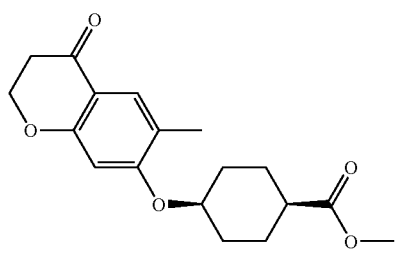
Co. No. 222; Ex. B. 31;
•C₂H₂O₄
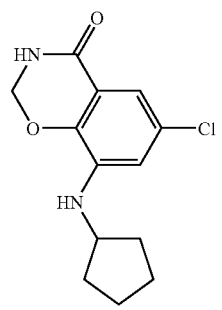
Co. No. 223; Ex. B. 32
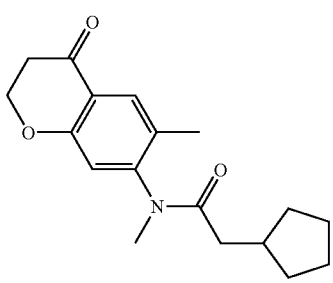
Co. No. 224; Ex. B. 24
TABLE F-4-continued
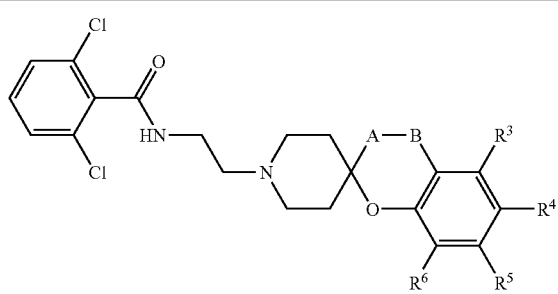
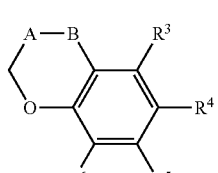
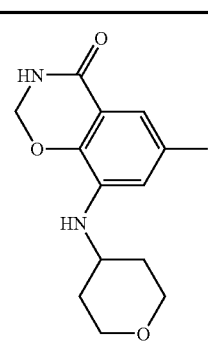
Co. No. 225; Ex. B. 32
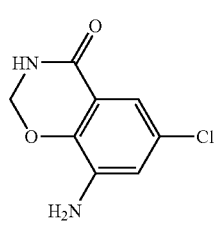
Co. No. 226; Ex. B. 3
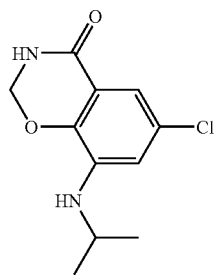
Co. No. 227; Ex. B. 30

TABLE F-4-continued
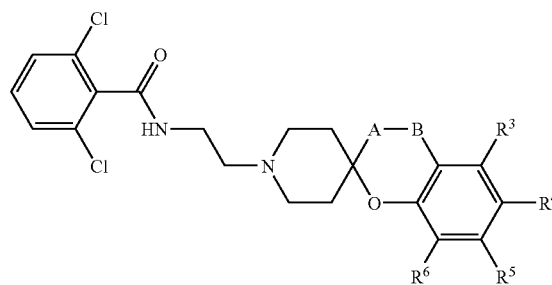
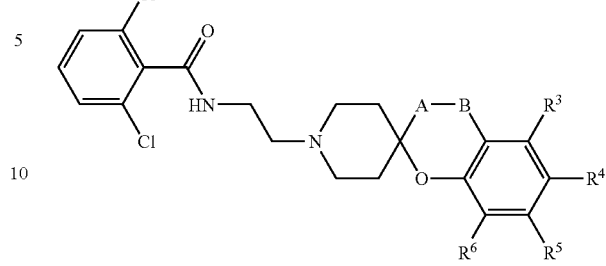
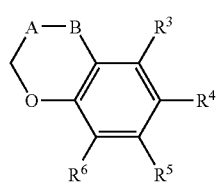
Co. No. 228; Ex. B. 29
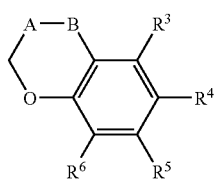
Co. No. 231; Ex. B. 24; •1.1 C$_2$H$_2$O$_4$
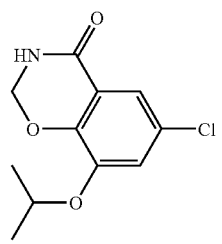
Co. No. 229; Ex. B. 32
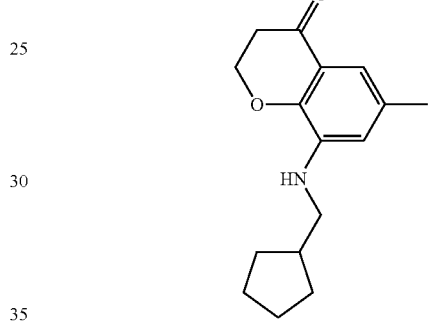
Co. No. 232; Ex. B. 15;
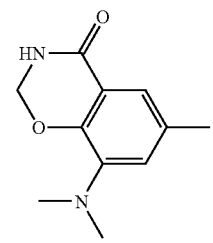
Co. No. 230; Ex. B. 32
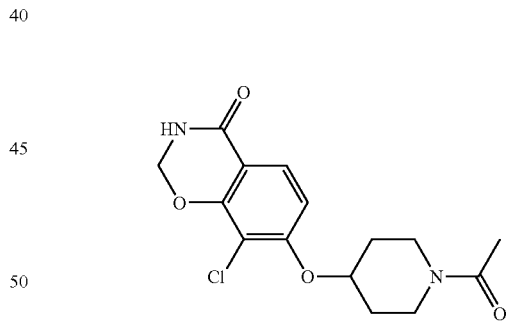
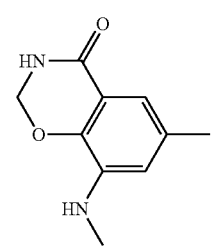
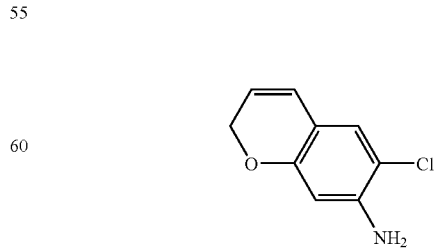
Co. No. 233; Ex. B. 19

TABLE F-4-continued
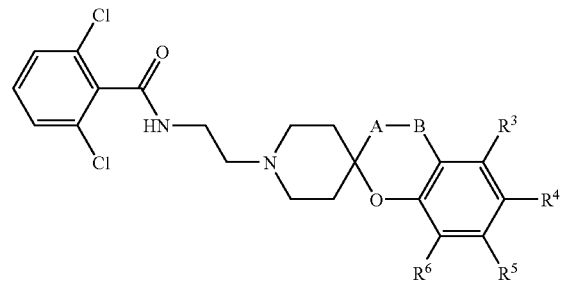
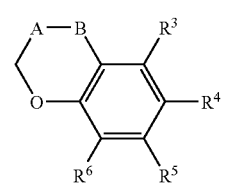
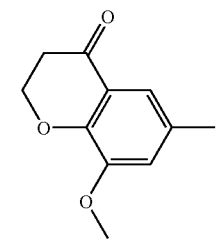
Co. No. 234; Ex. B. 11
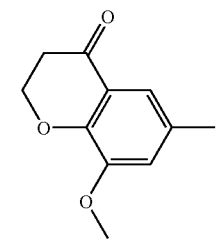
Co. No. 235; Ex. B. 11
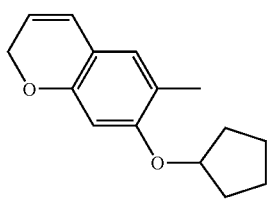
Co. No. 236; Ex. B. 19
TABLE F-4-continued
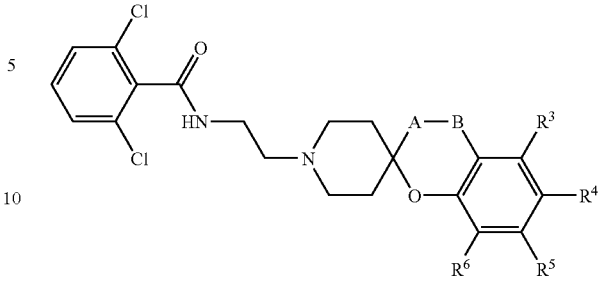
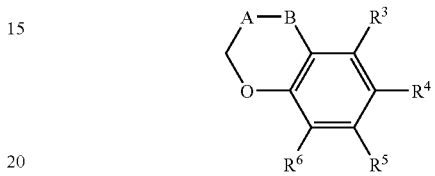
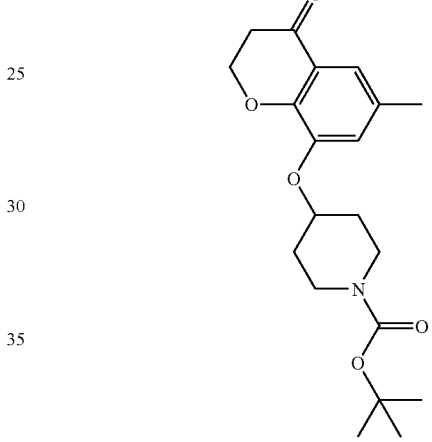
Co. No. 237; Ex. B. 6
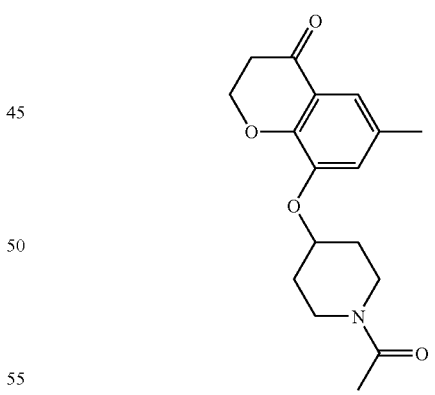
Co. No. 238; Ex. B. 15
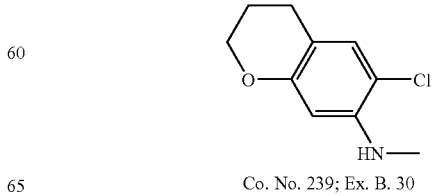
Co. No. 239; Ex. B. 30

TABLE F-4-continued
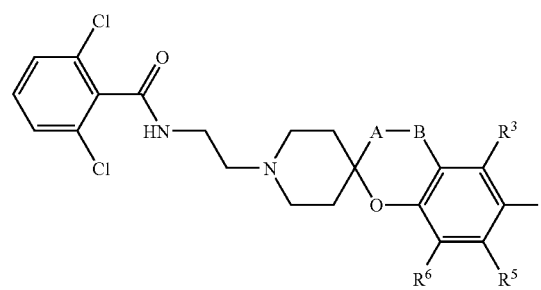
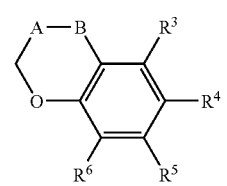
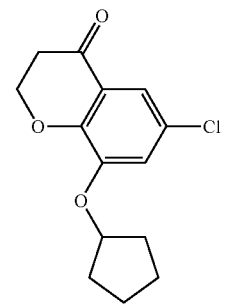
Co. No. 240; Ex. B. 29
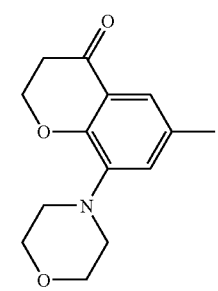
Co. No. 241; Ex. B. 24;
·C₂H₂O₄
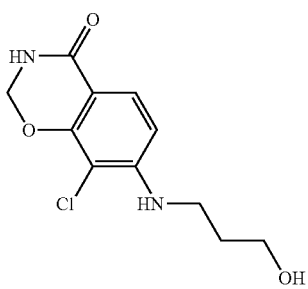
Co. No. 242; Ex. B. 14
TABLE F-4-continued
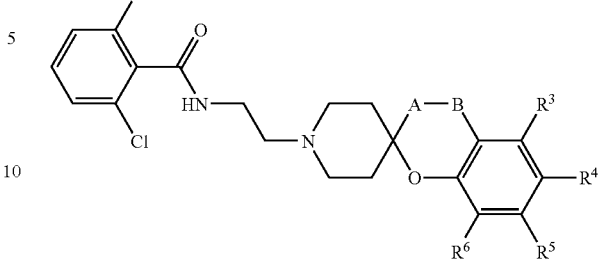
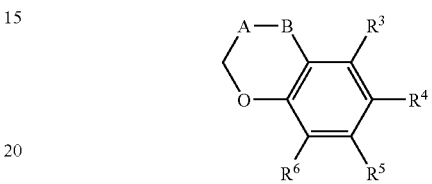
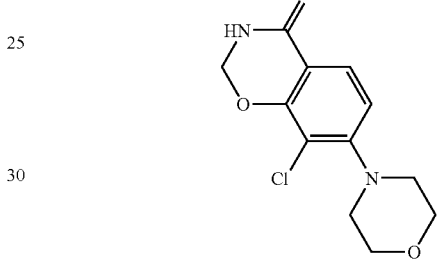
Co. No. 243; Ex. B. 1
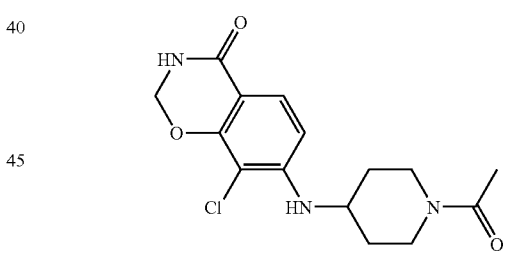
Co. No. 244; Ex. B. 1
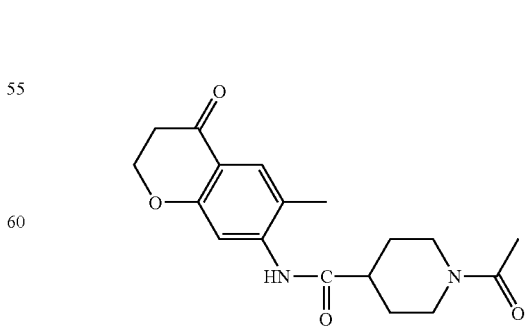
Co. No. 245; Ex. B. 24

TABLE F-4-continued
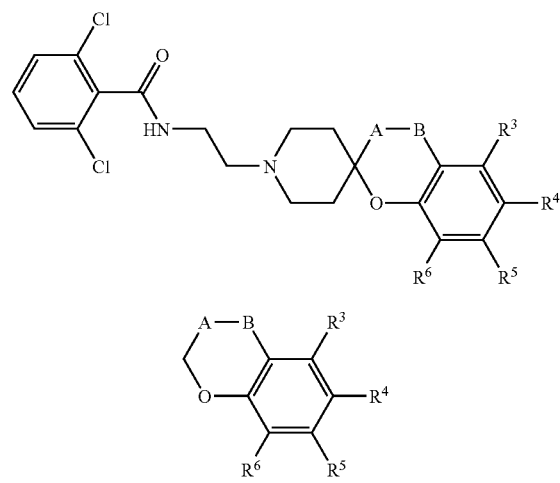
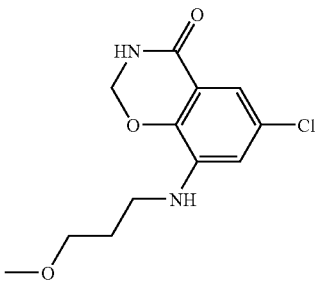
Co. No. 246; Ex. B. 32
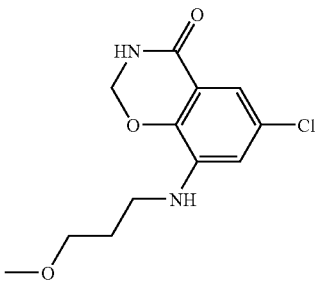
Co. No. 247; Ex. B. 32
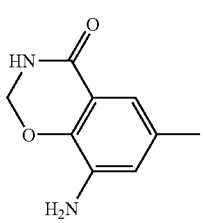
Co. No. 248; Ex. B. 3
TABLE F-4-continued
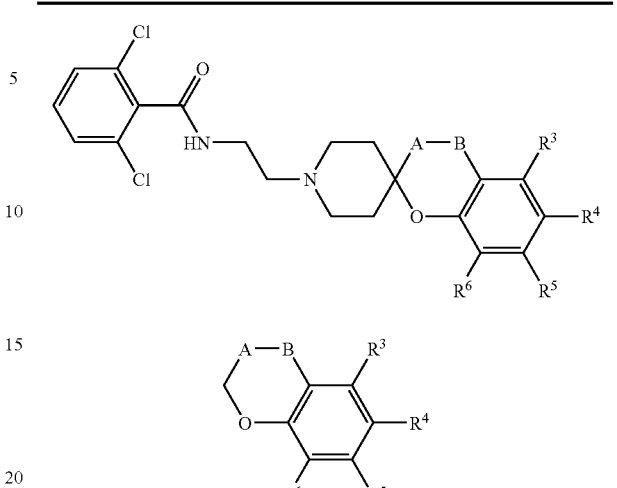
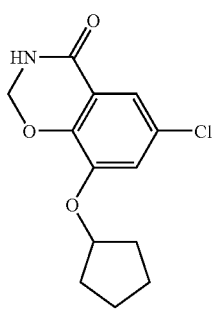
Co. No. 249; Ex. B. 30
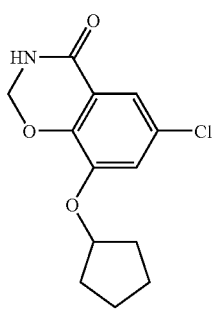
Co. No. 250; Ex. B. 29
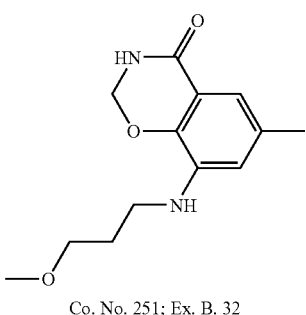
Co. No. 251; Ex. B. 32

TABLE F-4-continued
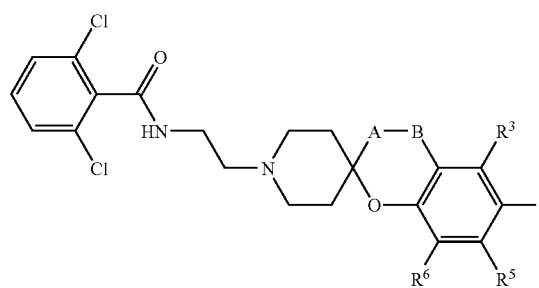
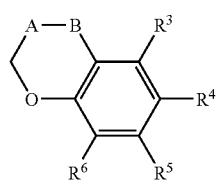
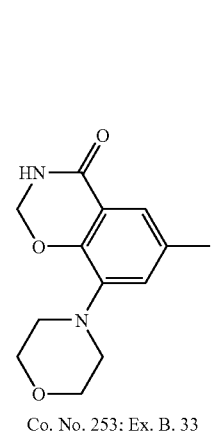
Co. No. 252; Ex. B. 14
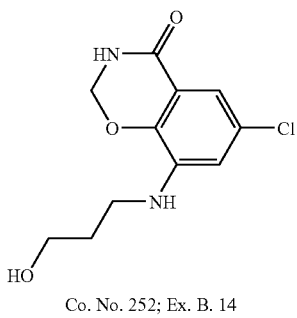
Co. No. 253; Ex. B. 33
* $C_2H_2O_4$ stands for the ethanedioate salt
TABLE F-5
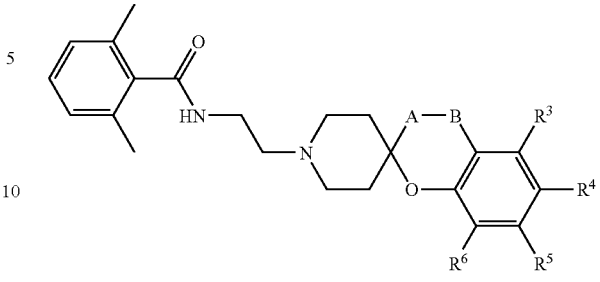
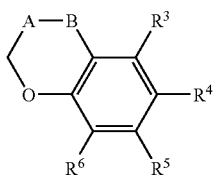
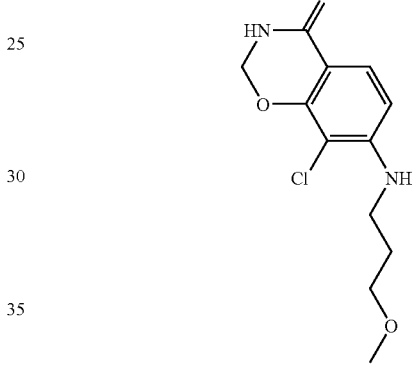
Co. No. 254; Ex. B. 1
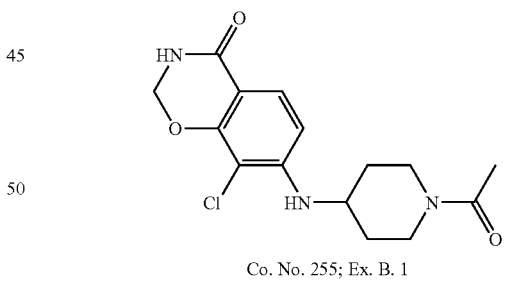
Co. No. 255; Ex. B. 1
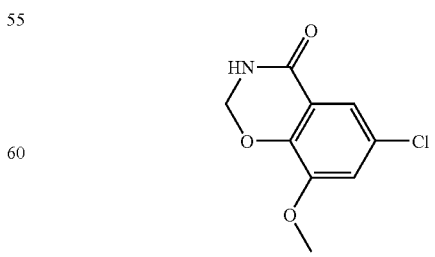
Co. No. 256; Ex. B. 31

TABLE F-5-continued
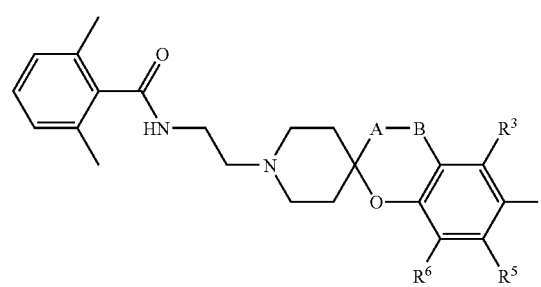
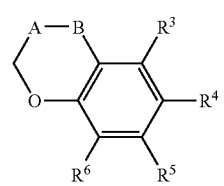
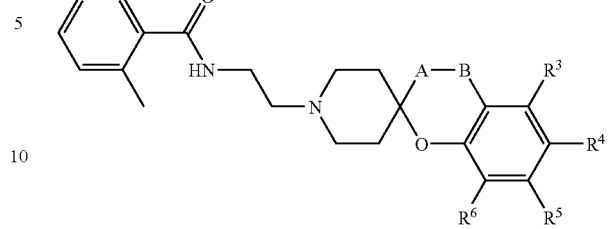
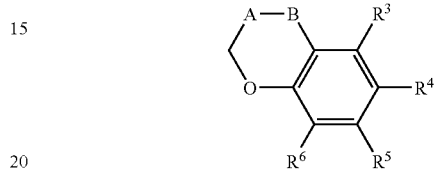
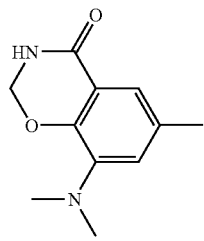
Co. No. 257; Ex. B. 32
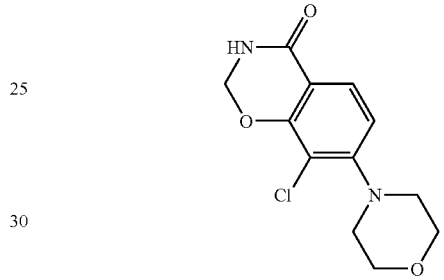
Co. No. 260; Ex. B. 1
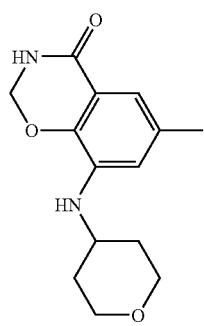
Co. No. 258; Ex. B. 32
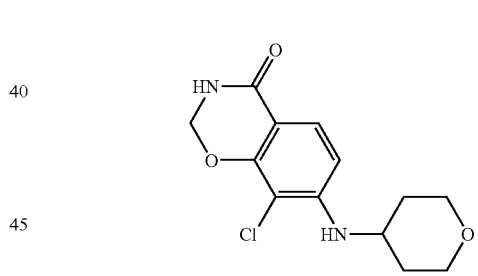
Co. No. 261; Ex. B. 1
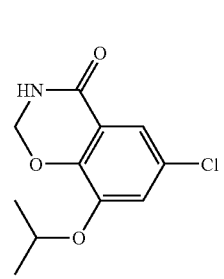
Co. No. 259; Ex. B. 29
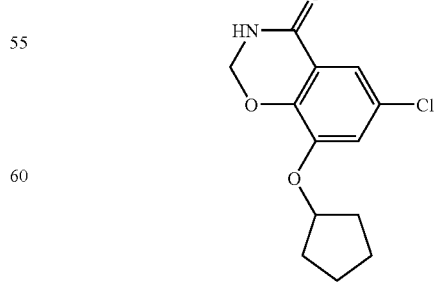
Co. No. 262; Ex. B. 29

TABLE F-5-continued
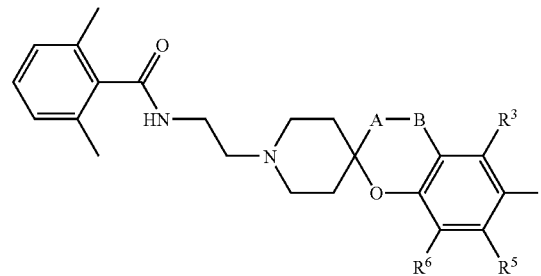
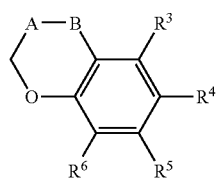
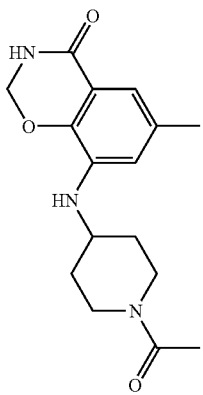
Co. No. 263; Ex. B. 32
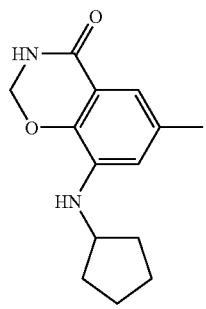
Co. No. 264; Ex. B. 32
TABLE F-5-continued
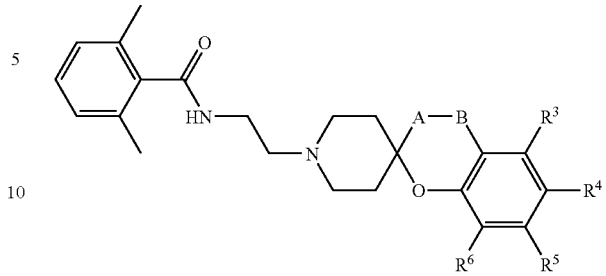
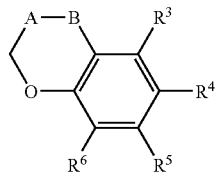
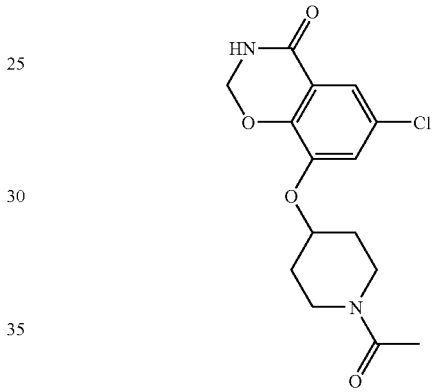
Co. No. 265; Ex. B. 15
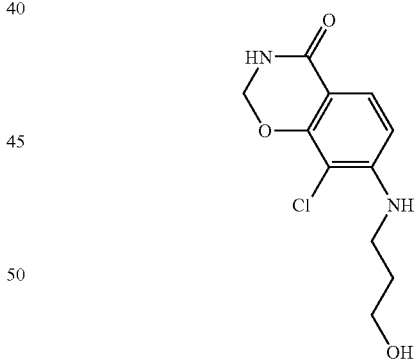
Co. No. 266; Ex. B. 14
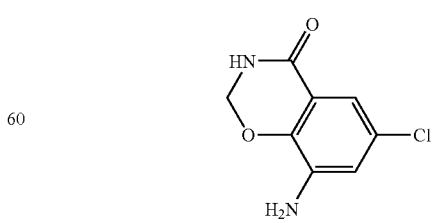
Co. No. 267; Ex. B. 31

TABLE F-5-continued

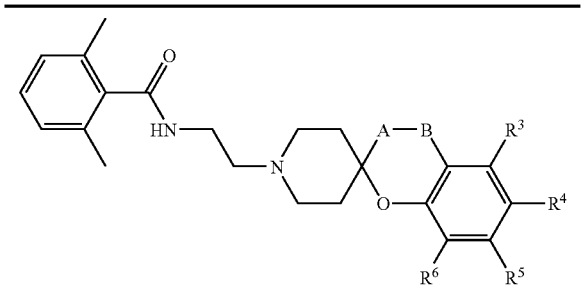

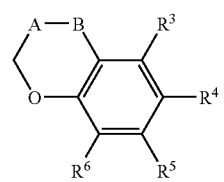

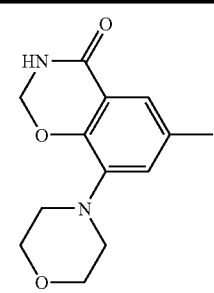
Co. No. 268; Ex. B. 33

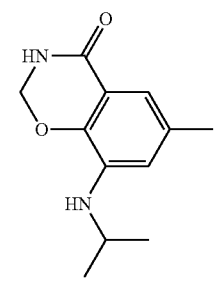
Co. No. 269; Ex. B. 32

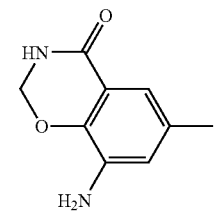
Co. No. 270; Ex. B. 31

C. Analytical Part
C.1 Melting Points

For a number of compounds, melting points (m.p.) were determined Values are either peak values or melt ranges, and were obtained with experimental uncertainties that are commonly associated with this analytical method. The melting points that are reported in Table F-6 were obtained with a DSC823e (Mettler-Toledo; temperature gradient of 30° C./minute, maximum temperature 400° C.), a Diamond DSC (PerkinElmer; temperature gradient of 10° C./minute, maximum temperature 300° C.), a WRS-2A melting poing apparatus (Shanghai Precision and Scientific Instrument Co. Ltd.; linear heating up rate 0.2-5.0° C./min, maximum temperature 300° C.) or a Kofler hot bench (consisting of a heated plate with linear temperature gradient, a sliding pointer and a temperature scale in degrees Celsius).

TABLE F-6 melting points (m.p. is defined as melting point).

| Co. No. | mp. |
|---|---|
| 1 | 245.39° C. |
| 7 | 257.70° C. |
| 8 | 221.35° C. |
| 10 | 191.14° C. |
| 11 | 230.30° C. |
| 12 | 146.1-149.8° C. (*) |
| 18 | 198.39° C. |
| 19 | 210.42° C. |
| 20 | 194.91° C.-199.60° C. |
| 21 | 195.39° C. |
| 22 | 172.85° C. |
| 25 | 250.55° C.-255.51° C. |
| 27 | 146.87° C. |
| 28 | 205.39° C.-207.69° C. |
| 30 | 154.80° C. |
| 34 | 210.81° C.-214.87° C. |
| 35 | 177.12° C.-183.06° C. |
| 37 | 239.40° C.-240.55° C. |
| 38 | 243.75° C.-249.58° C. |
| 40 | 193.56° C. |
| 45 | 197.7-198.6° C. |
| 46 | 169.4-170.0° C. |
| 47 | 199.8-203.1° C. |
| 48 | 169.05-172.03° C. |
| 49 | 180.74-182.95° C. |
| 50 | 162.89-166.29° C. (*) |
| 51 | 159.5-163.25° C. (*) |
| 53 | 187.20-189.17° C. (*) |
| 54 | 192.6-197.9° C. (*) |
| 60 | 115.1-126.5° C. (*) |
| 62 | 238.72-260.41° C. (*) |
| 63 | 175.14-176.95° C. (*) |
| 64 | 165.52-167.42° C. (*) |
| 65 | 162.13° C. |
| 66 | 273.14° C. |
| 67 | 264.30° C. |
| 68 | 285.19° C. |
| 69 | 208.05° C. |
| 70 | 279.94° C. |
| 71 | 285.34° C. |
| 72 | 260.65° C. |
| 73 | >260° C. |
| 75 | 260.52° C. |
| 76 | 163.69° C. |
| 77 | 263.77° C. |
| 78 | 259.92° C. |
| 79 | 269.12° C. |
| 80 | 274.79° C. |
| 81 | 179.99° C. |
| 83 | 158.54° C. |
| 85 | 186.84-191.73° C. (**) |
| 86 | 176.18-180.97° C. (**) |
| 89 | 176.37° C. |
| 90 | 150° C. decompose (*) |
| 91 | 187.06° C. |
| 92 | 143.0-145.8° C. (*) |
| 93 | 209.19° C. |
| 94 | 200.6-209.9° C. (*) |
| 95 | 207.68-215.42° C. (**) |
| 96 | 238.27° C. |
| 97 | 153.71-156.93° C. (**) |
| 98 | 235.72-239.12° C. (**) |
| 99 | 134.0-146.5° C. (*) |
| 101 | 172.22° C. |
| 102 | 167.05-171.80° C. (**) |
| 109 | 97.24° C. |
| 110 | 128.37° C. |
| 111 | 195.27° C. |

TABLE F-6-continued melting points (m.p. is defined as melting point).

| Co. No. | mp. |
|---|---|
| 112 | 139.39° C. |
| 114 | 173.23° C. |
| 120 | 262.67° C. |
| 126 | 169.47° C. |
| 130 | 236.63° C. |
| 133 | 157.06° C. |
| 135 | 234.04° C. |
| 137 | 173.26° C. |
| 138 | 136.85° C. |
| 144 | 152.83° C. |
| 145 | 172.83° C. |
| 148 | 153.73° C. |
| 150 | 151.90° C. |
| 151 | 201.61-204.20° C. (**) |
| 152 | 230.67° C. |
| 153 | 244.18° C. |
| 154 | 172.07° C. |
| 155 | 141.15° C. |
| 156 | 137.81° C. |
| 157 | 237.79° C. |
| 158 | 183.96° C. |
| 160 | 107.33° C. |
| 161 | 140.66° C. |
| 162 | 185.6-196.2° C. (*) |
| 163 | 158.93-161.18° C. (**) |
| 164 | 128.9-135.5° C. (*) |
| 165 | 221.81° C. |
| 166 | 219.92-226.67° C. (**) |
| 167 | 238.4-239.9° C. (*) |
| 172 | 176.53° C. |
| 174 | 135.5-137.6° C. (*) |
| 177 | 153.03° C. |
| 178 | 239.97-246.02° C. (**) |
| 179 | 208.5-211.4° C. (*) |
| 185 | 237.63° C. |
| 187 | 143.60-152.84° C. (**) |
| 188 | 180.36° C. |
| 189 | 135.95° C. |
| 190 | 237.27° C. |
| 193 | 229.80° C. |
| 194 | 169.39° C. |
| 197 | 119.47° C. |
| 198 | 240.21° C. |
| 199 | 191.24° C. |
| 201 | 176.81-180.81° C. (**) |
| 202 | 206.52-208.54° C. (**) |
| 203 | 227.09° C. |
| 204 | 216.07° C. |
| 205 | 245.16° C. |
| 206 | 165.0-172.0° C. (*) |
| 207 | 199.55° C. |
| 210 | 106.52° C. |
| 213 | 150.41° C. |
| 214 | 238.08° C. |
| 215 | 236.90° C. |
| 218 | 206.25° C. |
| 219 | 231.72-235.46° C. (**) |
| 221 | 240.92° C. |
| 223 | 238.02° C. |
| 225 | 270.26-272.63° C. (**) |
| 226 | 237.34-238.57° C. (**) |
| 227 | 199.27° C. |
| 228 | 223.61° C. |
| 229 | 143.26° C. |
| 230 | 227.82-231.33° C. (**) |
| 231 | 179.56° C. |
| 232 | 190.6-203.9° C. (*) |
| 233 | 211.39° C. |
| 234 | 165.15° C. |
| 236 | 111.43° C. |
| 240 | 149.04° C. |
| 241 | 149.45° C. |
| 242 | 204.17° C. |
| 243 | 188.36° C. |
| 244 | 180.26-193.16° C. (**) |
| 246 | 252.93° C. |
| 247 | 200.78-205.82° C. (**) |
| 248 | 240.96° C. |
| 249 | 251.15° C. |
| 250 | 237.64° C. |
| 251 | 192.63-195.46° C. (**) |
| 252 | 208.89° C. |
| 253 | 235.14-237.43° C. (**) |
| 255 | 197.51-202.70° C. (**) |
| 256 | 217.95° C. |
| 257 | 234.77° C. |
| 258 | 232.37° C. |
| 259 | 192.05° C. |
| 260 | 223.71-227.30° C. (**) |
| 261 | 215.71° C. |
| 262 | 235.72° C. |
| 263 | 239.54° C. |
| 264 | 203.54° C. |
| 265 | 221.88° C. |
| 267 | 215.62-218.06° C. (**) |
| 268 | 232.51° C. |
| 269 | 199.01° C. |
| 270 | 203.22° C. |

(*) measured with WRS-2A melting poing apparatus
(**) measured with Diamond DSC from PerkinElmer using a temperature gradient of 10° C./minute C.2 LCMS Procedures General Procedure A The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS General Procedure B

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

LCMS General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—Procedure 1

In addition to general procedure A: Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS—Procedure 2

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

LCMS—Procedure 3

In addition to general procedure A: Reversed phase HPLC was carried out on an Atlantis C18 column (3.5 µm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 µl was used. Cone voltage was 10 V for positive ionization mode and 20 V for negative ionization mode.

LCMS—Procedure 4

In addition to general procedure B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 µl were used. Oven temperature was 50° C. (MS polarity: positive)

LCMS—Procedure 5

In addition to general procedure B: Reversed phase HPLC was carried out on a YMC-Pack ODS-AQ, 50×2.0 mm 5 µm column with a flow rate of 0.8 ml/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 µl were used. Oven temperature was 50° C. (MS polarity: positive)

LCMS—Procedure 6

In addition to general procedure C: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

LCMS—Procedure 9

In addition to general procedure B: Reversed phase HPLC was carried out on an Ultimate XB-C18, 50×2.1 mm 5 µm column with a flow rate of 0.8 ml/min. Two mobile phases (mobile phase C: 10 mmol/L $NH_4HCO_3$; mobile phase D: acetonitrile) were used. First, 90% C and 10% D was hold for 0.8 minutes. Then a gradient was applied to 20% C and 80% D in 3.7 minutes and hold for 3 minutes. Typical injection volumes of 2 µl were used. Oven temperature was 50° C. (MS polarity: positive)

LCMS—Procedure 10

In addition to general procedure A: Column heater was set at 45° C. Reversed phase HPLC was carried out on an Xterra MS C18 column (3.5 µm, 4.6×100 mm) with a flow rate of 1.6 ml/min. Three mobile phases (mobile phase A: 0.1% formic acid in $H_2O$/methanol 95/5; mobile phase B: acetonitrile; mobile phase C: methanol) were employed to run a gradient condition from 100% A to 1% A, 49% B and 50% C in 7 minutes and hold these conditions for 1 minute. An injection volume of 10 µl was used. Cone voltage was 10 V for positive ionization mode.

TABLE F-7

LC/MS data - Retention time ($R_t$ in minutes of the main component), $(MH)^+$ peak (of the free base), LCMS procedure

| Co. Nr. | $R_t$ | $(MH)^+$ | LCMS Procedure |
|---|---|---|---|
| 2 | 0.82 | 527 | 6 |
| 3 | 0.99 | 525 | 6 |
| 4 | 0.88 | 491 | 6 |
| 5 | 0.98 | 517 | 6 |
| 6 | 0.85 | 477 | 6 |
| 9 | 0.74 | 463 | 6 |
| 13 | 0.95 | 492 | 6 |
| 14 | 1.05 | 518 | 6 |
| 15 | 1.14 | 552 | 6 |
| 16 | 1.04 | 526 | 6 |
| 23 | 0.63 | 567 | 6 |
| 26 | 0.60 | 581 | 6 |
| 36 | 6.43 | 551 | 1 |
| 41 | 4.10 | 448 | 1 |
| 42 | 6.13 | 654 | 1 |
| 52 | 4.29 | 493 | 4 |
| 54 | 3.46 | 566 | 5 |
| 55 | 3.54 | 666 | 1 |
| 56 | 0.99 | 491 | 6 |
| 57 | 0.83 | 493 | 6 |
| 58 | 0.86 | 463 | 6 |
| 59 | 0.97 | 502 | 6 |
| 60 | 2.77 | 579 | 5 |
| 61 | 4.24 | 579 | 9 |
| 62 | 3.69 | 501 | 5 |
| 66 | 5.53 | 540 | 1 |
| 73 | 3.89 | 462 | 4 |
| 82 | 2.93 | 502 | 5 |
| 88 | 6.34 | 566 | 5 |
| 90 | 3.92 | 554 | 4 |
| 94 | 4.37 | 490 | 1 |
| 99 | 4.26 | 566 | 1 |
| 100 | 5.36 | 608 | 1 |
| 103 | 6.64 | 666 | 1 |
| 104 | 4.58 | 610 | 2 |
| 105 | 4.60 | 610 | 2 |
| 107 | 6.22 | 525 | 1 |
| 108 | 5.93 | 592 | 1 |
| 162 | 4.60 | 569 | 4 |
| 164 | 4.50 | 500 | 4 |
| 109 | 5.45 | 527 | 2 |
| 112 | 6.35 | 509 | 2 |
| 114 | 5.91 | 552 | 2 |

TABLE F-7-continued

LC/MS data - Retention time ($R_t$ in minutes of the main component), $(MH)^+$ peak (of the free base), LCMS procedure

| Co. Nr. | $R_t$ | $(MH)^+$ | LCMS Procedure |
|---|---|---|---|
| 166 | 4.29 | 501 | 4 |
| 115 | 4.59 | 609 | 1 |
| 116 | 6.98 | 534 | 1 |
| 117 | 5.64 | 594 | 2 |
| 168 | 3.69 | 526 | 4 |
| 169 | 4.77 | 568 | 4 |
| 170 | 4.60 | 567 | 4 |
| 119 | 7.67 | 551 | 3 |
| 122 | 6.96 | 535 | 1 |
| 180 | 5.32 | 498 | 3 |
| 124 | 6.56 | 511 | 1 |
| 125 | 6.22 | 553 | 1 |
| 127 | 4.37 | 530 | 10 |
| 129 | 5.81 | 516 | 1 |
| 131 | 5.84 | 591 | 1 |
| 136 | 5.78 | 593 | 1 |
| 140 | 6.95 | 537 | 1 |
| 141 | 5.40 | 520 | 3 |
| 143 | 6.24 | 533 | 1 |
| 146 | 5.18 | 588 | 1 |
| 147 | 5.53 | 476 | 3 |
| 149 | 6.37 | 544 | 1 |

D. Pharmacological Data

D.1 hENT1-NBMPR-ERYTH Assay

The affinity of compounds to the human ENT1 transporter was determined in a binding assay using [$^3$H]NBMPR (19.9 Ci/mmol) from Moravek Biochemicals (Brea, Calif.). Erythrocytes were isolated from freshly isolated EDTA anti-coagulated human blood. 4 ml human whole blood was diluted in 11 ml wash buffer (20 mM MOPS, 130 mM NaCl, pH 7.4) and centrifuged at 800 g for 5 minutes. Erythrocytes were washed two times with wash buffer by centrifugation at 800 g for 5 minutes and then resuspended in wash buffer to the original whole blood volume and stored at −80° C. Binding experiments were performed at apparent binding equilibrium (30 minutes incubation at room temperature) with washed red blood cells diluted 1:200 in assay buffer (20 mM Tris, 140 mM NaCl, 5 mM NaCl, 2 mM MgCl2, 0.1 mM EDTA, 5 mM Glucose, pH 7.4) and 1 nM of radioligand. Test compounds were pre-incubated with the red blood cells for 30 minutes at room temperature. Non-specific binding was estimated in the presence of 1 µM Draflazine. The incubation was stopped by rapid filtration using Unifilter-96 GF/C filter plates on a 96-well PerkinElmer Filtermate harvester followed by three washes with ice-cold assay buffer. Bound radioactivity was determined by liquid scintillation counting (Topcount, (PerkinElmer)). The $pIC_{50}$=−log($IC_{50}$) values have been listed in the Table F-8 below.

TABLE F-8

$pIC_{50}$ values for ENT1 transporter inhibition

| Co. No. | pIC50 |
|---|---|
| 1 | 7.05 |
| 2 | 8.19 |
| 3 | 8.37 |
| 4 | 7.91 |
| 5 | 8.39 |
| 6 | 8.35 |
| 7 | 7.50 |
| 8 | 7.35 |
| 9 | 7.28 |
| 10 | 7.73 |
| 11 | 8.31 |
| 12 | 8.72 |
| 13 | 8.50 |
| 14 | 8.80 |
| 15 | 9.10 |
| 16 | 8.90 |
| 18 | 8.12 |
| 19 | 8.56 |
| 20 | 7.31 |
| 21 | 6.08 |
| 22 | 9.65 |
| 23 | 7.99 |
| 24 | 9.10 |
| 25 | 8.48 |
| 26 | 7.96 |
| 27 | 9.11 |
| 28 | 8.48 |
| 29 | 8.19 |
| 30 | 8.73 |
| 31 | 9.52 |
| 32 | 7.80 |
| 33 | 9.70 |
| 34 | 7.84 |
| 35 | 7.08 |
| 36 | 9.00 |
| 37 | 8.69 |
| 38 | 6.91 |
| 39 | 7.96 |
| 40 | 7.22 |
| 42 | 9.30 |
| 43 | 7.05 |
| 44 | 8.11 |
| 45 | 6.38 |
| 46 | 7.69 |
| 47 | 7.25 |
| 48 | 6.47 |
| 49 | 7.82 |
| 50 | 6.60 |
| 51 | 6.11 |
| 52 | 7.75 |
| 53 | 6.19 |
| 54 | 8.56 |
| 55 | 8.60 |
| 56 | 8.79 |
| 57 | 6.40 |
| 58 | 7.05 |
| 59 | 9.11 |
| 60 | 7.20 |
| 61 | 7.33 |
| 62 | 8.36 |
| 63 | 6.81 |
| 64 | 7.15 |
| 65 | 8.32 |
| 66 | 8.74 |
| 67 | 7.82 |
| 68 | 7.38 |
| 69 | 7.26 |
| 70 | 7.37 |
| 71 | 7.27 |
| 72 | 8.30 |
| 73 | 7.24 |
| 74 | 8.94 |
| 76 | 7.23 |
| 77 | 7.50 |
| 78 | 7.44 |
| 79 | 7.07 |
| 80 | 8.19 |
| 81 | 6.36 |
| 82 | 7.88 |
| 83 | 8.17 |
| 85 | 6.84 |
| 86 | 8.73 |
| 89 | 8.34 |
| 90 | 9.22 |
| 91 | 8.54 |
| 92 | 9.17 |

TABLE F-8-continued pIC$_{50}$ values for ENT1 transporter inhibition

| Co. No. | pIC50 |
|---|---|
| 93 | 6.92 |
| 94 | 7.38 |
| 95 | 8.78 |
| 96 | 9.11 |
| 97 | 7.92 |
| 98 | 6.83 |
| 99 | 8.38 |
| 100 | 9.23 |
| 101 | 9.53 |
| 102 | 8.26 |
| 104 | 9.09 |
| 105 | 7.87 |
| 108 | 10.35 |
| 109 | 8.81 |
| 110 | 7.24 |
| 111 | 7.74 |
| 112 | 9.73 |
| 114 | 8.55 |
| 115 | 8.39 |
| 116 | 9.18 |
| 117 | 9.23 |
| 120 | 6.90 |
| 122 | 9.29 |
| 124 | 9.12 |
| 125 | 8.87 |
| 126 | 9.33 |
| 127 | 9.11 |
| 130 | 8.01 |
| 131 | 9.49 |
| 133 | 8.74 |
| 135 | 7.59 |
| 136 | 8.92 |
| 137 | 9.41 |
| 138 | 9.31 |
| 140 | 10.10 |
| 141 | 8.43 |
| 143 | 8.54 |
| 144 | 8.74 |
| 145 | 8.82 |
| 146 | 9.22 |
| 147 | 8.26 |
| 148 | 8.10 |
| 149 | 9.46 |
| 151 | 7.64 |
| 152 | 7.93 |
| 153 | 7.26 |
| 154 | 7.92 |
| 155 | 7.71 |
| 156 | 8.69 |
| 157 | 7.96 |
| 158 | 7.91 |
| 161 | 8.43 |
| 162 | 8.07 |
| 163 | 9.30 |
| 164 | 7.91 |
| 165 | 6.49 |
| 166 | 7.38 |
| 167 | 7.55 |
| 168 | 6.57 |
| 169 | 8.35 |
| 170 | 7.65 |
| 172 | 6.91 |
| 177 | 8.42 |
| 178 | 7.18 |
| 179 | 8.01 |
| 185 | 8.995 |
| 186 | 7.615 |
| 187 | 8.815 |
| 188 | 8.07 |
| 189 | 8.59 |
| 190 | 8.605 |
| 193 | 7.54 |
| 194 | 7.945 |
| 195 | 8.105 |
| 196 | 7.73 |
| 197 | 8.335 |

TABLE F-8-continued pIC$_{50}$ values for ENT1 transporter inhibition

| Co. No. | pIC50 |
|---|---|
| 198 | 7.725 |
| 199 | 9.465 |
| 200 | 8.175 |
| 201 | 8.74 |
| 202 | 7.39 |
| 203 | 7.52 |
| 204 | 7.45 |
| 205 | 6.97 |
| 206 | 8.375 |
| 207 | 8.275 |
| 208 | 8.82 |
| 209 | 8.91 |
| 210 | 8.535 |
| 211 | 8.055 |
| 212 | 7.345 |
| 213 | 8.44 |
| 214 | 7.91 |
| 215 | 7.115 |
| 217 | 7.66 |
| 218 | 8.025 |
| 219 | 8.49 |
| 220 | 8.405 |
| 221 | 7.375 |
| 222 | 9.275 |
| 223 | 8.42 |
| 224 | 8.485 |
| 225 | 8.71 |
| 226 | 7.58 |
| 227 | |
| 228 | 7.72 |
| 229 | 7.16 |
| 230 | 7.18 |
| 231 | 8.77 |
| 232 | 8.06 |
| 233 | 8 |
| 234 | 7.735 |
| 235 | 7.005 |
| 236 | 9.335 |
| 238 | 7.925 |
| 239 | 8.815 |
| 240 | 8.16 |
| 241 | 7.4 |
| 242 | 8.28 |
| 243 | 8.215 |
| 244 | 7.09 |
| 245 | 7.51 |
| 246 | 8.44 |
| 247 | 7.56 |
| 248 | 6.6 |
| 249 | 8.31 |
| 250 | 7.95 |
| 251 | 7.675 |
| 252 | 7 |
| 253 | 7.29 |
| 254 | 7.895 |
| 255 | 5.76 |
| 256 | 6.5 |
| 257 | 7.36 |
| 258 | 7.33 |
| 259 | 6.29 |
| 260 | 6.98 |
| 261 | 6.68 |
| 262 | 6.88 |
| 263 | 7.05 |
| 264 | 7.905 |
| 265 | 6.22 |
| 266 | 7.32 |
| 267 | 5.94 |
| 268 | 6.19 |
| 269 | 7.21 |
| 270 | 5.42 |

The invention claimed is:
1. Compound of formula (I)

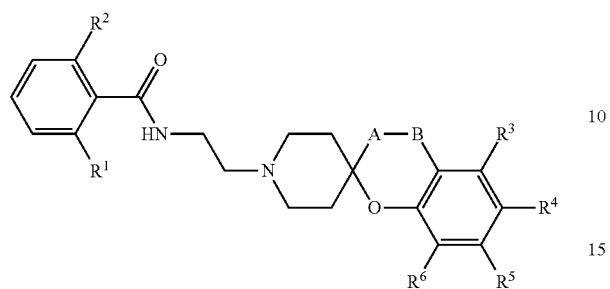

including any stereochemically isomeric form thereof, wherein -A-B— represents

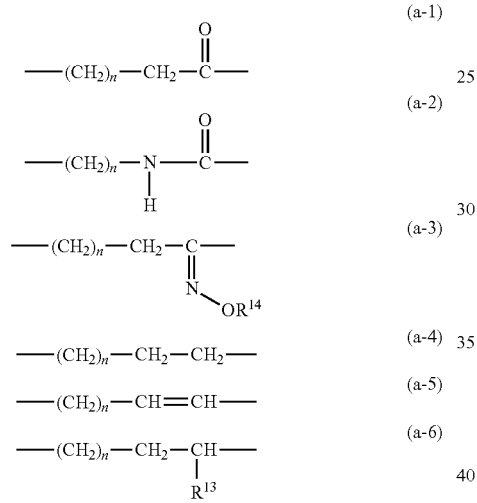

wherein n is an integer 0 or 1;
  $R^{13}$ represents hydroxy or halo;
  $R^{14}$ represents hydrogen or $C_{1-6}$alkyl;
in the bivalent radicals (a-4), (a-5) and (a-6) any of the hydrogen atoms on the same or a different carbon atom may be replaced by halo;
$R^1$ and $R^2$ are each independently selected from hydrogen, halo or $C_{1-6}$alkyl;
$R^3$, $R^4$, $R^5$ and $R^6$ are each independently selected from hydrogen, halo, $C_{1-6}$alkyl, polyhalo$C_{1-6}$alkyl, $C_{3-6}$cycloalkyl, $NO_2$, Cycle$^1$, Cycle$^2$,
or X—$R^8$ wherein X represents O or $NR^9$,
  wherein $R^9$ is hydrogen, $C_{1-6}$alkyl or $C_{1-6}$alkyloxy$C_{1-6}$alkyl, and
  wherein $R^8$ is hydrogen, $C_{1-6}$alkyl, $C_{2-6}$alkenyl, $C_{3-6}$cycloalkyl, polyhalo$C_{1-6}$alkyl, $C_{1-6}$alkyloxycarbonyl, $C_{1-6}$alkylcarbonyl, polyhalo$C_{1-6}$alkylcarbonyl, Cycle$^2$, —(C=O)—(CH$_2$)$_m$-Cycle$^2$, —(C=O)—(CH$_2$)$_m$—CH$_2$—OH, —(C=O)—(CH$_2$)$_m$—CH$_2$—O—$C_{1-4}$alkyl, or $C_{1-6}$alkyl substituted with halo, hydroxy, cyano, $C_{3-6}$cycloalkyl, $C_{1-6}$alkyloxy, aminocarbonyl, phenyl, Cycle$^1$, or Cycle$^2$, or $NR^{11}R^{12}$ wherein $R^{11}$ and $R^{12}$ are each independently selected from hydrogen, $C_{1-6}$alkyl, $C_{1-6}$alkylcarbonyl, or $C_{1-6}$alkyloxycarbonyl;

m is an integer 0, 1 or 2;
Cycle$^1$ is selected from

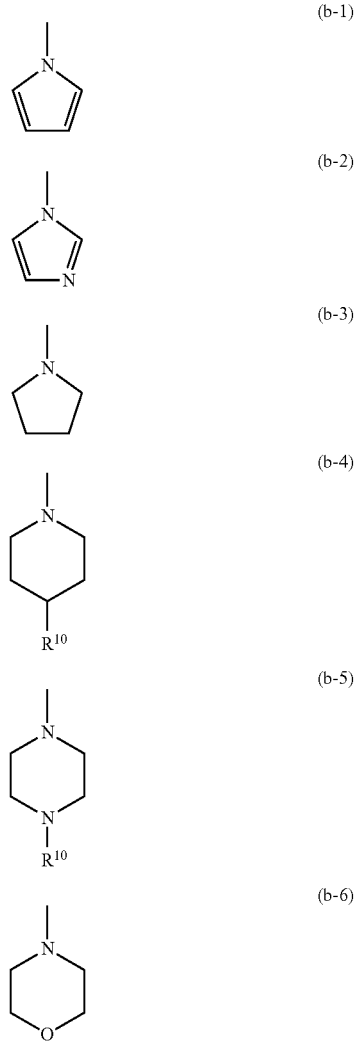

wherein $R^{10}$ is hydrogen, $C_{1-6}$alkyl, $C_{1-6}$alkylcarbonyl, or $C_{1-6}$alkyloxycarbonyl; and
Cycle$^2$ is selected from

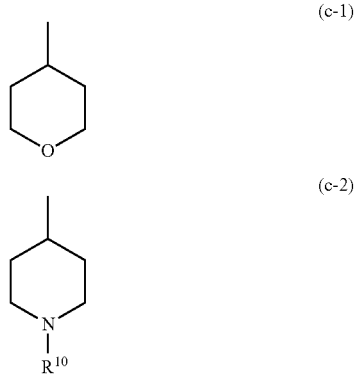

(c-3)

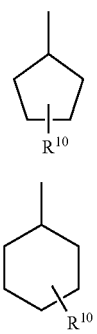

(c-4)

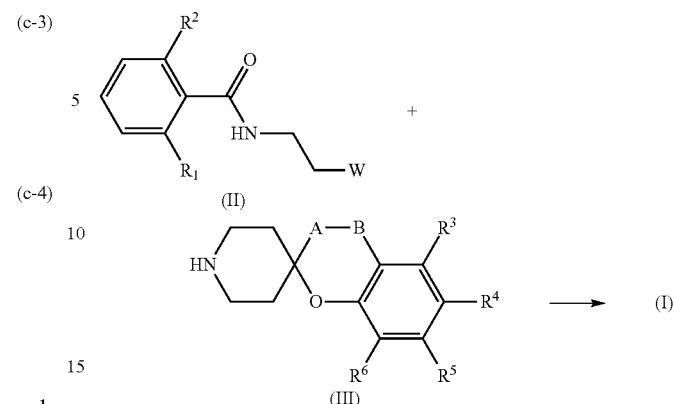

wherein $R^{10}$ is hydrogen, $C_{1-6}$alkyl, $C_{1-6}$alkylcarbonyl, $C_{1-6}$alkyloxycarbonyl or $C_{1-6}$alkyloxycarbonyl substituted with halo or hydroxy;

or a pharmaceutically acceptable acid addition salt thereof, or an N-oxide form thereof.

2. A compound as claimed in claim 1 wherein $R^1$ and $R^2$ are both halo.

3. A compound as claimed in claim 1 wherein $R^1$ and $R^2$ are both $C_{1-4}$alkyl.

4. A compound as claimed in claim 1 wherein radical -A-B— represents (a-1).

5. A compound as claimed in claim 1 wherein radical -A-B— represents (a-2).

6. A compound as claimed in claim 1 wherein $R^3$ is hydrogen and $R^5$ is X—$R^8$.

7. A compound as claimed in claim 1 wherein the compound is N-(2-{7-[(1-acetylpiperidin-4-yl)oxy]-6-chloro-4-oxo-3,4-dihydro-1'H-spiro[chromene-2,4'-piperidin]-1'-yl}ethyl)-2,6-dichlorobenzamide or a pharmaceutically acceptable acid addition salt thereof.

8. A compound as claimed in claim 1 wherein the compound is N-[2-(7-amino-8-chloro-4-oxo-3,4-dihydro-1'H-spiro[1,3-benzoxazine-2,4'-piperidin]-1'-yl)ethyl]-2,6-dichlorobenzamide or a pharmaceutically acceptable acid addition salt thereof.

9. A pharmaceutical composition comprising a pharmaceutically acceptable carrier and a therapeutically active amount of a compound according to claim 1.

10. A process for preparing a compound of formula (I) wherein
   a) a compound of formula (III) is N-alkylated with a compound of formula (II) in a reaction-inert solvent, or; b) a compound of formula (IV) is reacted with a compound of formula (V) in a reaction-inert solvent,

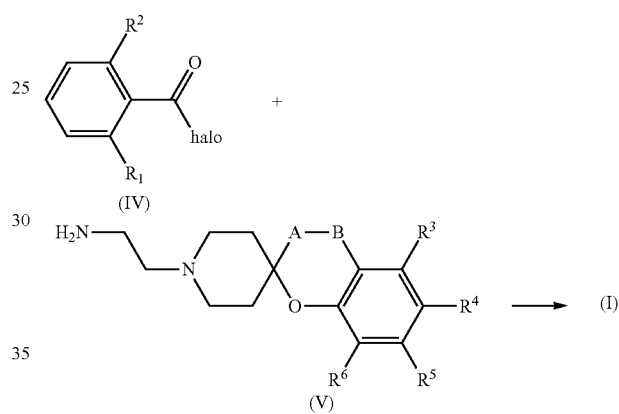

or c) compounds of formula (I) are converted into each other following art-known transformation reactions.

11. A method of treating acute and chronic pain in a mammalian subject, which method comprises administering to a mammal in need of such treatment a therapeutically effective amount of a compound of formula (I) according to claim 1 or a pharmaceutically acceptable salt thereof.

12. A process according to claim 10 wherein the reaction occurs in the presence of a suitable base.

* * * * *